United States Patent
Ali et al.

(10) Patent No.: US 10,822,338 B2
(45) Date of Patent: Nov. 3, 2020

(54) SUBSTITUTED AMINOQUINAZOLINE COMPOUNDS AS $A_{2A}$ ANTAGONIST

(71) Applicant: Merck Sharp & Dohme Corp., Rahway, NJ (US)

(72) Inventors: Amjad Ali, Freehold, NJ (US); Xianhai Huang, Warren, NJ (US); Yeon-Hee Lim, San Mateo, CA (US); Rongze Kuang, Green Brook, NJ (US); Heping Wu, Edison, NJ (US); Rajan Anand, Fanwood, NJ (US); Younong Yu, East Brunswick, NJ (US); Edward Metzger, Laurel, MD (US); Michael Man-Chu Lo, Bedminster, NJ (US); Pauline C. Ting, New Providence, NJ (US); Andrew W. Stamford, Chatham, NJ (US); Paul Tempest, Taipei (TW)

(73) Assignee: Merck Sharp & Dohme Corp., Rahway, NJ (US)

( * ) Notice: Subject to any disclaimer, the term of this patent is extended or adjusted under 35 U.S.C. 154(b) by 113 days.

(21) Appl. No.: 15/738,178

(22) PCT Filed: Jul. 5, 2016

(86) PCT No.: PCT/US2016/040926
§ 371 (c)(1),
(2) Date: Dec. 20, 2017

(87) PCT Pub. No.: WO2017/011214
PCT Pub. Date: Jan. 19, 2017

(65) Prior Publication Data
US 2018/0362530 A1     Dec. 20, 2018

(30) Foreign Application Priority Data
Jul. 10, 2015  (WO) ................ PCT/CN2015/083777

(51) Int. Cl.
*C07D 487/04*   (2006.01)
*C07D 491/153*  (2006.01)

(52) U.S. Cl.
CPC ....... *C07D 487/04* (2013.01); *C07D 491/153* (2013.01)

(58) Field of Classification Search
CPC ............................ C07D 487/04; C07D 491/14
See application file for complete search history.

(56) References Cited

U.S. PATENT DOCUMENTS

| | | |
|---|---|---|
| 4,713,383 A | 12/1987 | Francis et al. |
| 5,565,460 A | 10/1996 | Suzuki et al. |
| 6,358,964 B1 | 3/2002 | Baraldi |
| 6,630,475 B2 | 10/2003 | Neustadt et al. |

(Continued)

FOREIGN PATENT DOCUMENTS

| | | |
|---|---|---|
| WO | WO199852568 | 11/1998 |
| WO | WO2011060207 | 5/2011 |
| WO | 2015027431 | 8/2013 |

(Continued)

OTHER PUBLICATIONS

The University of Rochester. Overview of Nervous System Disorders—Health Encyclopedia. (2019) Web : https://www.urmc.rochester.edu/encyclopedia/content.aspx?contenttypeid=85&contentid=P00799.*

(Continued)

*Primary Examiner* — Emily A Bernhardt
*Assistant Examiner* — Laura M Daniel
(74) *Attorney, Agent, or Firm* — Janet E. Fair; Catherine D. Fitch

(57) ABSTRACT

The present invention is directed to compounds of generic formula (I): or pharmaceutically acceptable salts thereof that are believed to be useful as an $A_{2A}$-receptor antagonist. The invention is further directed to methods of treating a patient (preferably a human) for diseases or disorders in which the $A_{2A}$-receptor is involved. The invention further involves use of the compounds as an $A_{2A}$-receptor antagonist and/or inhibitor for the preparation of a medicament for the treatment and/or prevention of diseases associated with inhibiting the receptor, which includes central nervous system disorders such as Parkinson's disease. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

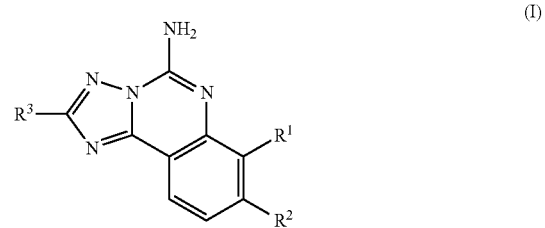

(I)

17 Claims, No Drawings

(56) References Cited

U.S. PATENT DOCUMENTS

2006/0128694 A1    6/2006    Grzelak et al.

FOREIGN PATENT DOCUMENTS

| WO | WO2014101113 | 7/2014 |
|---|---|---|
| WO | WO2014101120 | 7/2014 |

OTHER PUBLICATIONS

Cieslak, Marek. Purinergic Signalling (2008) 4:305-312.*
Adenot, M. Eur. J. Med Chem (1997) 32, 493-504.*
Balo, C et al, Synthesis and Evaluation of Adenosine Antagonist Activity of a Series of [1,2,4]Triazolo[1,5-c] quinazolines, Chemical and Pharmaceutical Bulletin, 2007, 372-375, 55 (3).
Berge, S.M., et al.,, "Pharmaceutical Salts", J. Pharm. Sci, 1977, pp. 1-19, vol. 66, No. 1.
Bingham, A.L., et al.,, "Over One Hundred Solvates of sulfathiazole", Chem. Commun., 2001, pp. 603-604.
Caira, M.R., et al.,, "Preparation and Crystal Characterization of a Polymorph,a Monohydrate, and an Ethyl Acetate Solvate of the Antifungal Fluconazole", J. Pharmaceutical Sci., 2004, pp. 601-611, vol. 93, No. 3.
Gould, Salt selection for basic drugs, International J. of Pharmaceutics, 1986, 201-217, 33.
PubChem CID: 14031894, Create Date: Feb. 9, 2007 (Feb. 9, 2007), Date Accessed: Aug. 25, 2016 (Aug. 25, 2016) p. 3, compound listed.
Stahl et al., Aminoquinazoline Compounds as A2A Antagonist, Handbook of Pharmaceutical Salts Properties, Selection, and Use, 2002, 330-331.
Van Tonder et al., Preparation and Physicochemical Characterization of 5 Niclosamide Solvates and 1 Hemisolvate and 1 Hemisolvate, AAPS PharmSciTech, 2004, Article 12, 5(1).

* cited by examiner

SUBSTITUTED AMINOQUINAZOLINE COMPOUNDS AS $A_{2A}$ ANTAGONIST

CROSS REFERENCE TO RELATED APPLICATIONS

This application is the National Stage of International Application No. PCT/US2016/40926 filed on Jul. 5, 2016, which claims the benefit under International Application No. PCT/CN2015/083777, filed on Jul. 10, 2015.

BACKGROUND OF THE INVENTION

Adenosine is known to be an endogenous modulator of a number of physiological functions. At the cardiovascular system level, adenosine is a strong vasodilator and a cardiac depressor. On the central nervous system, adenosine induces sedative, anxiolytic and antiepileptic effects. On the respiratory system, adenosine induces bronchoconstriction. At the kidney level, it exerts a biphasic action, inducing vasoconstriction at low concentrations and vasodilation at high doses. Adenosine acts as a lipolysis inhibitor on fat cells and as an anti-aggregant on platelets.

Adenosine action is mediated by the interaction with different membrane specific receptors which belong to the family of receptors coupled with G proteins. Biochemical and pharmacological studies, together with advances in molecular biology, have allowed the identification of at least four subtypes of adenosine receptors: $A_1$, $A_{2A}$, $A_{2b}$ and $A_3$. $A_1$ and $A_3$ are high-affinity, inhibiting the activity of the enzyme adenylate cyclase, and $A_{2A}$ and $A_{2b}$ are low-affinity, stimulating the activity of the same enzyme.

Analogs of adenosine able to interact as antagonists with the $A_1$, $A_{2A}$, $A_{2b}$ and $A_3$ receptors have also been identified. Selective antagonists for the $A_{2A}$ receptor are of pharmacological interest because of their reduced level of side effects. In the central nervous system, $A_{2A}$ antagonists can have antidepressant properties and stimulate cognitive functions. Moreover, data has shown that $A_{2A}$ receptors are present in high density in the basal ganglia, known to be important in the control of movement. Hence, $A_{2A}$ antagonists can improve motor impairment due to neurodegenerative diseases, for example, Parkinson's disease, senile dementia as in Alzheimer's disease, and psychoses of organic origin.

Some xanthine-related compounds have been found to be $A_1$ receptor selective antagonists, and xanthine and non-xanthine compounds have been found to have high $A_{2A}$ affinity with varying degrees of $A_{2A}$ vs. $A_1$ selectivity. Triazolo-pyrimidine adenosine $A_{2A}$ receptor antagonists with different substitution at the 7-position have been disclosed previously, for example in PCT International Application Publication Nos. WO 95/01356; U.S. Pat. No. 5,565,460; WO 97/05138; and WO 98/52568. See also WO2015/027431.

Parkinson's disease is characterized by progressive degeneration of the nigrostriatal dopaminergic pathway. The subsequent reduction in striatal dopamine levels is responsible for motor symptoms associated with Parkinson's disease, e.g., the loss of fine motor control or motor impairment manifested in those suffering from the disease. Current methodologies for alleviating motor symptoms associated with Parkinson's disease seek to replace dopamine either within the presynaptic terminal, for example, by administration of L-DOPA, directly through stimulation of the postsynaptic $D_2$ receptors, or by inhibiting metabolism, for example, by administration of monoamine oxidase type B (MAO-B) or catechol-O-methyltransferase (COMT). Long term use of such therapies is often associated with adverse events. For example, long term therapy with L-DOPA (currently the standard of care) is often associated with adverse events (e.g. motor complications), for example, "wearing-off", "random on-off" oscillations, or dyskinesia. These motor complications arising from therapy administered to manage Parkinson's disease often become progressively more severe with continued treatment.

As mentioned above, $A_{2A}$ receptors are present in high density in the basal ganglia and are known to be important in the control of fine motor movement. Highly selective $A_{2A}$ antagonists have demonstrated their efficacy in reducing motor symptoms associated with neurodegenerative diseases. Accordingly, compounds which are $A_{2A}$ receptor antagonists are believed to be useful in alleviating motor symptoms associated with Parkinson's disease. For example, U.S. Pat. No. 6,630,475 to Neustadt et al. (the '475 patent) describes the preparation of the compound of Formula PI:

Formula PI

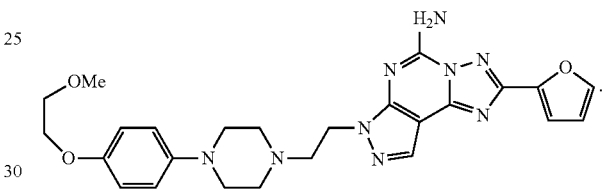

In the '475 patent example Schemes 1 to 5, along with preparative Schemes 1 to 4, show general methods of preparing compounds of Formula PI. The '475 patent describes also that the compound of Formula I can be prepared as a pharmaceutically acceptable salt which may be useful for treating Parkinson's disease.

The use of $A_{2A}$ receptor antagonists in the potential treatment of central nervous system diseases, in particular Parkinson's disease, and to pharmaceutical compositions comprising said compounds has elevated the need for potent, moderately lipophilic, brain penetrant inhibitors of the $A_{2A}$ receptor. Such compounds would provide an expansion of the arsenal of compounds which are believed to have value in the treatment of central nervous system disorders, in particular treating or managing the progression of such diseases, for example, but not limited to, Parkinson's disease.

SUMMARY OF THE INVENTION

The present invention is directed to compounds of generic formula (I) below or pharmaceutically acceptable salts thereof that are believed to be useful as an $A_{2A}$-receptor antagonist.

The invention is further directed to methods of treating a patient (preferably a human) for diseases or disorders in which the $A_{2A}$-receptor is involved. The invention further involves use of the compounds as an $A_{2A}$-receptor antagonist and/or inhibitor for the preparation of a medicament for the treatment and/or prevention of diseases associated with inhibiting the receptor, which includes central nervous system disorders such as Parkinson's disease. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one aspect, the invention is directed to compounds of general formula I:

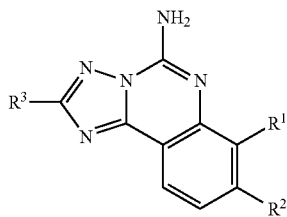

or a pharmaceutically acceptable salt thereof, wherein:
R represents hydrogen or —$C_{1-6}$alkyl,
$R^1$ is selected from the group consisting of hydrogen, —$C_{1-6}$alkyl, —$OC_{1-6}$alkyl, or halogen, said alkyl optionally substituted with 1 to 4 groups of $R^b$;
$R^2$ is selected from the group consisting of hydrogen, —$C_{1-6}$alkyl, or halogen, said alkyl optionally substituted with 1 to 3 groups of $R^b$;
$R^1$ and $R^2$ can combine with the atoms to which they are attached to form difluoro substituted dioxolo cyclic ring which together with the other ring members form a difluorosubstituted dioxolotriazoloquinazolinyl tetracyclic ring;
$R^3$ represents $C_{3-10}$ cycloalkyl, or $C_{3-10}$ heterocyclyl, said aryl and heterocyclyl optionally substituted with 1 to 3 groups of $R^a$;
$R^a$ is selected from the group consisting of —CN, halogen, —$C_{1-4}$haloalkyl, —$OC_{1-4}$haloalkyl, —$C_{1-6}$alkyl, —$C_{1-6}$alkenyl, $(CH_2)_nN(R)_2$, —$(CH_2)_nOC_{1-6}$alkyl, OH, $(CHR)_nC_{6-10}$ aryl, $(CHR)_nC_{3-10}$ heterocyclyl, $(CHR)_nC_{3-10}$cycloalkyl, —$C(O)C_{1-6}$alkyl, —$C(O)C_{3-10}$cycloalkyl), $SO_2C_{1-6}$alkyl, $C(O)C_{3-10}$ heterocyclyl, $C(O)C_{6-10}$aryl, $SO_2C_{6-10}$aryl, said alkyl, cycloalkyl, alkenyl, aryl and heterocyclyl optionally substituted with 1 to 4 groups of $R^b$;
$R^b$ is selected from the group consisting of —$C_{1-6}$alkyl, $C_{2-4}$alkynyl, —$C_{1-6}$alkylOR, $(CH_2)_nOR$, —$(CH_2)_nC_{1-4}$haloalkyl, —$OC_{1-4}$haloalkyl, halogen, $N(R)_2$, CN, C(O)R, $C(O)CF_3$, —$(CH_2)_nC_{6-10}$ aryl, —$O(CH_2)_nC_{6-10}$ aryl, —$(CH_2)_nC_{3-10}$ heterocyclyl, —$(CH_2)_nC_{3-10}$ cycloalkyl;
and n represents 0-4.

An embodiment of the invention of formula I is realized when $R^1$ is —$OC_{1-6}$alkyl. A subembodiment of this aspect of the invention is realized when $R^1$ is —$OCH_3$.

Another embodiment of the invention of formula I is realized when $R^1$ is halogen.

Another embodiment of the invention of formula I is realized when $R^2$ is hydrogen.

Another embodiment of the invention of formula I is realized when $R^2$ is halogen. A subembodiment of this aspect of the invention is realized when the $R^2$ halogen is chlorine. A subembodiment of this aspect of the invention is realized when the $R^2$ halogen is fluorine.

Yet another embodiment of the invention of formula I is realized when $R^1$ and $R^2$ combine with the carbon atoms to which they are attached to form a difluoro substituted dioxolo cyclic ring which together with the other ring members form a difluorosubstituted dioxolotriazoloqinazolinyl tetracyclic ring.

Still another embodiment of the invention of formula I is realized when $R^1$ is $OCH_3$ and $R^2$ is hydrogen.

Yet another embodiment of the invention of formula I is realized when $R^a$ is selected from the group consisting of halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR)_nC_{3-10}$cycloalkyl, —$C(O)$ $C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

Still another embodiment the invention of formula I is realized when $R^a$ is selected from the group consisting of $CH_3$, $CH_2CH_3$, —$(CH_2)_3CH_3$, $CH_2CH(CH_3)_2$, $C(CH_3)_2CH_2CH_3$, $(CH_2)_nOCH_3$, $CH_2CF_2CF_3$, $(CH_2)_nCF_3$, halogen, $(CH_2)$ $CH(CF_3)_2$, $CH_2CHF_2$, $C(CH_3)_2C\equiv C$, —$(CH_2)_n$ $N(R)_2$, OH, C(O)cyclopropyl, $(CHR)_n$cyclopropyl, $(CHR)_n$ pyridyl, $(CHR)_n$tetrahydropyranyl, $(CHR)_n$cyclobutyl, $(CHR)_n$thiadiazolyl, $(CHR)_n$oxetanyl, $(CHR)_n$cyclopentyl, $(CHR)_n$cyclohexyl, $(CHR)_n$phenyl, $(CHR)_n$thiazolyl, C(O) phenyl, C(O)pyridyl, $C(O)C(CH_3)_2F$, C(O)oxazolyl, C(O)C $(CH_3)_3$, C(O)thiophenyl, $SO_2$phenyl, $(CHR)_n$cyclopentyl, $(CHRl)_n$morpholinyl, and $(CHR)_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of $R^b$.

Still another embodiment of the invention of formula I is realized when $R^b$ is selected from halogen, $CH_3$, $CHF_2$, $(CH_2)_nCF_3$, CN, $C(O)CF_3$, $CH_2$phenyl, pyridyl, $CH(CH_3)_2$, $N(CH_3)_2$, $C(CH_3)_3$, $CH_2CH_3$, $C(CH_3)F_2$, $OCH_3$, morpholinyl, —$OCH_2$phenyl, $(CH_2)_2OCH_3$, cyclopropyl, —Ophenyl, OH, and $CH_2OH$.

Another embodiment of the invention of formula I is realized when $R^3$ is $C_{3-10}$ heterocyclyl, said heterocycle group optionally substituted with 1 to 3 groups of $R^a$. A subembodiment of this aspect of the invention is realized when $R^3$ is substituted —$C_{3-10}$ heterocyclyl. Still another subembodiment of this aspect of the invention is realized when the heterocycle of $R^3$ is selected from the group consisting unsubstituted or substituted piperidinyl, morpholinyl, tetrahydropyranyl, azabicyclooctyl, azabicycloheptyl, azepanyl, azetidinyl, pyrrolidinyl, cyclopentapyridinyl, and piperidinone.

Yet another aspect of the invention is realized when the heterocycle of $R^3$ is unsubstituted or substituted piperidinyl. Still another aspect of the invention is realized when the heterocycle of $R^3$ is unsubstituted or substituted morpholinyl. Still another aspect of the invention is realized when the heterocycle of $R^3$ is unsubstituted or substituted tetrahydropyranyl. Still another aspect of the invention is realized when the heterocycle of $R^3$ is unsubstituted or substituted cyclopentapyridinyl. Another aspect of the invention is realized when the heterocycle of $R^3$ is unsubstituted or substituted azabicyclooctyl. Another aspect of the invention is realized when the heterocycle of $R^3$ is unsubstituted or substituted azabicyloheptyl. Yet another aspect of the invention is realized when the heterocycle of $R^3$ is unsubstituted or substituted azepanyl. Another aspect of the invention is realized when the heterocycle of $R^3$ is unsubstituted or substituted azetidinyl. Yet another aspect of the invention is realized when the heterocycle of $R^3$ is unsubstituted or substituted pyrrolidinyl. Yet another aspect of the invention is realized when the heterocycle of $R^3$ is unsubstituted or substituted piperidinone.

Still another embodiment of the invention of formula I is realized when R³ is a nitrogen containing heterocyclyl selected from structural formulas (a), (b), (c), (d), (e), (f), (g), (h), (i) and (j):

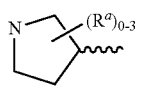
(a)

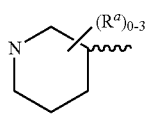
(b)

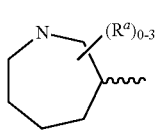
(c)

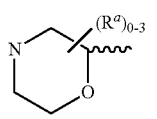
(d)

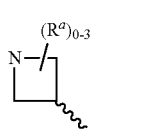
(e)

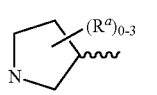
(f)

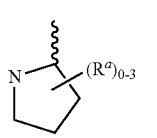
(g)

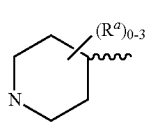
(h)

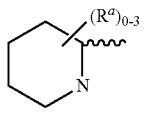
(i)

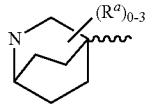
(j)

wherein $R^a$ can be present on any carbon and/or any nitrogen atom, two $R^a$'s can be present on a single carbon atom, and wherein when $R^a$ is 0 then nitrogen atoms requiring complete valency are substituted with hydrogen. A subembodiment of the invention of formula I wherein R³ is a nitrogen containing heterocyclyl selected from structural formulas (a), (b), (c), (d), (e), (f), (g), (h), (i) and (j) is realized when $R^a$ is selected from the group consisting of halogen, —$C_{1-4}$ haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR))_nC_{3-10}$cycloalkyl, —$C(O)C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

Still another embodiment the invention of formula I is realized when $R^a$ of structural formulas (a), (b), (c), (d), (e), (f), (g), (h), (i) and (j) is selected from the group consisting of $CH_3$, $CH_2CH_3$, —$(CH_2)_3CH_3$, $CH_2CH(CH_3)_2$, $C(CH_3)_2$ $CH_2CH_3$, $(CH_2)_nOCH_3$, $CH_2CF_2CF_3$, $(CH_2)_nCF_3$, halogen, $(CH_2)$ $CH(CF_3)_2$, $CH_2CHF_2$, $C(CH_3)_2C\equiv C$, —$(CH_2)_n$ $N(R)_2$, OH, C(O)cyclopropyl, $(CHR)_n$cyclopropyl, $(CHR)_n$ pyridyl, $(CHR)_n$tetrahydropyranyl, $(CHR)_n$cyclobutyl, $(CHR)_n$thiadiazolyl, $(CHR)_n$oxetanyl, $(CHR)_n$cyclopentyl, $(CHR)_n$cyclohexyl, $(CHR)_n$phenyl, $(CHR)_n$thiazolyl, C(O) phenyl, C(O)pyridyl, $C(O)C(CH_3)_2F$, C(O)oxazolyl, C(O)C $(CH_3)_3$, C(O)thiophenyl, $SO_2$phenyl, $(CHR)_n$cyclopentyl, $(CHR1)_n$morpholinyl, and $(CHR)_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of $R^b$.

A subembodiment of the aspect of the invention of formula I is realized when R³ is a nitrogen containing heterocyclyl of structural formula (a). Another subembodiment of the aspect of the invention of formula I is realized when R³ is a nitrogen containing heterocyclyl of structural formula (b). Another subembodiment of the aspect of the invention of formula I is realized when R³ is a nitrogen containing heterocyclyl of structural formula (c). Another subembodiment of the aspect of the invention of formula I is realized when R³ is a nitrogen containing heterocyclyl of structural formula (d). Another subembodiment of the aspect of the invention of formula I is realized when R³ is a nitrogen containing heterocyclyl of structural formula (e). Another subembodiment of the aspect of the invention of formula I is realized when R³ is a nitrogen containing heterocyclyl of structural formula (f). Another subembodiment of the aspect of the invention of formula I is realized when R³ is a nitrogen containing heterocyclyl of structural formula (g). Another subembodiment of the aspect of the invention of formula I is realized when R³ is a nitrogen containing heterocyclyl of structural formula (h). Another subembodiment of the aspect of the invention of formula I is realized when R³ is a nitrogen containing heterocyclyl of structural formula (i). Another subembodiment of the aspect of the invention of formula I is realized when R³ is a nitrogen containing heterocyclyl of structural formula (j).

Another embodiment of the invention of formula I is represented by structural formula II:

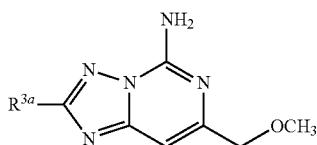
II

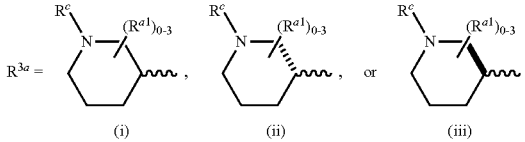

or a pharmaceutically acceptable salt thereof, wherein $R^c$ is hydrogen or $R^a$, $R^{a1}$ is $R^a$, and $R^a$ is as originally described.

A subembodiment of the invention of formula II is realized when $R^c$ is $R^a$ and the number of $(R^{a1})$ is 0-1. Another subembodiment of the invention of formula II is realized when $R^c$ is $R^a$ and the number of $(R^{a1})$ is 0. Another subembodiment of the invention of formula II is realized when $R^c$ is $R^a$ and the number of $(R^{a1})$ is 1. Still another subembodiment of the invention of formula II is realized when $R^c$ is elected from the group consisting of hydrogen, halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR))_nC_{3-10}$cycloalkyl, —C(O)$C_{1-6}$alkyl, —C(O)$C_{3-10}$cycloalkyl), —C(O)$C_{3-10}$heterocyclyl, said alkyl, cycloalkyl, aryl and heterocyclyl optionally substituted with 1 to 4 groups of $R^b$.

Yet another subembodiment of the invention of formula II is realized when $R^c$ is selected from the group consisting of $CH_3$, $CH_2CH_3$, —$(CH_2)_3CH_3$, $CH_2CH(CH_3)_2$, $C(CH_3)_2CH_2CH_3$, $(CH_2)_nOCH_3$, $CH_2CF_2CF_3$, $(CH_2)_nCF_3$, halogen, $(CH_2)$ $CH(CF_3)_2$, $CH_2CHF_2$, $C(CH_3)_2C≡C$, —$(CH_2)_nN(R)_2$, OH, C(O)cyclopropyl, $(CHR)_n$cyclopropyl, $(CHR)_n$pyridyl, $(CHR)_n$tetrahydropyranyl, $(CHR)_n$cyclobutyl, $(CHR)_n$thiadiazolyl, $(CHR)_n$oxetanyl, $(CHR)_n$cyclopentyl, $(CHR)_n$cyclohexyl, $(CHR)_n$phenyl, $(CHR)_n$thiazolyl, C(O)phenyl, C(O)pyridyl, $C(O)C(CH_3)_2F$, C(O)oxazolyl, $C(O)C(CH_3)_3$, C(O)thiophenyl, $SO_2$phenyl, $(CHR)_n$cyclopentyl, $(CHRl)_n$morpholinyl, and $(CHR)_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of $R^b$ and the number of $R^{a1}$ present is 0. A subembodiment of the invention of formula II is realized when $R^{3a}$ is (i). Another subembodiment of the invention of formula II is realized when $R^{3a}$ is (ii). Still another subembodiment of the invention of formula II is realized when $R^{3a}$ is (iii).

Another embodiment of the invention of formula I is represented by structural formula III:

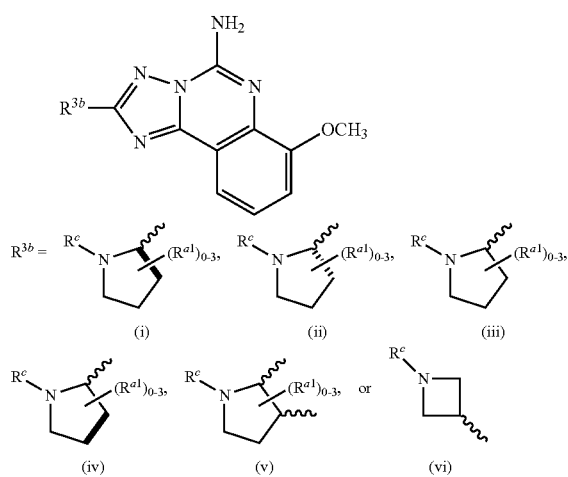

or a pharmaceutically acceptable salt thereof, wherein $R^c$ and $R^{a1}$ are as originally described.

A subembodiment of the invention of formula III is realized when $R^c$ is $R^a$ and the number of $(R^{a1})$ is 0-1. Another subembodiment of the invention of formula III is realized when $R^c$ is $R^a$ and the number of $(R^{a1})$ is 0. Another subembodiment of the invention of formula III is realized when $R^c$ is $R^a$ and the number of $(R^{a1})$ is 1. Still another subembodiment of the invention of formula III is realized when $R^c$ is selected from the group consisting of halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR)_nC_{3-10}$cycloalkyl, —C(O)$C_{1-6}$alkyl, —C(O)$C_{3-10}$cycloalkyl), —C(O)$C_{3-10}$heterocyclyl, said alkyl, cycloalkyl, aryl and heterocyclyl optionally substituted with 1 to 4 groups of $R^b$. Yet another subembodiment of the invention of formula III is realized when $R^c$ is selected from the group consisting of $CH_3$, $CH_2CH_3$, —$(CH_2)_3CH_3$, $CH_2CH(CH_3)_2$, $C(CH_3)_2CH_2CH_3$, $(CH_2)_nOCH_3$, $CH_2CF_2CF_3$, $(CH_2)_nCF_3$, halogen, $(CH_2) CH(CF_3)_2$, $CH_2CHF_2$, $C(CH_3)_2C≡C$, —$(CH_2)_nN(R)_2$, OH, C(O)cyclopropyl, $(CHR)_n$cyclopropyl, $(CHR)_n$pyridyl, $(CHR)_n$tetrahydropyranyl, $(CHR)_n$cyclobutyl, $(CHR)_n$thiadiazolyl, $(CHR)_n$oxetanyl, $(CHR)_n$cyclopentyl, $(CHR)_n$cyclohexyl, $(CHR)_n$phenyl, $(CHR)_n$thiazolyl, C(O)phenyl, C(O)pyridyl, $C(O)C(CH_3)_2F$, C(O)oxazolyl, $C(O)C(CH_3)_3$, C(O)thiophenyl, $SO_2$phenyl, $(CHR)_n$cyclopentyl, $(CHRl)_n$morpholinyl, and $(CHR)_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of $R^b$ and the number of $R^{a1}$ present is 0. Another embodiment of the invention of formula III is realized when $R^{3b}$ is (i). Another embodiment of the invention of formula III is realized when $R^{3b}$ is (ii). Another embodiment of the invention of formula III is realized when $R^{3b}$ is (iii). Another embodiment of the invention of formula III is realized when $R^{3b}$ is (iv). Another embodiment of the invention of formula III is realized when $R^{3b}$ is (v). Another embodiment of the invention of formula III is realized when $R^{3b}$ is (vi).

Another embodiment of the invention of formula I is represented by structural formula IV:

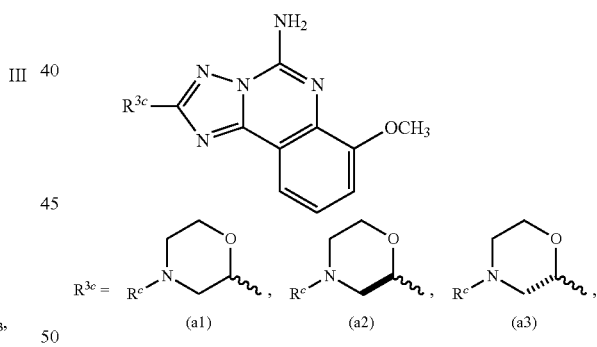

or a pharmaceutically acceptable salt thereof, wherein $R^c$ is as originally described.

Another subembodiment of the invention of formula IV is realized when $R^c$ is selected from the group consisting of hydrogen, halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR))_nC_{3-10}$ cycloalkyl, —C(O)$C_{1-6}$alkyl, —C(O)$C_{3-10}$cycloalkyl), —C(O)$C_{3-10}$heterocyclyl, said alkyl, cycloalkyl, aryl and heterocyclyl optionally substituted with 1 to 4 groups of $R^b$. Yet another subembodiment of the invention of formula II is realized when $R^c$ is selected from the group consisting of hydrogen, $CH_3$, $CH_2CH_3$, —$(CH_2)_3CH_3$, $CH_2CH(CH_3)_2$, $C(CH_3)_2CH_2CH_3$, $(CH_2)_nOCH_3$, $CH_2CF_2CF_3$, $(CH_2)_nCF_3$, halogen, $(CH_2) CH(CF_3)_2$, $CH_2CHF_2$, $C(CH_3)_2C≡C$, —$(CH_2)_nN(R)_2$, OH, C(O)cyclopropyl, $(CHR)_n$cyclopropyl, (CHR)$_n$pyridyl, (CHR)$_n$tetrahydropyranyl, (CHR)$_n$cyclobutyl, (CHR)$_n$thiadiazolyl, (CHR)$_n$oxetanyl, (CHR)$_n$cyclopentyl, (CHR)$_n$cyclohexyl, (CHR)$_n$phenyl, (CHR)$_n$thiazolyl, C(O)phenyl, C(O)pyridyl, C(O)C(CH$_3$)$_2$F, C(O)oxazolyl, C(O)C(CH$_3$)$_3$, C(O)thiophenyl, SO$_2$phenyl, (CHR)$_n$cyclopentyl, (CHR)$_n$morpholinyl, and (CHR)$_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of R$^b$. A subembodiment of the invention of formula II is realized when R$^{3a}$ is (i). Another subembodiment of the invention of formula II is realized when R$^{3a}$ is (ii). Still another subembodiment of the invention of formula II is realized when R$^{3a}$ is (iii). Another embodiment of the invention of formula IV is realized when R$^{3c}$ is (a1). Another embodiment of the invention of formula IV is realized when R$^{3b}$ is (a2). Another embodiment of the invention of formula IV is realized when R$^{3b}$ is (a3).

Yet another embodiment of the invention of formula I is realized when R$^3$ is optionally substituted C$_{3-10}$ cycloalkyl. A subembodiment of this aspect of the invention is realized when R$^3$ is selected from the group consisting of optionally substituted cyclohexyl, cyclobutyl, cyclopropyl, and cyclopentyl. Another aspect of the invention is realized when the cycloalkyl of R$^3$ is unsubstituted or substituted cyclohexyl. Another aspect of the invention is realized when the cycloalkyl of R$^3$ is unsubstituted or substituted cyclobutyl. Another aspect of the invention is realized when the cycloalkyl of R$^3$ is unsubstituted or substituted cyclopropyl. Another aspect of the invention is realized when the cycloalkyl of R$^3$ is unsubstituted or substituted cyclopentyl.

Examples of the compounds of this invention include examples 1-57 which are found in the General Schemes and Examples section of this application, including those in Tables 1-5 herein.

As used herein, unless otherwise specified, the term "A$_{2a}$ receptor antagonist" (equivalently, A$_{2a}$ antagonist) means a compound exhibiting a potency of less than about 1 µM when assayed in accordance with the procedure described herein. Preferred compounds exhibit at least 100-fold selectivity for antagonizing the A$_{2a}$ receptor over any other andenosine receptor (e.g., A$_1$, A$_{2b}$, or A$_3$).

Compounds of the invention and formulations comprising compounds of the invention are believed to be useful in providing potential treatment, management, alleviation or amelioration of conditions or disease states which can be treated, managed, alleviated or ameliorated by specific antagonism of A2a receptors. Conditions for which such therapy may be provided include, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential, or are believed to have the potential, for use in preventing or lessening the effect of drugs that cause movement disorders As described herein, unless otherwise indicated, the use of a compound in treatment means that an amount of the compound, generally presented as a component of a formulation that comprises other excipients, is administered in aliquots of an amount, and at time intervals, which provides and maintains at least a therapeutic serum level of at least one pharmaceutically active form of the compound over the time interval between dose administration.

Absolute stereochemistry is illustrated by the use of hashed and solid wedge bonds. As shown in Illus-I and Illus-II. Accordingly, the methyl group of Illus-I is emerging from the page of the paper and the ethyl group in Illus-II is descending into the page, where the cyclohexene ring resides within the plane of the paper. It is assumed that the hydrogen on the same carbon as the methyl group of Illus-I descends into the page and the hydrogen on the same carbon as the ethyl group of Illus-II emerges from the page. The convention is the same where both a hashed and solid rectangle are appended to the same carbon as in Illus-III, the Methyl group is emerging from the plane of the paper and the ethyl group is descending into the plane of the paper with the cyclohexene ring in the plane of the paper.

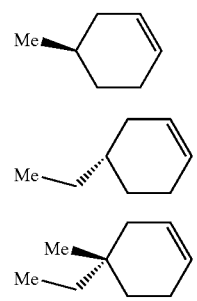

Illus-I

Illus-2

Illus-3

As is conventional, unless otherwise noted in accompanying text, ordinary "stick" bonds or "wavy" bonds indicate that all possible stereochemistry is represented, including, pure compounds, mixtures of isomers, and racemic mixtures.

As used herein, unless otherwise specified, the following terms have the following meanings:

The phrase "at least one" used in reference to the number of components comprising a composition, for example, "at least one pharmaceutical excipient" means that one member of the specified group is present in the composition, and more than one may additionally be present. Components of a composition are typically aliquots of isolated pure material added to the composition, where the purity level of the isolated material added into the composition is the normally accepted purity level for a reagent of the type.

"at least one" used in reference to substituents on a compound or moiety appended to the core structure of a compound means that one substituent of the group of substituents specified is present, and more than one substituent may be bonded to any of the chemically accessible bonding points of the core.

Whether used in reference to a substituent on a compound or a component of a pharmaceutical composition the phrase "one or more", means the same as "at least one";

"concurrently" and "contemporaneously" both include in their meaning (1) simultaneously in time (e.g., at the same time); and (2) at different times but within the course of a common treatment schedule;

"consecutively" means one following the other;

"sequentially" refers to a series administration of therapeutic agents that awaits a period of efficacy to transpire between administering each additional agent; this to say that after administration of one component, the next component is administered after an effective time period after the first component; the effective time period is the amount of time given for realization of a benefit from the administration of the first component;

"effective amount" or "therapeutically effective amount" is meant to describe the provision of an amount of at least one compound of the invention or of a composition comprising at least one compound of the invention which is effective in treating or inhibiting a disease or condition described herein, and thus produce the desired therapeutic, ameliorative, inhibitory or preventative effect. For example, in treating central nervous system diseases or disorders with one or more of the compounds described herein "effective amount" (or "therapeutically effective amount") means, for example, providing the amount of at least one compound of Formula A that results in a therapeutic response in a patient afflicted with a central nervous system disease or disorder ("condition"), including a response suitable to manage, alleviate, ameliorate, or treat the condition or alleviate, ameliorate, reduce, or eradicate one or more symptoms attributed to the condition and/or long-term stabilization of the condition, for example, as may be determined by the analysis of pharmacodynamic markers or clinical evaluation of patients afflicted with the condition;

"patient" and "subject" means an animal, such as a mammal (e.g., a human being) and is preferably a human being;

"prodrug" means compounds that are rapidly transformed, for example, by hydrolysis in blood, in vivo to the parent compound, e.g., conversion of a prodrug of Formula A to a compound of Formula A, or to a salt thereof, a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes prodrugs of the novel compounds of this invention;

The term "substituted" means that one or more of the enumerated substituents can occupy one or more of the bonding positions on the substrate typically occupied by "—H", provided that such substitution does not exceed the normal valency rules for the atom in the bonding configuration presented in the substrate, and that the substitution ultimately provides a stable compound, which is to say that such substitution does not provide compounds with mutually reactive substituents located geminal or vicinal to each other; and wherein the substitution provides a compound sufficiently robust to survive isolation to a useful degree of purity from a reaction mixture.

Where optional substitution of a moiety is described (e.g. "optionally substituted") the term means that if substituents are present, one or more of the enumerated (or default substituents for the specified substrate, for example, hydrogen on an alkyl or aromatic moiety) can be present on the substrate in a bonding position normally occupied by the default substituent, for example, a hydrogen atom, in accordance with the definition of "substituted" presented herein.

As used herein, unless otherwise specified, the following terms used to describe moieties, whether comprising the entire definition of a variable portion of a structural representation of a compound of the invention or a substituent appended to a variable portion of a structural representation of a group of compounds of the invention have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl moieties, and the like); moieties are equivalently described herein by structure, typographical representation or chemical terminology without intending any differentiation in meaning, for example, the chemical term "acyl", defined below, is equivalently described herein by the term itself, or by typographical representations "R'—(C=O)—" or "R'—C(O)—", or by the structural representation:

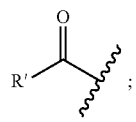

"alkyl" (including the alkyl portions of other moieties, such as trifluoromethyl-alkyl- and alkoxy-) means an aliphatic hydrocarbon moiety comprising up to about 20 carbon atoms (for example, a designation of "$C_{1-20}$-alkyl" indicates an aliphatic hydrocarbon moiety of from 1 to 20 carbon atoms). In some embodiments, alkyls preferably comprise up to about 10 carbon atoms, unless the term is modified by an indication that a shorter chain is contemplated, for example, an alkyl moiety of from 1 up to 8 carbon atoms is designated herein "$C_{1-8}$-alkyl". The term "alkyl" is further defined by "Linear", or "Branched". Where the term "alkyl" is indicated with two hyphens (i.e., "-alkyl-" it indicates that the alkyl moiety is bonded in a manner that the alkyl moiety connects the substituents on either side of it, for example, "-alkyl-OH" indicates an alkyl moiety connecting a hydroxyl moiety to a substrate.

The term "linear-alkyl" includes alkyl moieties which comprise a hydrocarbon chain with no aliphatic hydrocarbon "branches" appended to it, although other substituents may replace a C—H bond on the hydrocarbon chain. Examples of linear alkyl include, but are not limited to, methyl-, ethyl-, n-propyl-, n-butyl-, n-pentyl- or n-hexyl-.

The term "branched-alkyl" is a moiety comprising a main hydrocarbon chain of up to the maximum specified number of carbon atoms with a lower-alkyl chain appended to one or more of the carbon atoms comprising, but not terminating, the main hydrocarbon chain. A branched alkyl moiety therefore comprises at least 3 carbon atoms in the main chain. Examples of branched alkyl moieties include, but are not limited to, t-butyl-, neopentyl-, or 2-methyl-4-ethyl-hexyl- The term "cyclic-alkyl" (equivalently "cycloalkyl") means a moiety having a main hydrocarbon chain forming a cyclic aliphatic moiety comprising at least 3 carbon atoms (the minimum number necessary to provide a cyclic moiety) up to the maximum number of specified carbon atoms. Examples of cycloalkyl moieties include, but are not limited to, cyclopropyl, cyclobutyl, cyclopentyl or cyclohexyl. The term cyclic-alkyl (equivalently "cycloalkyl") also includes non-aromatic, fused multicyclic ring system comprising up to about 20 carbon atoms which may optionally be substituted as defined herein for "alkyl" generally. Suitable multicyclic cycloalkyls are, for example, but are not limited to: 1-decalin; norbornyl; adamantyl; and the like;

Any of the afore-mentioned linear-, branched-, or cycloalkyl moieties which are defined to be "optionally substituted" means that one or more of the carbon atoms in the structure can have one or more of the C—H bonds associated therewith substituted with a substituent selected from the list of substituents called out in the definition of the moiety.

"lower alkyl" means a linear, branched, or cycloalkyl moiety comprising up to about 6 carbon atoms; non-limiting examples of suitable lower alkyl groups include methyl, ethyl, n-propyl, isopropyl, cyclopropyl, n-butyl, t-butyl, cyclobutyl, n-pentyl, isopentyl, neopentyl, cyclopentyl, n-hexyl, cyclohexyl and the like;

"aryl" (sometimes abbreviated "ar") means an aromatic monocyclic or multicyclic ring system comprising about 6 to about 14 carbon atoms (denoted herein also as "$C_{6-14}$-aryl"), preferably about 6 to about 10 carbon atoms ("$C_{6-10}$-aryl"); the aryl group can be optionally substituted with one or more independently selected "ring system substituents" (defined below). Non-limiting examples of suitable aryl groups include phenyl

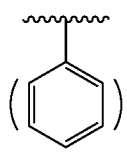

and naphthyl

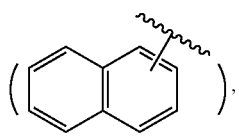

wherein bonding can be through any of the carbons in the aromatic ring, and wherein any ring carbon atoms not participating in a bond to the substrate may have bonded to it a substituent other than —H, independently selected in each instance from the list of "ring-system substituents" defined herein, or as defined in each instance where the term is used in conjunction with an enumerated list of substituents;

"halogen" means fluorine, chlorine, bromine, or iodine; preferred halogens, unless specified otherwise where the term is used, are fluorine, chlorine and bromine, a substituent which is a halogen atom means —F, —Cl, —Br, or —I, and "halo" means fluoro, chloro, bromo, or iodo substituents bonded to the moiety defined, for example, "haloalkyl" means an alkyl, as defined above, wherein one or more of the bonding positions on the alkyl moiety typically occupied by hydrogen atoms are instead occupied by a halo group, perhaloalkyl (or "fully halogenated" alkyl) means that all bonding positions not participating in bonding the alkyl substituent to a substrate are occupied by a halogen, for example, where the alkyl is selected to be methyl, the term perfluoroalkyl means —$CF_3$;

"heterocyclyl", "heterocycle" or "heterocyclic", represents a stable 5- to 7-membered monocyclic or stable 8- to 11-membered bicyclic heterocyclic ring which is either saturated, partially saturated, or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. The term heterocyclyl, heterocycle or heterocyclic includes heteroaryl moieties. The nitrogen or sulfur atom of the heterocyclyl can be optionally oxidized to the corresponding N-oxide, S-oxide or S,S-dioxide ($SO_2$). Non-limiting examples of suitable unsaturated monocyclic heterocyclyl rings include piperidyl, pyrrolidinyl, piperazinyl, morpholinyl-

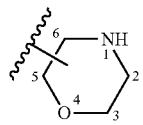

(where unless otherwise noted the moiety is bonded to the substrate through any of ring carbon atoms $C_2$, $C_3$, $C_5$, or $C_6$), thiomorpholinyl, thiazolidinyl, 1,3-dioxolanyl, 1,4-dioxanyl, tetrahydrofuranyl, tetrahydrothiophenyl, tetrahydrothiopyranyl, and the like; and polycyclicheterocyclyl compounds, for example, moieties of the structure:

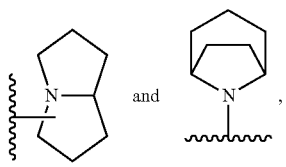

and the like. Other examples of saturated, partially saturated and unsaturated heterocyclic elements include, but are not limited to, azepinyl, benzodioxolyl, benzimidazolyl, benzisoxazolyl, benzofurazanyl, benzopyranyl, benzothiopyranyl, benzofuryl, benzothiazolyl, benzothienyl, benzotriazolyly, benzoxazolyl, chromanyl, cinnolinyl, dihydrobenzofuryl, dihydrobenzothienyl, dihydrobenzothiopyranyl, dihydrobenzothiopyranyl sulfone, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, naphthyridinyl, oxadiazolyl, 2-oxoazepinyl, oxazolyl, 2-oxopiperazinyl, 2-oxopiperdinyl, 2-oxopyrrolidinyl, pyridyl, pyrazinyl, pyrazolidinyl, pyrazolyl, pyrazolopyridinyl, pyridazinyl, pyrimidinyl, pyrrolyl, quinazolinyl, quinolinyl, quinoxalinyl, tetrahydroisoquinolinyl, tetrahydroquinolinyl, thiamorpholinyl, thiamorpholinyl sulfoxide, thiazolyl, thienofuryl, thienothienyl, thienyl, triazolyl, N-oxides and —C═O derivatives thereof.

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; the "heteroaryl" can be optionally substituted at chemically available ring atoms by one or more independently selected "ring system substituents" (defined below); the prefix aza, azo, oxa, oxo, thia or thio before the heteroaryl root name means that at least a nitrogen, oxygen or sulfur atom, respectively, is present as a ring atom, and in some embodiments 2 or more heteroatoms are present in a ring, for example, a pyrazole or a thiazole moiety; a nitrogen atom of a heteroaryl can be optionally oxidized to the corresponding N-oxide; non-limiting examples of heteroaryl moieties include: pyridyl-,

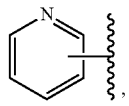

thiophenyl-,

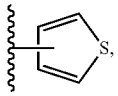

furanyl-,

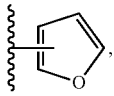

pyrazinyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, furopyridine, and, for example, heteroaryl moieties of the following structure:

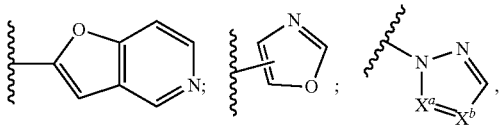

where one of $X^a$ or $X^b$ is —CH= or —N= and the other is —CH=;

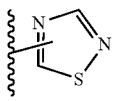

and the like (wherein, unless otherwise noted, bonded to the substrate through any available ring atom that results in a stable bonding arrangement);

"hydroxyl moiety" and "hydroxy" means an HO— group, "hydroxyalkyl" means a substituent of the formula: "HO-alkyl-", wherein the alkyl group is bonded to the substrate and may be substituted or unsubstituted as defined above; preferred hydroxyalkyl moieties comprise a lower alkyl; Non-limiting examples of suitable hydroxyalkyl groups include hydroxymethyl and 2-hydroxyethyl; and bonding sequence is indicated by hyphens where moieties are represented in text, for example -alkyl, indicates a single bond between a substrate and an alkyl moiety, -alkyl-X, indicates that an alkyl group bonds an "X" substituent to a substrate, and in structural representation bonding sequence is indicated by a wavy line terminating a bond representation, for example:

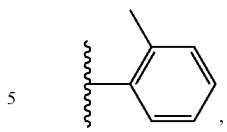

indicates that the methylphenyl moiety is bonded to a substrate through a carbon atom ortho to the methyl substituent, while a bond representation terminated with a wavy line and drawn into a structure without any particular indication of an atom to which it is bonded indicates that the moiety may be bonded to a substrate via any of the atoms in the moiety which are available for bonding as described in the examples above.

Unsatisfied valences in the text, schemes, examples, structural formulae, and any Tables herein is assumed to have a hydrogen atom or atoms of sufficient number to satisfy the valences.

One or more compounds of the invention may also exist as, or optionally be converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, and hemisolvate, including hydrates (where the solvent is water or aqueous-based) and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (for example, an organic solvent, an aqueous solvent, water or mixtures of two or more thereof) at a higher than ambient temperature, and cooling the solution, with or without an antisolvent present, at a rate sufficient to form crystals which are then isolated by standard methods. Analytical techniques such as, for example I.R. spectroscopy, show the presence of the solvent (including water) in the crystals as a solvate (or hydrate in the case where water is incorporated into the crystalline form).

The term "pharmaceutical composition" as used herein encompasses both the bulk composition and individual dosage units comprised of more than one (e.g., two) pharmaceutically active agents such as, for example, a compound of the present invention and an additional agent as described herein, along with any pharmaceutically inactive excipients. As will be appreciated by the ordinarily skilled artisan, excipients are any constituent which adapts the composition to a particular route of administration or aids the processing of a composition into a dosage form without itself exerting an active pharmaceutical effect. The bulk composition and each individual dosage unit can contain fixed amounts of the afore-said "more than one pharmaceutically active agents". The bulk composition is material that has not yet been formed into individual dosage units.

This invention also includes the compounds of this invention in isolated and purified form obtained by routine techniques. Polymorphic forms of the compounds of Formula A, and of the salts, solvates and prodrugs of the compounds of Formula A, are intended to be included in the present invention. Certain compounds of the invention may exist in different isomeric forms (e.g., enantiomers, diastereoisomers, atropisomers). The inventive compounds include all isomeric forms thereof, both in pure form and admixtures of two or more, including racemic mixtures.

In the same manner, unless indicated otherwise, presenting a structural representation of any tautomeric form of a compound which exhibits tautomerism is meant to include all such tautomeric forms of the compound. Accordingly, where compounds of the invention, their salts, and solvates and prodrugs thereof, may exist in different tautomeric forms or in equilibrium among such forms, all such forms of the compound are embraced by, and included within the scope of the invention. Examples of such tautomers include, but are not limited to, ketone/enol tautomeric forms, imine-enamine tautomeric forms, and for example heteroaromatic forms such as the following moieties:

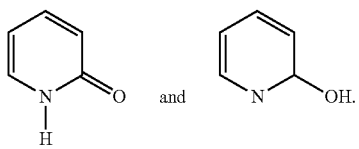 [SMILES: O=c1cccc[nH]1 ; OC1C=CC=CN1]

All stereoisomers of the compounds of the invention (including salts and solvates of the inventive compounds and their prodrugs), such as those which may exist due to asymmetric carbons present in a compound of the invention, and including enantiomeric forms (which may exist even in the absence of asymmetric carbons), rotameric forms, atropisomers, and diastereomeric forms, are contemplated within the scope of this invention. Individual stereoisomers of the compounds of the invention may be isolated in a pure form, for example, substantially free of other isomers, or may be isolated as an admixture of two or more stereoisomers or as a racemate. The chiral centers of the present invention can have the S or R configuration as defined by the IUPAC 1974 Recommendations. The use of the terms "salt", "solvate" "prodrug" and the like, is intended to equally apply to salts, solvates and prodrugs of isolated enantiomers, stereoisomer pairs or groups, rotamers, tautomers, or racemates of the inventive compounds.

Where diastereomeric mixtures can be separated into their individual diastereomers on the basis of their physical chemical differences by known methods, for example, by chiral chromatography and/or fractional crystallization, simple structural representation of the compound contemplates all diastereomers of the compound. As is known, enantiomers may also be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individually isolated diastereomers to the corresponding purified enantiomers.

As the term is employed herein, salts of the inventive compounds, whether acidic salts formed with inorganic and/or organic acids, basic salts formed with inorganic and/or organic bases, salts formed which include zwitterionic character, for example, where a compound contains both a basic moiety, for example, but not limited to, a nitrogen atom, for example, an amine, pyridine or imidazole, and an acidic moiety, for example, but not limited to a carboxylic acid, are included in the scope of the inventive compounds described herein. The formation of pharmaceutically useful salts from basic (or acidic) pharmaceutical compounds are discussed, for example, by S. Berge et al., Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; in The Orange Book (Food & Drug Administration, Washington, D.C. on their website); and P. Heinrich Stahl, Camille G. Wermuth (Eds.), Handbook of Pharmaceutical Salts: Properties, Selection, and Use, (2002) Int'l. Union of Pure and Applied Chemistry, pp. 330-331. These disclosures are incorporated herein by reference.

The present invention contemplates all available salts, including salts which are generally recognized as safe for use in preparing pharmaceutical formulations and those which may be formed presently within the ordinary skill in the art and are later classified as being "generally recognized as safe" for use in the preparation of pharmaceutical formulations, termed herein as "pharmaceutically acceptable salts". Examples of pharmaceutically acceptable acid addition salts include, but are not limited to, acetates, including trifluoroacetate salts, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Examples of pharmaceutically acceptable basic salts include, but are not limited to, ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be converted to an ammonium ion or quartemized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, and in sufficient purity to be characterized by standard analytical techniques described herein or well known to the skilled artisan.

A functional group in a compound termed "protected" means that the group is in modified form to preclude undesired side reactions at the protected site when the compound is subjected to a reaction. Suitable protecting groups are known, for example, as by reference to standard textbooks, for example, T. W. Greene et al, Protective Groups in organic Synthesis (1991), Wiley, New York.

When a variable (e.g., aryl, heterocycl, $R^{XY}$, etc.) appears more than once in any moiety or in any compound of the invention, the selection of moieties defining that variable for each occurrence is independent of its definition at every other occurrence unless specified otherwise in the local variable definition.

As used herein, the term "composition" is intended to encompass a product comprising the specified ingredients in the specified amounts, and any product which results, directly or indirectly, from combination of the specified ingredients in the specified amounts.

The present invention also embraces isotopically-labeled compounds of the present invention which are structurally identical to those recited herein, but for the fact that a statistically significant percentage of one or more atoms in that form of the compound are replaced by an atom having an atomic mass or mass number different from the atomic mass or mass number of the most abundant isotope usually found in nature, thus altering the naturally occurring abundance of that isotope present in a compound of the invention. Examples of isotopes that can be preferentially incorporated into compounds of the invention include isotopes of hydrogen, carbon, nitrogen, oxygen, phosphorus, iodine, fluorine and chlorine, for example, but not limited to: $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{18}F$, and $^{36}Cl$, $^{123}I$ and $^{125}I$. It will be appreciated that other isotopes may be incorporated by know means also.

Certain isotopically-labeled compounds of the invention (e.g., those labeled with $^3H$, $^{11}C$ and $^{14}C$) are recognized as being particularly useful in compound and/or substrate tissue distribution assays using a variety of known techniques. Tritiated (i.e., $^3H$) and carbon-14 (i.e., $^{14}C$) isotopes are particularly preferred for their ease of preparation and detection. Further, substitution of a naturally abundant isotope with a heavier isotope, for example, substitution of protium with deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the reaction Schemes and/or in the Examples herein below, by substituting an appropriate isotopically labeled reagent for a non-isotopically labeled reagent, or by well-known reactions of an appropriately prepared precursor to the compound of the invention which is specifically prepared for such a "labeling" reaction. Such compounds are included also in the present invention.

In one aspect, as mentioned above, the present invention provides pharmaceutical formulations (pharmaceutical compositions) for use in antagonizing $A_{2A}$ receptors, believed to be useful in treating central nervous system (CNS) disorders, for example, movement disorders associated with Parkinson's disease or the treatment thereof, wherein the compositions comprising at least one compound, or pharmaceutically acceptable salt thereof, of Formula I or Formula II, as defined herein.

As mentioned above, in one aspect the invention provides pharmaceutical formulations (pharmaceutical compositions) suitable for use in blocking adenosine A2a receptors found in the basal ganglia, comprising at least one compound of Formula I or Formula II presented above, or a pharmaceutically acceptable salt thereof, and at least one pharmaceutically acceptable carrier (described below). It will be appreciated that pharmaceutically formulations of the invention may comprise more than one compound of the invention, for example, the combination of two or three compounds of the invention, each present by adding to the formulation the desired amount of the compound in a pharmaceutically acceptably pure form. It will be appreciated that compositions of the invention may comprise, in addition to one or more of compounds of the invention, one or more other compounds which also have pharmacological activity, for example, as described herein below.

In some embodiments the formulation preferably comprises one or more compounds of Formulas I-IV, as defined herein, and at least one pharmaceutically acceptable carrier (described below). It will be appreciated that pharmaceutically formulations of the invention may comprise more than one compound of the invention, for example, the combination of two or three compounds of Formulas I-IV, each present by adding to the formulation the desired amount of the compound in a pharmaceutically acceptably pure form. It will be appreciated that compositions of the invention may comprise, in addition to one or more of the compounds of the invention, one or more additional compounds which also have pharmacological activity, for example, as described herein below.

While formulations of the invention may be employed in bulk form, it will be appreciated that for most applications the inventive formulations will be incorporated into a dosage form suitable for administration to a patient, each dosage form comprising an amount of the selected formulation which contains an effective amount of said one or more compounds of Formula I. Examples of suitable dosage forms include, but are not limited to, dosage forms adapted for: (i) oral administration, e.g., a liquid, gel, powder, solid or semi-solid pharmaceutical composition which is loaded into a capsule or pressed into a tablet and may comprise additionally one or more coatings which modify its release properties, for example, coatings which impart delayed release or formulations which have extended release properties; (ii) a dosage form adapted for intramuscular administration (IM), for example, an injectable solution or suspension, and which may be adapted to form a depot having extended release properties; (iii) a dosage form adapted for intravenous administration (IV), for example, a solution or suspension, for example, as an IV solution or a concentrate to be injected into a saline IV bag; (iv) a dosage form adapted for administration through tissues of the oral cavity, for example, a rapidly dissolving tablet, a lozenge, a solution, a gel, a sachets or a needle array suitable for providing intramucosal administration; (v) a dosage form adapted for administration via the mucosa of the nasal or upper respiratory cavity, for example a solution, suspension or emulsion formulation for dispersion in the nose or airway; (vi) a dosage form adapted for transdermal administration, for example, a patch, cream or gel; (vii) a dosage form adapted for intradermal administration, for example, a microneedle array; and (viii) a dosage form adapted for delivery via rectal or vaginal mucosa, for example, a suppository.

For preparing pharmaceutical compositions containing compounds of the invention, generally the compounds of the invention will be combined with one or more pharmaceutically acceptable excipients. These excipients impart to the composition properties which make it easier to handle or process, for example, lubricants or pressing aids in powdered medicaments intended to be tableted, or adapt the formulation to a desired route of administration, for example, excipients which provide a formulation for oral administration, for example, via absorption from the gastrointestinal tract, transdermal or transmucosal administration, for example, via adhesive skin "patch" or buccal administration, or injection, for example, intramuscular or intravenous, routes of administration. These excipients are collectively termed herein "a carrier". Typically formulations may comprise up to about 95 percent active ingredient, although formulations with greater amounts may be prepared.

Pharmaceutical compositions can be solid, semi-solid or liquid. Solid form preparations can be adapted to a variety of modes of administration, examples of which include, but are not limited to, powders, dispersible granules, mini-tablets, beads, which can be used, for example, for tableting, encapsulation, or direct administration. Liquid form preparations include, but are not limited to, solutions, suspensions and emulsions which for example, but not exclusively, can be employed in the preparation of formulations intended for parenteral injection, for intranasal administration, or for administration to some other mucosal membrane. Formulations prepared for administration to various mucosal membranes may also include additional components adapting them for such administration, for example, viscosity modifiers.

Aerosol preparations, for example, suitable for administration via inhalation or via nasal mucosa, may include solutions and solids in powder form, which may be in combination with a pharmaceutically acceptable propellant, for example, an inert compressed gas, e.g. nitrogen. Also included are solid form preparations which are intended to be converted, shortly before use, to a suspension or a solution, for example, for oral or parenteral administration. Examples of such solid forms include, but are not limited to, freeze dried formulations and liquid formulations adsorbed into a solid absorbent medium.

The compounds of the invention may also be deliverable transdermally or transmucosally, for example, from a liquid, suppository, cream, foam, gel, or rapidly dissolving solid form. It will be appreciated that transdermal compositions can take also the form of creams, lotions, aerosols and/or emulsions and can be provided in a unit dosage form which includes a transdermal patch of any know in the art, for example, a patch which incorporates either a matrix comprising the pharmaceutically active compound or a reservoir which comprises a solid or liquid form of the pharmaceutically active compound.

Examples of pharmaceutically acceptable carriers and methods of manufacture for various compositions mentioned above may be found in A. Gennaro (ed.), Remington: The Science and Practice of Pharmacy, 20$^{th}$ Edition, (2000), Lippincott Williams & Wilkins, Baltimore, Md.

Preferably, the pharmaceutical preparation is in a unit dosage form. In such form, the preparations subdivided into suitably sized unit doses containing appropriate quantities of the active component, e.g., an effective amount to achieve the desired purpose.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

In another embodiment the present invention provides for use of the compounds described herein for the potential treatment, management, alleviation or amelioration of conditions or disease states which can be, or are believed to be, treated, managed, alleviated or ameliorated by specific antagonism of adenosine A2a receptors, for example, central nervous system diseases or disorders, including but not limited to the treatment of movement disorders (e.g., tremors, bradykinesias, gait, dystonias, dyskinesias, tardive dyskinesias, other extrapyramidal syndromes, Parkinson's disease and disorders associated with Parkinson's disease). The compounds of the invention also have the potential for use in preventing or lessening the effect of drugs that cause movement disorders.

In accordance with the present invention, antagonism of adenosine A2a receptors is accomplished by administering to a patient in need of such therapy an effective amount of one or more compounds of the invention, or a pharmaceutically acceptable salt thereof.

In some embodiments it is preferred for the compound to be administered in the form of a pharmaceutical composition comprising the compound of the invention, for example, a compound of Formula I or Formula II, or a salt of either thereof, and at least one pharmaceutically acceptable carrier. It will be appreciated that pharmaceutically formulations of the invention may comprise more than one compound of the invention, or a salt thereof, for example, the combination of two or three compounds of the invention, each present by adding to the formulation the desired amount of the compound or a salt thereof which has been isolated in a pharmaceutically acceptably pure form.

As mentioned above, administration of a compound of the invention to effect antagonism of $A_{2a}$ receptor sites, which is believed to be beneficial in the treatment of central nervous system diseases is preferably accomplished by incorporating the compound into a pharmaceutical formulation incorporated into a dosage form, for example, one of the above-described dosage forms comprising an effective amount of at least one compound of the invention (e.g., 1, 2 or 3, or 1 or 2, or 1, and usually 1 compound of the invention), or a pharmaceutically acceptable salt thereof. Methods for determining safe and effective administration of compounds which are pharmaceutically active, for example, a compound of the invention, are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), or the Physician's Desk Reference, 57$^{th}$ Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the invention can be administered at a total daily dosage of up to 1,000 mg, which can be administered in one daily dose or can be divided into multiple doses per 24 hour period, for example, two to four doses per day.

As mentioned above, administration of a compound of the invention is preferably accomplished by incorporating the compound into a pharmaceutical formulation incorporated into a dosage form, for example, one of the above-described dosage forms comprising an effective amount of at least one compound of the invention (for example, 1, 2 or 3, or 1 or 2, or 1, and usually 1 compound of the invention), or a pharmaceutically acceptable salt thereof. Methods for determining safe and effective administration of compounds which are pharmaceutically active are known to those skilled in the art, for example, as described in the standard literature, for example, as described in the "Physicians' Desk Reference" (PDR), e.g., 1996 edition (Medical Economics Company, Montvale, N.J. 07645-1742, USA), the Physician's Desk Reference, 56th Edition, 2002 (published by Medical Economics company, Inc. Montvale, N.J. 07645-1742), or the Physician's Desk Reference, 57th Edition, 2003 (published by Thompson PDR, Montvale, N.J. 07645-1742); the disclosures of which is incorporated herein by reference thereto. The amount and frequency of administration of the compounds of the invention and/or the pharmaceutically acceptable salts thereof will be regulated according to the judgment of the attending clinician considering such factors as age, condition and size of the patient as well as severity of the symptoms being treated. Compounds of the instant invention can be administered at a total daily dosage of up to 1,000 mg, which can be administered in one daily dose or can be divided into two to four doses per day.

In general, in what ever form administered, the dosage form administered will contain an amount of at least one compound of the invention, or a salt thereof, which will provide a therapeutically effective serum level of the compound in some form for a period of at least 2 hours, preferably at least four hours, and preferably longer. In general, as is known in the art, dosages of a pharmaceutical composition providing a therapeutically effective serum level of a compound of the invention can be spaced in time to provide serum level meeting or exceeding the minimum therapeutically effective serum level on a continuous basis throughout the period during which treatment is administered. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. As will be appreciated the dosage form administered may also be in a form providing an extended release period for the pharmaceutically active compound which will provide a therapeutic serum level for a longer period, necessitating less frequent dosage intervals. As mentioned above, a composition of the invention can incorporate additional pharmaceutically active components or be administered simultaneously, contemporaneously, or sequentially with other pharmaceutically active compositions as may be additionally needed in the course of providing treatment. Such additional therapeutic agents can include compounds with dopaminergic activity, for example, i) L-DOPA; ii) DOPA decarboxylase inghibitors; and iii) COMT inhibitors.

Those skilled in the art will appreciate that treatment protocols utilizing at least one compound of the invention can be varied according to the needs of the patient. Thus, compounds of the invention used in the methods of the invention can be administered in variations of the protocols described above. For example, compounds of the invention can be administered discontinuously rather than continuously during the treatment cycle.

In the examples that follow certain of the exemplified compounds are prepared as pure enantiomers, or prepared from enantiopure precursors, or are isolated using chiral separation methods after synthesis, for example, chiral chromatography. After isolation of chiral compounds the absolute stereochemistry of the isolated compound was not determined in every example. Accordingly, where pure isomers have been prepared but the absolute configuration has not been verified, the enantiomer isolated in pure form is specified by the following convention.

Unless indicated otherwise in the text, where present, isomers of example compounds were not separated. Unless indicated otherwise in the text, where isomers were separated into fractions containing an excess of a particular isomer, for example, a fraction containing an excess of an optical isomer, which separation may be accomplished, for example, by super critical fluid chromatography, absolute stereochemistry of separated isomers was not determined unless indicated otherwise.

Where a reaction scheme appearing in an example employs a compound having one or more stereocenters, the stereocenters are indicated with an asterisk, as shown below in illustration compound Def-1.

Def-1

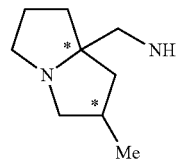

Accordingly, Def-1 consists of the following pairs of isomers: (i) Trans-isomers ((2R,7aS)-2-methylhexahydro-1H-pyrrolizin-7a-yl)methanamine (Compound ABC-1) and ((2S,7aR)-2-methylhexahydro-1H-pyrrolizin-7a-yl)methanamine (Compound ABC-2); and (ii) Cis-isomers ((2R,7aR)-2-methylhexahydro-1H-pyrrolizin-7a-yl)methanamine (Compound ABC-3) and ((2S,7aS)-2-methylhexahydro-1H-pyrrolizin-7a-yl)methanamine (Compound ABC-4).

ABC-1

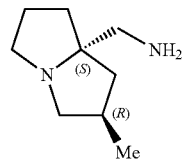

ABC-2

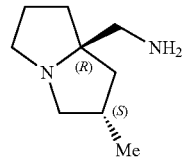

ABC-3

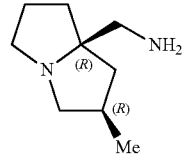

ABC-4

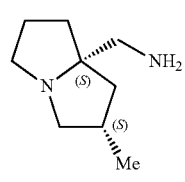

When the compound is prepared and separated into pure enantiomers, albeit without determining the absolute configuration of each enantiomer of the compound, the product will be identified in the title using both enantiomer names, e.g., where ABC-1 and ABC-2 are prepared and separated into pure enantiomers, the title will read "preparation of ((2R,7aS)-2-methylhexahydro-1H-pyrrolizin-7a-yl)methanamine and ((2S,7aR)-2-methylhexahydro-1H-pyrrolizin-7a-yl)methanamine. In some instances where enantiomeric compounds are prepared the designation (Cis) or (Trans) may be appended to the name to clarify the relationship of the stereo centers present in the two stereoisomers. As will be appreciated, identification of each product in the experimental preparation as "ABC-enantiomer A" or "ABC-enantiomer B" is not an association of the enantiomer prepared and isolated with any stereospecific name, only that both said enantiomers were prepared and isolated in increased enantiopurity without determination of the absolute configuration of either compound thus prepared.

Where isomeric compounds are prepared in a racemic mixture, asterisks will be inserted into the structural representation to indicate the stereocenters, but the title will reference the preparation of both enantiomers, e.g., where ABC-3 and ABC-4 are prepared as a racemate, the title will read "preparation of ((2R,7aR and 2S,7aS)-2-methylhexahydro-1H-pyrrolizin-7a-yl)methanamine".

Those skilled in the art will appreciate that treatment protocols utilizing at least one compound of the invention, as described herein, may be varied according to the needs of the patient. Thus, compounds of the invention used in the methods of this invention may be administered in variations of the protocols described above. For example, the compounds of this invention may be administered discontinuously rather than continuously during the treatment cycle.

The following examples are presented to further illustrate compounds of the invention, but, with reference to the general formula presented above, they are not presented as limiting the invention to these specifically exemplified compounds. The starting materials are either commercially available or may be prepared from commercially available reagents using conventional reactions well known in the art.

SCHEME A

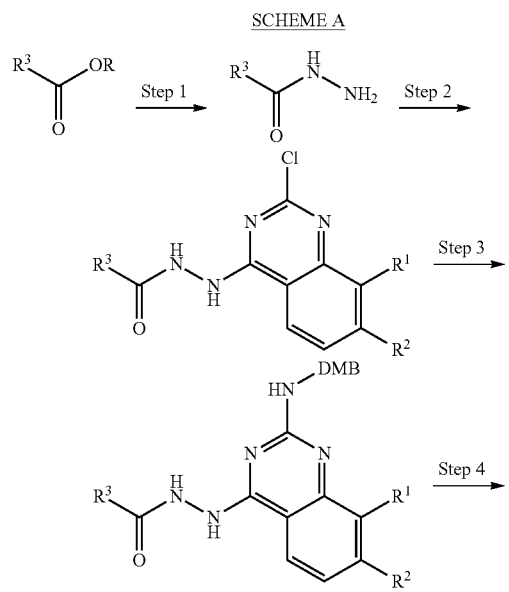

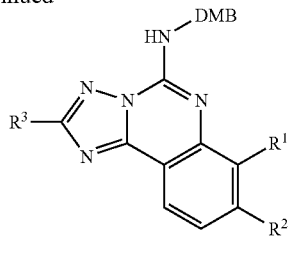

DMB = 2,4-dimethoxybenzyl

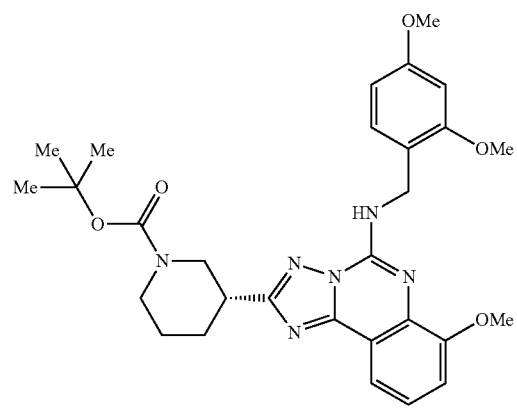 [SMILES: COc1ccc(CNc2nc3c(OC)cccc3c3nc([C@@H]4CCCN(C(=O)OC(C)(C)C)C4)nn23)c(OC)c1]

tert-butyl (R)-3-(5-((2,4-dimethoxybenzyl)amino)-7-methoxy-[1,2,4]triazolo[1,5-c]quinazolin-2-yl)piperidine-1-carboxylate Step 1: tert-butyl (R)-3-(hydrazinecarbonyl)piperidine-1-carboxylate An ethanol solution (50 mL) of (R)-1-tert-butyl-3-ethyl piperidine-1,3-dicarboxylate (13.3 g, 51.7 mmol) and hydrazine hydrate (13.0 g, 259 mmol) was stirred at 80° C. for 12 hours. The solvent was removed under reduced pressure, and the residue was purified by column chromatography on silica (dichloromethane) to afford the title compound. LC/MS=244 [M+1].

Step 2: tert-butyl (R)-3-(2-(2-chloro-8-methoxyquinazolin-4-yl)hydrazine-1-carbonyl)piperidine-1-carboxylate To a tetrahydrofuran solution (200 mL) of tert-butyl (R)-3-(hydrazinecarbonyl)piperidine-1-carboxylate (11.2 g, 46.1 mmol) and N,N-diisoproylethylamine (12.0 g, 92 mmol) at 70° C. was added dropwise a tetrahydrofuran solution (150 mL) of 2,4-dichloro-8-methoxyquinazoline (10.4 g, 35 mmol) over 20 minutes. Then the reaction mixture was stirred at 70° C. for 12 hours. The reaction mixture was evaporated under reduced pressure, diluted with dichloromethane (100 mL) and washed with water (50 mL×3). The combined organic layers were dried over anhydrous magnesium sulfate and concentrated under reduced pressure to afford the title compound. LC/MS=436 [M+1].

Step 3: tert-butyl (R)-3-(2-(2-((2,4-dimethoxybenzyl)amino)-8-methoxyquinazolin-4-yl)hydrazine-1-carbonyl)piperidine-1-carboxylate A 1,4-dioxane solution (300 mL) of tert-butyl (R)-3-(2-(2-chloro-8-methoxyquinazolin-4-yl)hydrazine-1-carbonyl)piperidine-1-carboxylate (16 g, 37 mmol), 2,4-dimethoxyphenylbenzylamine (7.4 g, 44.4 mmol) and N,N-diisoproylethylamine (9.5 g, 74 mmol) was stirred at 80° C. for 12 hours. The solution was evaporated under reduced pressure and diluted with dichloromethane (100 mL), washed with water (80 mL×3) and dried (magnesium sulfate). The organic layer was concentrated to afford the title compound. LC/MS=567 [M+1].

Step 4: tert-butyl (R)-3-(5-((2,4-dimethoxybenzyl)amino)-7-methoxy-[1,2,4]triazolo[1,5-c]quinazolin-2-yl)piperidine-1-carboxylate A N,O-bis(trimethylsilyl)acetamide solution (93 mL) of tert-butyl (R)-3-(2-(2-((2,4-dimethoxybenzyl)amino)-8-methoxyquinazolin-4-yl)hydrazine-1-carbonyl)piperidine-1-carboxylate (21 g, 37 mmol) was stirred at 140° C. for 12 hours. The reaction mixture was evaporated under reduced pressure and purified by column chromatography on silica, eluting with ethyl acetate/petroleum ether 1/5, to afford the title compound. LC/MS=549 [M+1].

The following examples in Table A were prepared similarly as INTERMEDIATE A1 with the appropriate ester in Step 1 and the appropriately substituted 2,4-dichloroquinazoline.

TABLE A

| Ex | Structure | IUPAC Name | MS (M + 1) |
|---|---|---|---|
| A2 | 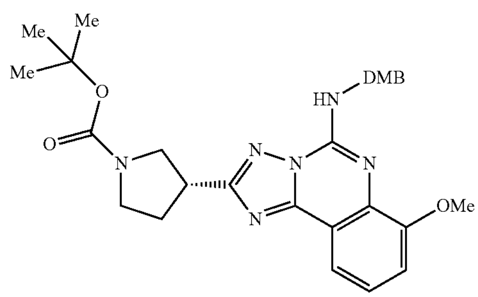 | tert-butyl (R)-3-(5-((2,4-dimethoxybenzyl)amino)-7-methoxy-[1,2,4]triazolo[1,5-c]quinazolin-2-yl)pyrrolidine-1-carboxylate | 535 |
| A3 | 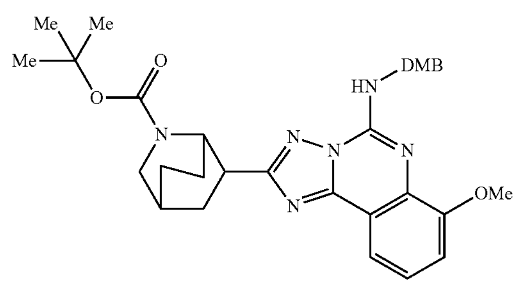 | tert-butyl 6-(5-((2,4-dimethoxybenzyl)amino)-7-methoxy-[1,2,4]triazolo[1,5-c]quinazolin-2-yl)-2-azabicyclo[2.2.2]octane-2-carboxylate | 575 |
| A4 | 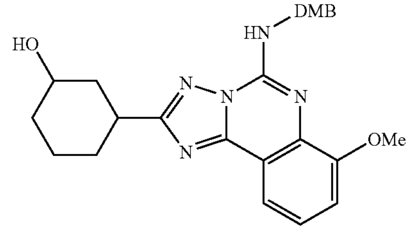 | 3-(5-((2,4-dimethoxybenzyl)amino)-7-methoxy-[1,2,4]triazolo[1,5-c]quinazolin-2-yl)cyclohexan-1-ol | 464 |

TABLE A-continued
| Ex | Structure | IUPAC Name | MS (M + 1) |
|---|---|---|---|
| A5 | 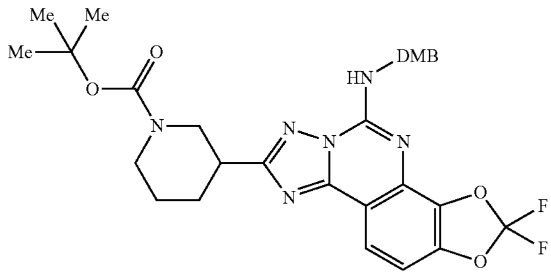 | tert-butyl 3-(5-((2,4-dimethoxybenzyl)amino)-2,2-difluoro-[1,3]dioxolo[4,5-h][1,2,4]triazolo[1,5-c]quinazolin-8-yl)piperidine-1-carboxylate | 599 |
| A6 | 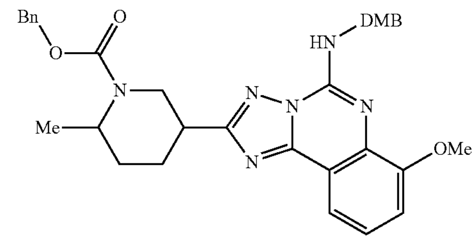 | benzyl 5-(5-((2,4-dimethoxybenzyl)amino)-7-methoxy-[1,2,4]triazolo[1,5-c]quinazolin-2-yl)-2-methylpiperidine-1-carboxylate | 597 |
| A7 | 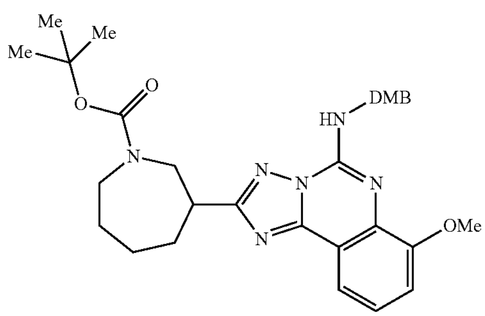 | tert-butyl 3-(5-((2,4-dimethoxybenzyl)amino)-7-methoxy-[1,2,4]triazolo[1,5-c]quinazolin-2-yl)azepane-1-carboxylate | 563 |
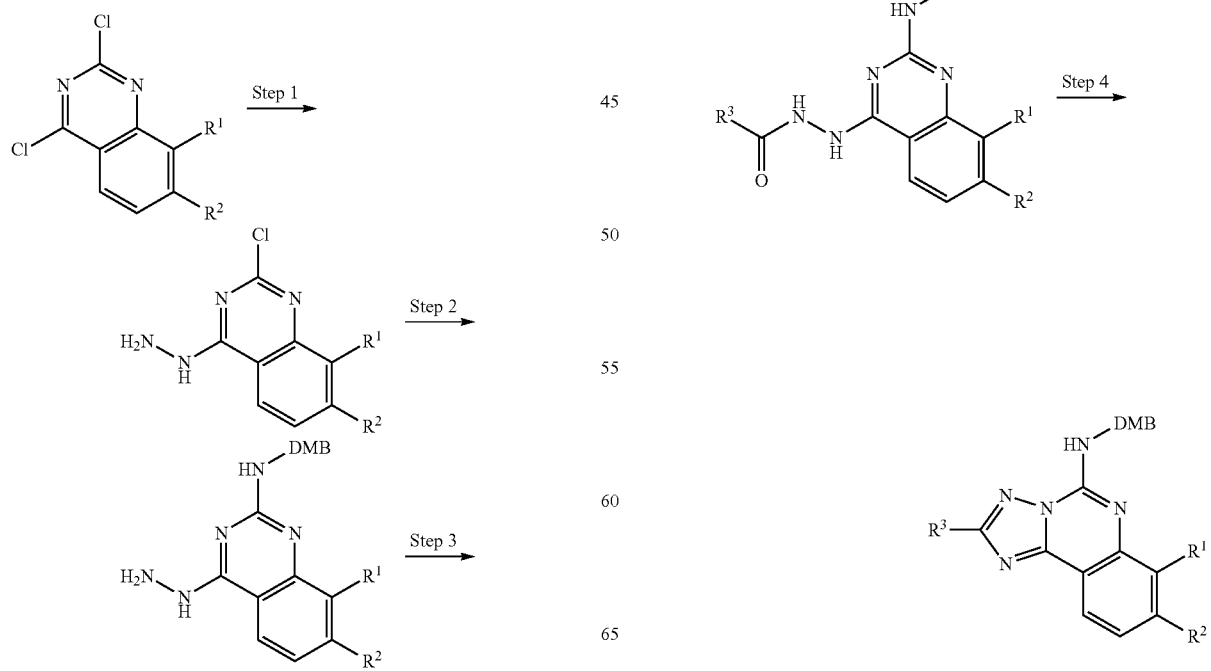
SCHEME B

Intermediate B1

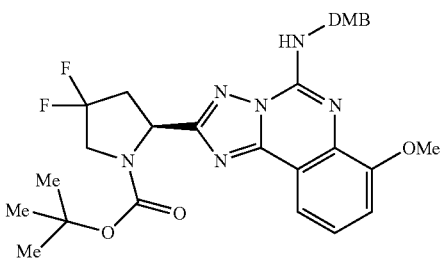

tert-butyl (S)-2-(5-((2,4-dimethoxybenzyl)amino)-7-methoxy-[1,2,4]triazolo[1,5-c]quinazolin-2-yl)-4,4-difluoropyrrolidine-1-carboxylate

Step 1: 2-chloro-4-hydrazinyl-8-methoxyquinazoline

To a stirred tetrahydrofuran solution (45 mL) at 0° C. of 2,4-dichloro-8-methoxyquinazoline (100 mg, 0.44 mmol) was added hydrazine hydrate (55 μL, 0.87 mmol) slowly. The reaction mixture was stirred at room temperature for 1 hour and concentrated in vacuo. The residue was washed with saturated aqueous sodium hydrogencarbonate solution and dried in vacuum oven to afford the title compound, which was used in the subsequent reaction without further purification. LC/MS=225 [M+1].

Step 2: N-(2,4-dimethoxybenzyl)-4-hydrazinyl-8-methoxyquinazolin-2-amine

The title compound was made by following the procedures described in Step 3 for INTERMEDIATE A1, substituting 2-chloro-4-hydrazinyl-8-methoxyquinazoline for tert-butyl (R)-3-(2-(2-chloro-8-methoxyquinazolin-4-yl)hydrazine-1-carbonyl)piperidine-1-carboxylate. LC/MS=356 [M+1].

Step 3: tert-butyl (S)-2-(2-(2-((2,4-dimethoxybenzyl)amino)-8-methoxyquinazolin-4-yl)hydrazine-1-carbonyl)-4,4-difluoropyrrolidine-1-carboxylate A solution of (1-cyano-2-ethoxy-2-oxoethylidenaminooxy)dimethylamino-morpholino-carbenium hexafluorophosphate (11.5 g, 26.9 mmol) and (S)-1-(tert-butoxycarbonyl)-4,4-difluoropyrrolidine-2-carboxylic acid (6.7 g, 26.7 mmol) in N,N-dimethylformamide (80 mL) and N,N-diisopropylethylamine (9 mL, 51.5 mmol) was stirred for 10 minutes at room temperature. N-(2,4-dimethoxybenzyl)-4-hydrazinyl-8-methoxyquinazolin-2-amine (9.0 g, 25.3 mmol) was then added and stirred at room temperature for 18 hours. The reaction mixture was diluted with water (100 mL) and extracted with ethyl acetate (200 mL×2). The organic layer was washed with water (100 mL×2), brine (100 mL) and dried (magnesium sulfate). Concentration in vacuo afforded the title compound, which was used in the subsequent reaction without further purification. LC/MS=589 [M+1].

Step 4: (S)-2-(4,4-difluoropyrrolidin-2-yl)-N-(2,4-dimethoxybenzyl)-7-methoxy-[1,2,4]triazolo[1,5-c]quinazolin-5-amine The title compound was made by following the procedures described in Step 4 for INTERMEDIATE A1, substituting tert-butyl (S)-2-(2-(2-((2,4-dimethoxybenzyl)amino)-8-methoxyquinazolin-4-yl)hydrazine-1-carbonyl)-4,4-difluoropyrrolidine-1-carboxylate for tert-butyl (R)-3-(2-(2-((2,4-dimethoxybenzyl)amino)-8-methoxyquinazolin-4-yl)hydrazine-1-carbonyl)piperidine-1-carboxylate. LC/MS=571 [M+1].

The following examples in Table B were prepared similarly as INTERMEDIATE B1 with the appropriate acid in step 3.

TABLE B

| Ex | Structure | IUPAC Name | MS (M + 1) |
|---|---|---|---|
| B2 | 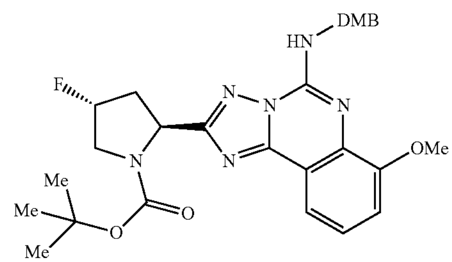 | tert-butyl (2S,4R)-2-(5-((2,4-dimethoxybenzyl)amino)-7-methoxy-[1,2,4]triazolo[1,5-c]quinazolin-2-yl)-4-fluoropyrrolidine-1-carboxylate | 553 |
| B3 | 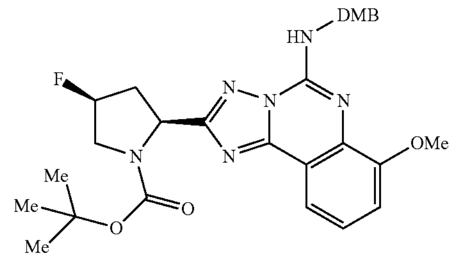 | tert-butyl (2S,4S)-2-(5-((2,4-dimethoxybenzyl)amino)-7-methoxy-[1,2,4]triazolo[1,5-c]quinazolin-2-yl)-4-fluoropyrrolidine-1-carboxylate | 553 |

TABLE B-continued

| Ex | Structure | IUPAC Name | MS (M + 1) |
|---|---|---|---|
| B4 | 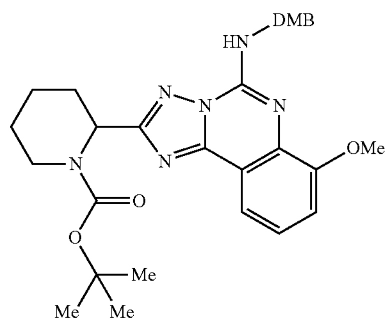 | tert-butyl 2-(5-((2,4-dimethoxybenzyl)amino)-7-methoxy-[1,2,4]triazolo[1,5-c]quinazolin-2-yl)piperidine-1-carboxylate | 549 |
| B5 | 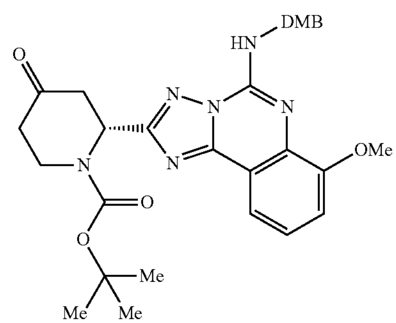 | tert-butyl (R)-2-(5-((2,4-dimethoxybenzyl)amino)-7-methoxy-[1,2,4]triazolo[1,5-c]quinazolin-2-yl)-4-oxopiperidine-1-carboxylate | 563 |
| B6 | 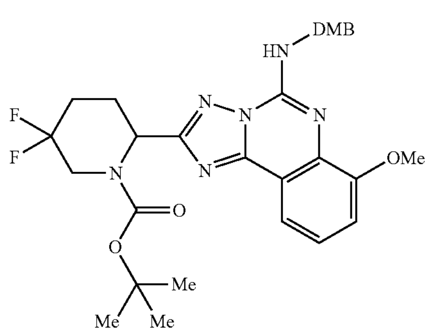 | tert-butyl 2-(5-((2,4-dimethoxybenzyl)amino)-7-methoxy-[1,2,4]triazolo[1,5-c]quinazolin-2-yl)-5,5-difluoropiperidine-1-carboxylate | 585 |

SCHEME C

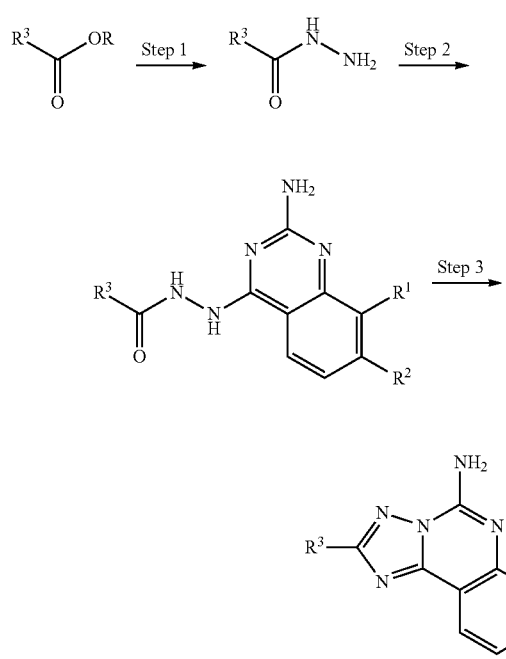

Intermediate C1 tert-butyl (R)-2-(5-amino-7-methoxy-[1,2,4]triazolo[1,5-d]quinazolin-2-yl)pyrrolidine-1-carboxylate

Step 1: tert-butyl (R)-2-(hydrazinecarbonyl)pyrrolidine-1-carboxylate

The title compound was made by following the procedures described in step 1 for INTERMEDIATE A1, substituting 1-(tert-butyl) 2-methyl (R)-pyrrolidine-1,2-dicarboxylate for (R)-1-tert-butyl-3-ethyl piperidine-1,3-dicarboxylate. LC/MS=230 [M+1].

Step 2: tert-butyl (R)-3-(2-(2-chloro-8-methoxyquinazolin-4-yl)hydrazine-1-carbonyl)piperidine-1-carboxylate To a N,N-dimethylformamide (8 mL) solution of tert-butyl (R)-2-(hydrazinecarbonyl)pyrrolidine-1-carboxylate (1.07 g, 4.6 mmol) and N-(8-methoxy-4-(1H-1,2,4-triazol-1-yl)quinazolin-2-yl)acetamide (600 mg, 2.1 mmol, synthesis reported in WO2014/101113) was added N,N-diisopropylethylamine (1.29 mL, 7.4 mmol). The reaction mixture was stirred at 80° C. for 4 days. After it was cooled down to room temperature, methanol (3 mL) and water (1.5 mL) was added, followed by potassium carbonate (0.87 g, 6.3 mmol). The reaction mixture was heated at 65° C. for 2 hours. After it was cooled down to room temperature, it was diluted and extracted with dichloromethane. The combined organic layers were washed with water, brine, dried (potassium carbonate), and concentrated in vacuo to afford the title compound, which was used in the subsequent step without further purification. LC/MS=403 [M+1].

Step 3: tert-butyl 3-(2-(2-amino-8-methoxyquinazolin-4-yl)hydrazine-1-carbonyl)azetidine-1-carboxylate The title compound was made by following the procedures described in step 4 for INTERMEDIATE A1, substituting tert-butyl (R)-3-(2-(2-chloro-8-methoxyquinazolin-4-yl)hydrazine-1-carbonyl)piperidine-1-carboxylate for tert-butyl (R)-3-(2-(2-((2,4-dimethoxybenzyl)amino)-8-methoxyquinazolin-4-yl)hydrazine-1-carbonyl)piperidine-1-carboxylate. LC/MS=385 [M+1].

The following examples in Table C were prepared similarly as INTERMEDIATE C1 with the appropriate acid in step 3.

TABLE C

| Ex | Structure | IUPAC Name | MS (M + 1) |
|----|-----------|------------|------------|
| C2 | 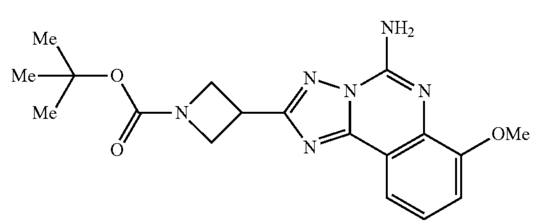 [SMILES: COc1cccc2c1nc(N)n1nc(C3CN(C(=O)OC(C)(C)C)C3)nc21] | tert-butyl 3-(5-amino-7-methoxy-[1,2,4]triazolo[1,5-c]quinazolin-2-yl)azetidine-1-carboxylate | 371 |

| Ex | Structure | IUPAC Name | MS (M + 1) |
|---|---|---|---|
| C3 | 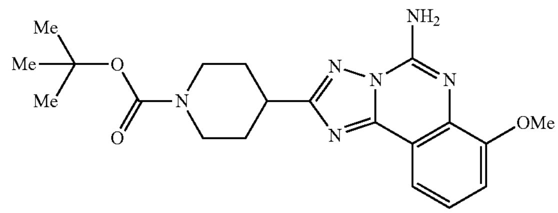 [SMILES: COc1cccc2c1nc(N)n1nc(C3CCN(C(=O)OC(C)(C)C)CC3)nc21] | tert-butyl 4-(5-amino-7-methoxy-[1,2,4]triazolo[1,5-c]quinazolin-2-yl)piperidine-1-carboxylate | 399 |

Example 1

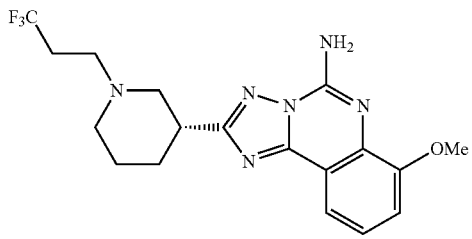 [SMILES: COc1cccc2c1nc(N)n1nc([C@@H]3CCCN(CCC(F)(F)F)C3)nc21]

(R)-7-methoxy-2-(1-(3,3,3-trifluoropropyl)piperidin-3-yl)-[1,2,4]triazolo[1,5-d]quinazolin-5-amine

Step 1: (R)—N-(2,4-dimethoxybenzyl)-7-methoxy-2-(piperidin-3-yl)-[1,2,4]triazolo[1,5-c]quinazolin-5-amine To a dichloromethane solution (300 mL) of tert-butyl (R)-3-(5-((2,4-dimethoxybenzyl)amino)-7-methoxy-[1,2,4]triazolo[1,5-c]quinazolin-2-yl)piperidine-1-carboxylate (13.4 g, 24 mmol) at 0° C. was added dropwise trifluoroacetic acid (30 mL). After the addition was completed, the reaction mixture was stirred at room temperature for 4 hours. The solution was washed with aqueous saturated sodium hydrogencarbonate solution (200 mL×3) and brine (200 mL). The organic layer was concentrated. To the residue was added dichloromethane (20 mL) and diethyl ether (100 mL), and then the resulting suspension was stirred at room temperature and filtered to obtain a solid. The solid was washed again using a mixture of dichloromethane (20 mL) and ether (100 mL), and dried in vacuo to afford the title compound. LC/MS=449 [M+1]. $^1$H-NMR (DMSO-d$_6$, 400 MHz) δ 8.01 (t, 1H), 7.76 (d, 1H), 7.32-7.22 (m, 3H), 6.59 (d, 1H), 6.47-6.44 (m, 1H), 4.70 (d, 2H), 3.88 (t, 6H), 3.73 (s, 3H), 3.21 (d, 1H), 3.07-3.01 (m, 1H), 2.95 (d, 1H), 2.86 (d, 1H), 2.60-2.55 (m, 1H), 2.14 (t, 1H), 1.84 (d, 1H), 1.72-1.68 (m, 1H), 1.52 (d, 1H).

Step 2: (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine A N,N-dimethylformamide solution (6 mL) of (R)—N-(2,4-dimethoxybenzyl)-7-methoxy-2-(piperidin-3-yl)-[1,2,4]triazolo[1,5-c]quinazolin-5-amine (1.0 g, 2.24 mmol), 1,1,1-trifluoro-3-iodopropane (2.5 g, 11.2 mmol), and potassium carbonate (924 mg, 6.72 mmol) was added to a sealed tube fitted with a magnetic stir bar. The mixture was stirred at 80° C. for 4 hours. After the completion of the reaction, the mixture was extracted with ethyl acetate (30 mL×3). The organic layer was washed with brine, dried (sodium sulfate), and concentrated in vacuo to afford the title compound, which was used in the next step without further purification. LC/MS=545 [M+1].

Step 3: (R)-7-methoxy-2-(1-(3,3,3-trifluoropropyl)piperidin-3-yl)-[1,2,4]triazolo[1,5-c]quinazolin-5-amine To a dichloromethane solution (12 mL) of trifluoroacetic acid (6 mL) at room temperature was added (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine (1.2 g, 2.20 mmol). The mixture was stirred at room temperature for 2 days. After the completion of the reaction, the mixture was neutralized by slowly adding saturated solution of potassium carbonate on an ice-bath. The mixture was extracted with dichloromethane (30 mL×3), dried (sodium sulfate), and concentrated in vacuo. The crude product was purified by column chromatography on silica (ethyl acetate/petroleum ether 2:1-1:1) to afford the title compound. LC/MS=395 [M+1]. $^1$H-NMR (CDCl$_3$, 400 MHz) δ 7.94 (d, 1H), 7.36 (t, 1H), 7.15 (d, 1H), 6.34 (b, 2H), 4.06 (s, 3H), 3.28 (d, 2H), 2.92 (m, 1H), 2.71 (t, 2H), 2.49-2.42 (m, 1H), 2.40-2.35 (m, 2H), 2.26-2.16 (m, 2H), 1.81-1.86 (m, 1H), 1.83-1.72 (m, 2H).

The following examples in Table 1 were prepared similarly as EXAMPLE 1, starting from the appropriate halide in step 2.

TABLE 1

| Ex | Structure | IUPAC Name | MS (M + 1) |
|---|---|---|---|
| 2 | 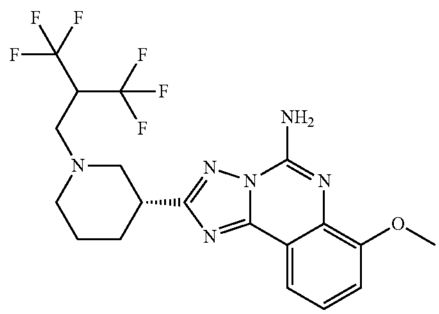 [SMILES: COc1cccc2c1nc(N)n1nc([C@@H]3CCCN(CC(C(F)(F)F)C(F)(F)F)C3)nc21] | (R)-7-methoxy-2-(1-(3,3,3-trifluoro-2-(trifluoromethyl)propyl)piperidin-3-yl)-[1,2,4]triazolo[1,5-c]quinazolin-5-amine | 463 |
| 3 | 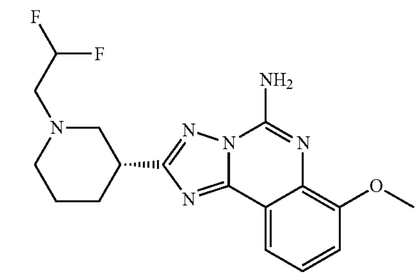 [SMILES: COc1cccc2c1nc(N)n1nc([C@@H]3CCCN(CC(F)F)C3)nc21] | (R)-2-(1-(2,2-difluoroethyl)piperidin-3-yl)-7-methoxy-[1,2,4]triazolo[1,5-c]quinazolin-5-amine | 363 |
| 4 | 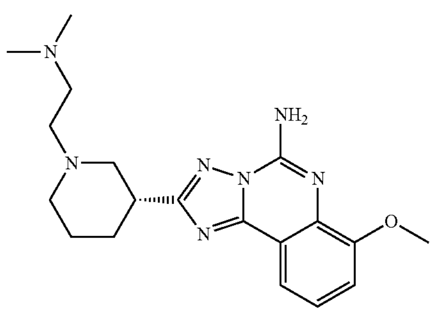 | (R)-2-(1-(2-(dimethylamino)ethyl)piperidin-3-yl)-7-methoxy-[1,2,4]triazolo[1,5-c]quinazolin-5-amine | 370 |
| 5 | 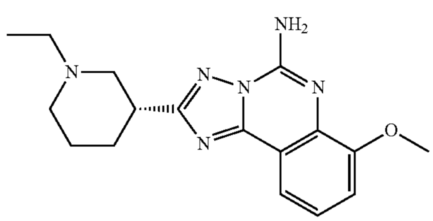 [SMILES: CCN1CCC[C@@H](c2nc3c4cccc(OC)c4nc(N)n3n2)C1] | (R)-2-(1-ethylpiperidin-3-yl)-7-methoxy-[1,2,4]triazolo[1,5-c]quinazolin-5-amine | 327 |
| 6 | 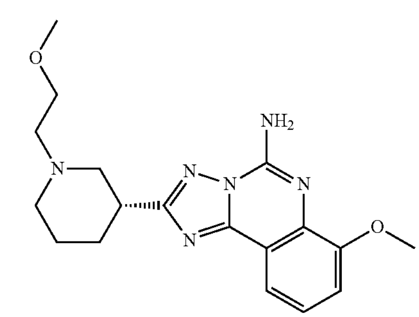 [SMILES: COCCN1CCC[C@@H](c2nc3c4cccc(OC)c4nc(N)n3n2)C1] | (R)-7-methoxy-2-(1-(2-methoxyethyl)piperidin-3-yl)-[1,2,4]triazolo[1,5-c]quinazolin-5-amine | 357 |

TABLE 1-continued

| Ex | Structure | IUPAC Name | MS (M + 1) |
|---|---|---|---|
| 7 | 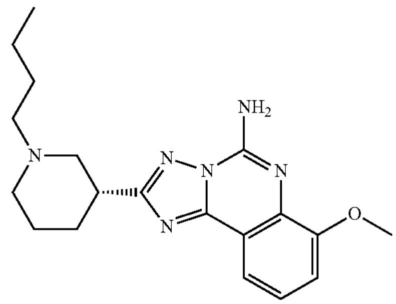 [SMILES: CCCCN1CCC[C@@H](c2nc3c4cccc(OC)c4nc(N)n3n2)C1] | (R)-2-(1-butylpiperidin-3-yl)-7-methoxy-[1,2,4]triazolo[1,5-c]quinazolin-5-amine | 355 |
| 8 | 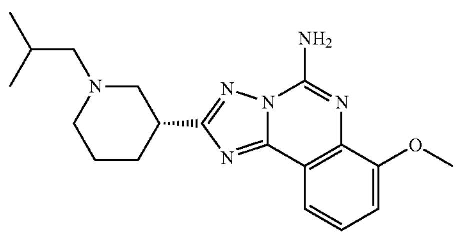 [SMILES: COc1cccc2c1nc(N)n1nc([C@@H]3CCCN(CC(C)C)C3)nc21] | (R)-2-(1-isobutylpiperidin-3-yl)-7-methoxy-[1,2,4]triazolo[1,5-c]quinazolin-5-amine | 355 |
| 9 | 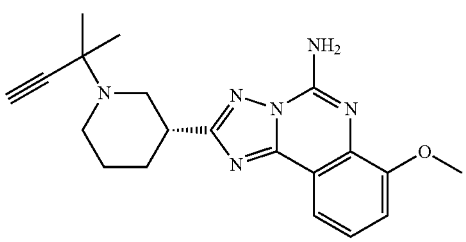 [SMILES: C#CC(C)(C)N1CCC[C@@H](c2nc3c4cccc(OC)c4nc(N)n3n2)C1] | (R)-7-methoxy-2-(1-(2-methylbut-3-yn-2-yl)piperidin-3-yl)-[1,2,4]triazolo[1,5-c]quinazolin-5-amine | 365 |
| 10 | 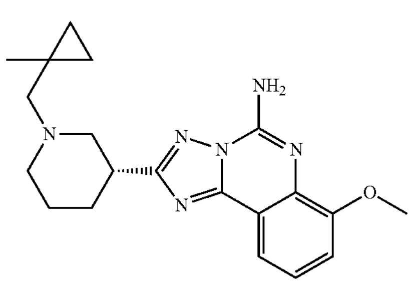 | (R)-7-methoxy-2-(1-((1-methylcyclopropyl)methyl)piperidin-3-yl)-[1,2,4]triazolo[1,5-c]quinazolin-5-amine | 367 |

TABLE 1-continued

| Ex | Structure | IUPAC Name | MS (M + 1) |
|---|---|---|---|
| 11 | 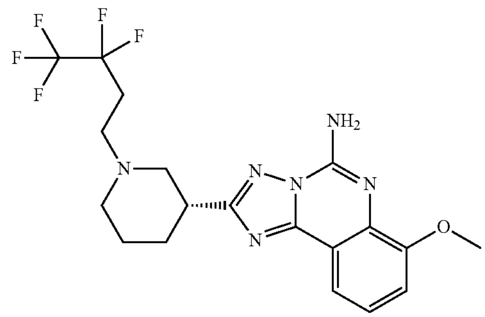 [SMILES: COc1cccc2c1nc(N)n1nc([C@@H]3CCCN(CCC(F)(F)C(F)(F)F)C3)nc21] | (R)-7-methoxy-2-(1-(3,3,4,4,4-pentafluorobutyl)piperidin-3-yl)-[1,2,4]triazolo[1,5-c]quinazolin-5-amine | 445 |

Example 12

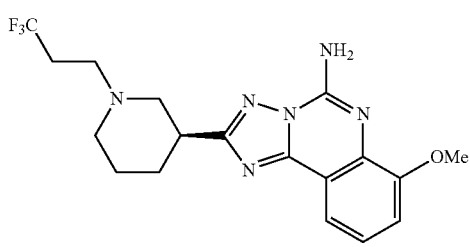 [SMILES: COc1cccc2c1nc(N)n1nc([C@H]3CCCN(CCC(F)(F)F)C3)nc21]

(S)-7-methoxy-2-(1-(3,3,3-trifluoropropyl)piperidin-3-yl)-[1,2,4]triazolo[1,5-c]quinazolin-5-amine The title compound was made by following the procedures described in EXAMPLE 1, substituting a racemic mixture of tert-butyl 3-(5-((2,4-dimethoxybenzyl)amino)-7-methoxy-[1,2,4]triazolo[1,5-c]quinazolin-2-yl)piperidine-1-carboxylate for the (R)-enantiomer in step 1 and separating the enantiomers of the final product through chiral preparative SFC. LC/MS=395 [M+1]. R-enantiomer: RT=3.35 min (AD-H column (4.6*250 mm, 5 μm); ethanol (0.1% diethylamine) 0.6 mL/min; supercritical carbon dioxide 2.4 mL/min). S-enantiomer: RT=3.68 min (AD-H column (4.6*250 mm, 5 μm); ethanol (0.1% diethylamine) 0.6 mL/min; supercritical carbon dioxide 2.4 mL/min).

Example 13

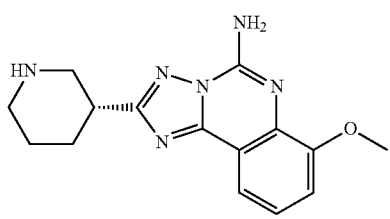 [SMILES: COc1cccc2c1nc(N)n1nc([C@@H]3CCCNC3)nc21]

(R)-7-methoxy-2-(piperidin-3-yl)-[1,2,4]triazolo[1,5-c]quinazolin-5-amine

The title compound was made by following the procedures described in Step 3 for EXAMPLE 1, substituting (R)—N-(2,4-dimethoxybenzyl)-7-methoxy-2-(piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=299 [M+1]. $^1$H-NMR (CD$_3$OD-d$_4$, 400 MHz) δ 7.90-7.88 (m, 1H), 7.41 (t, 1H), 7.33-7.31 (m, 1H), 4.04 (s, 3H), 3.77-3.75 (m, 1H), 3.63-3.56 (m, 2H), 3.42-3.37 (m, 1H), 3.24-3.18 (m, 1H), 2.42-2.37 (m, 1H), 2.14-2.03 (m, 2H), 1.97-1.91 (m, 1H).

Example 14

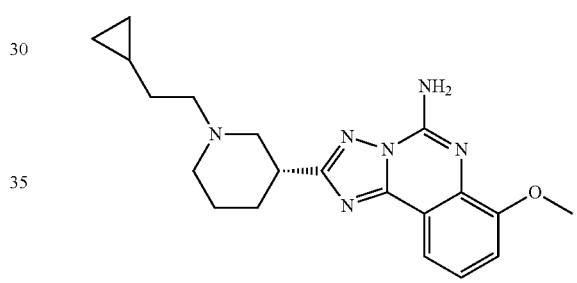

(R)-2-(1-(2-cyclopropylethyl)piperidin-3-yl)-7-methoxy-[1,2,4]triazol[1,5-c]quinazolin-5-amine Step 1: 2-cyclopropylethyl methanesulfonate To a dichloromethane solution (3 mL) of 2-cyclopropylethanol (172 mg, 2.0 mmol) was added trimethylamine (0.85 mL, 6.1 mmol) and methanesulfonyl chloride (0.23 mL, 3.0 mmol). The mixture was stirred at room temperature for 20 hours. The reaction mixture was washed with water (10 mL) and saturated aqueous sodium hydrogencarbonate solution (15 mL). The organic layer was concentrated to afford the title compound.

Step 2: (R)-2-(1-(2-cyclopropylethyl)piperidin-3-yl)-7-methoxy-[2,4]triazolo[1,5-c]quinazolin-5-amine The title compound was made by following the procedures described for EXAMPLE 1, substituting 2-cyclopropylethyl methanesulfonate for 1,1,1-trifluoro-3-iodopropane in step 2. LC/MS=367 [M+1]. $^1$H-NMR (DMSO-d$_6$, 400 MHz) δ 7.77 (b, 2H), 7.63-7.59 (m, 1H), 7.22-7.12 (m, 2H), 3.79-3.71 (m, 4H), 3.39-3.33 (m, 1H), 3.17-3.13 (m, 3H), 2.94-2.89 (m, 1H), 2.12-2.07 (m, 1H), 1.92-1.88 (m, 1H), 1.79-1.66 (m, 2H), 1.55-1.46 (m, 2H), 0.59-0.56 (m, 1H), 0.35-0.33 (m, 2H), 0.00 (b, 2H).

The following examples in Table 2 were prepared similarly as EXAMPLE 14 starting from the appropriate alcohols:

TABLE 2

| Ex | Structure | IUPAC Name | MS (M + 1) |
|---|---|---|---|
| 15 | 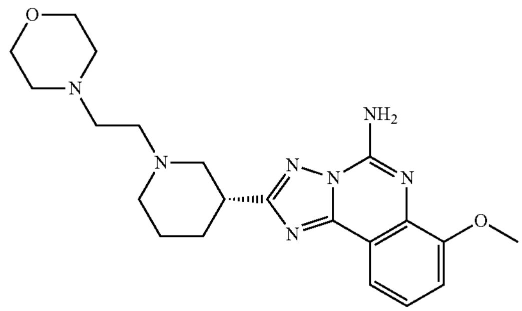 [SMILES: COc1cccc2c1nc(N)n1nc([C@@H]3CCCN(CCN4CCOCC4)C3)nc21] | (R)-7-methoxy-2-(1-(2-morpholinoethyl)piperidin-3-yl)-[1,2,4]triazolo[1,5-c]quinazolin-5-amine | 412 |
| 16 | 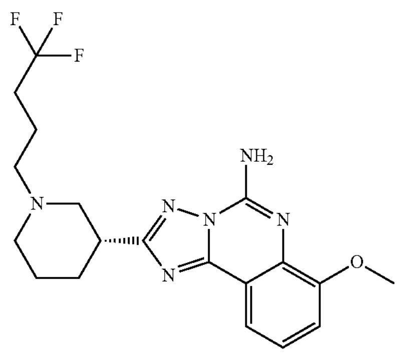 [SMILES: COc1cccc2c1nc(N)n1nc([C@@H]3CCCN(CCCC(F)(F)F)C3)nc21] | (R)-7-methoxy-2-(1-(4,4,4-trifluorobutyl)piperidin-3-yl)-[1,2,4]triazolo[1,5-c]quinazolin-5-amine | 409 |
| 17 | 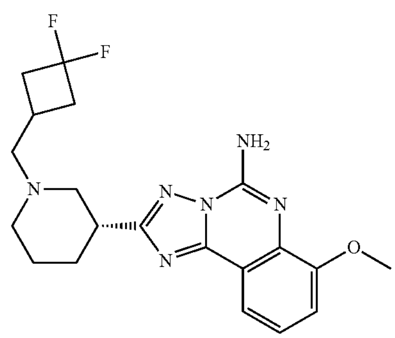 [SMILES: COc1cccc2c1nc(N)n1nc([C@@H]3CCCN(CC4CC(F)(F)C4)C3)nc21] | (R)-2-(1-((3,3-difluorocyclobutyl)methyl)piperidin-3-yl)-7-methoxy-[1,2,4]triazolo[1,5-c]quinazolin-5-amine | 403 |

Example 18

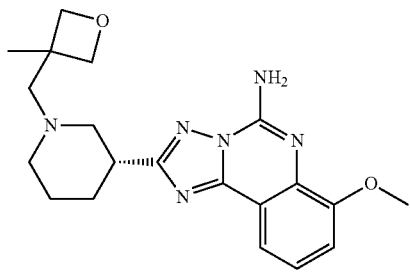

(R)-7-methoxy-2-(1-((3-methyloxetan-3-yl)methyl)piperidin-3-yl)-[1,2,4]triazolo[1,5-d]quinazolin-5-amine Step 1: 1-(bromomethyl)-1-methylcyclobutane To a dichloromethane solution (30 mL) of (1-methylcyclobutyl)methanol (600 mg, 5.88 mmol) at 0° C. was added tetrabromomethane (2.14 g, 6.47 mmol), followed by the addition of triphenylphosphine (2.15 g, 8.23 mmol) in portions. The reaction was warmed to room temperature and stirred for 1 hour. The solvent was removed under reduced pressure. The residue was diluted with diethyl ether (30 mL), filtered, and the filtrate was diluted with hexanes (20 mL). After filtration, the filtrate was concentrated to afford the title compound. ¹H-NMR (CDCl₃, 400 MHz) δ 4.46-4.39 (m, 4H), 3.65 (s, 2H), 1.43 (s, 3H).

Step 2: (R)-7-methoxy-2-(1-((3-methyloxetan-3-yl)methyl)piperidin-3-yl)-[1,2,4]triazolo[1,5-c]quinazolin-5-amine A mixture of (R)-7-methoxy-2-(piperidin-3-yl)-[1,2,4]triazolo[1,5-c]quinazolin-5-amine (60 mg, 0.2 mmol), 1-(bromomethyl)-1-methylcyclobutane (100 mg, 0.6 mmol), N,N-diisoproylethylamine (52 mg, 0.4 mmol), sodium iodide (30 mg, 0.2 mmol), and DMF (5 mL) was sealed up and stirred at 80° C. for 16 hours. Water (60 mL) was added, and the mixture was extracted with dichloromethane (3×60 mL). The combined organic layer was washed with brine (60 mL), dried (sodium sulfate), concentrated and purified by reverse phase HPLC (acetonitrile/water with 0.05% ammonium hydrogencarbonate) to afford the title compound. LC/MS=383 [M+1]. ¹H-NMR (CDCl₃, 400 MHz) δ 7.93 (d, 1H), 7.36 (t, 1H), 7.15 (d, 1H), 6.12 (s, 2H), 4.56-4.52 (m, 2H), 4.34 (t, 2H), 4.06 (s, 3H), 3.27-3.23 (m, 1H), 3.00-2.97 (m, 1H), 2.64-2.57 (m, 3H), 2.48 (t, 1H), 2.18-2.15 (m, 2H), 1.79-1.70 (m, 3H), 1.43 (s, 3H).

Example 19

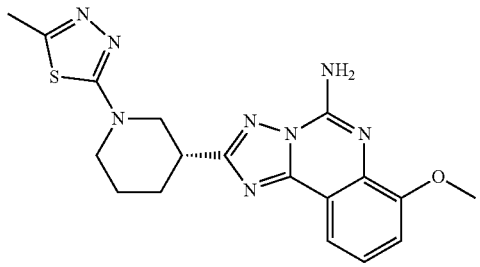

(R)-7-methoxy-2-(1-(5-methyl-1,3,4-thiadiazol-2-yl)piperidin-3-yl)-[1,2,4]triazolo[1,5-c]quinazolin-5-amine Step 1: 2-bromo-5-methyl-1,3,4-thiadiazole 5-Methyl-1,3,4-thiadiazol-2-amine (300 mg, 2.61 mmol) was added to a stirred hydrobromic acid (4 mL, 48%) at room temperature, followed by the addition of water (3 mL). The mixture was cooled to 0° C. Copper(I) bromide (43 mg, 0.26 mmol) was then added, followed by an aqueous solution (2 mL) of sodium nitrite (216 mg, 3.12 mmol) over 40 minutes. The mixture was stirred at 0° C. for another 15 minutes, then stirred at 25° C. for 2 hours. It was quenched by aqueous saturated sodium hydrogencarbonate solution (25 mL), and extracted with dichloromethane (25 mL×3). The organic layer was washed with brine (20 mL), dried (magnesium sulfate), and concentrated to afford the title compound, which was used for next step directly without further purification. LC/MS=179 [M+1].

Step 2: (R)—N-(2,4-dimethoxybenzyl)-7-methoxy-2-(1-(5-methyl-1,3,4-thiadiazol-2-yl)piperidin-3-yl)-[1,2,4]triazolo[1,5-c]quinazolin-5-amine A microwave vial was charged with (R)—N-(2,4-dimethoxybenzyl)-7-methoxy-2-(piperidin-3-yl)-[1,2,4]triazolo[1,5-c]quinazolin-5-amine (100 mg, 0.22 mmol), 2-bromo-5-methyl-1,3,4-thiadiazole (79 mg, 0.44 mmol), potassium carbonate (60 mg, 0.44 mmol) and DMF (2 mL). The mixture was irradiated with microwaves at 135° C. for 6 hours. The mixture was poured into water (20 mL), extracted with dichloromethane (25 mL×3), and dried (magnesium sulfate). The solvent was concentrated to afford the title compound, which was used for next step directly without further purification. LC/MS=547 [M+1].

Step 3: (R)-7-methoxy-2-(1-(5-methyl-1,3,4-thiadiazol-2-yl)piperidin-3-yl)-[1,2,4]triazolo[1,5-c]quinazolin-5-amine The title compound was made by following the procedures described in Step 3 for EXAMPLE 1, substituting (R)—N-(2,4-dimethoxybenzyl)-7-methoxy-2-(1-(5-methyl-1,3,4-thiadiazol-2-yl)piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=382[M+1]. ¹H-NMR (DMSO-d₆, 400 MHz) δ 7.80 (m, 3H), 7.33 (t, 1H), 7.22 (d, 1H), 4.32-4.27 (m, 1H), 3.91 (s, 3H), 3.77 (d, 1H), 3.48 (t, 1H), 3.31-3.23 (m, 2H), 2.52 (t, 3H), 2.29 (t, 1H), 1.98-1.86 (m, 2H), 1.76-1.73 (m, 1H).

The following examples in Table 3 were prepared similarly as EXAMPLE 19 starting from the appropriate aryl halides:

TABLE 3

| Ex | Structure | IUPAC Name | MS (M + 1) |
|---|---|---|---|
| 20 | 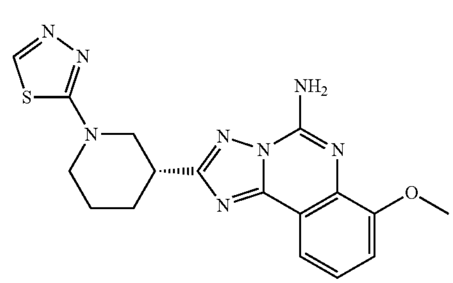 [SMILES: COc1cccc2c1nc(N)n1nc([C@@H]3CCCN(c4nncs4)C3)nc21] | (R)-2-(1-(1,3,4-thiadiazol-2-yl)piperidin-3-yl)-7-methoxy-[1,2,4]triazolo[1,5-c]quinazolin-5-amine | 383 |

TABLE 3-continued

| Ex | Structure | IUPAC Name | MS (M + 1) |
|---|---|---|---|
| 21 | 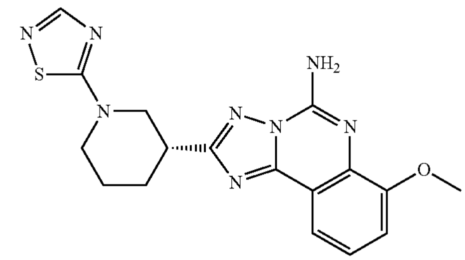 [SMILES: COc1cccc2c1nc(N)n1nc([C@@H]3CCCN(c4ncns4)C3)nc21] | (R)-2-(1-(1,2,4-thiadiazol-5-yl)piperidin-3-yl)-7-methoxy-[1,2,4]triazolo[1,5-c]quinazolin-5-amine | 383 |
| 22 | 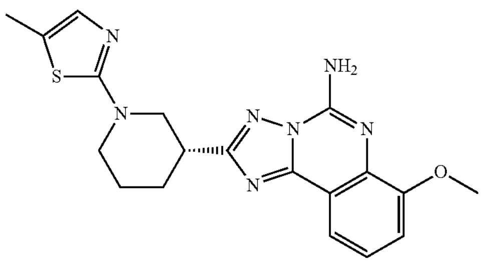 | (R)-7-methoxy-2-(1-(5-methylthiazol-2-yl)piperidin-3-yl)-[1,2,4]triazolo[1,5-c]quinazolin-5-amine | 396 |

Example 23

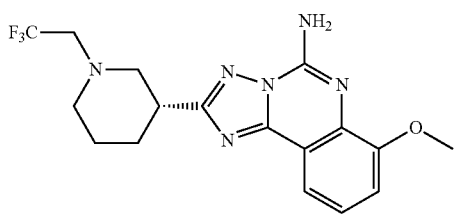 [SMILES: COc1cccc2c1nc(N)n1nc([C@@H]3CCCN(CC(F)(F)F)C3)nc21]

(R)-7-methoxy-2-(1-(2,2,2-trifluoroethyl)piperidin-3-yl)-[1,2,4]triazolo[1,5-c]quinazolin-5-amine Step 1: (R)—N-(2,4-dimethoxybenzyl)-7-methoxy-2-(1-(2,2,2-trifluoroethyl)piperidin-3-yl)-[1,2,4]triazolo[1,5-d]quinazolin-5-amine In a sealed tube, a N,N-dimethylformamide solution (3 mL) of (R)—N-(2,4-dimethoxybenzyl)-7-methoxy-2-(piperidin-3-yl)-[1,2,4]triazolo[1,5-c]quinazolin-5-amine (190 mg, 0.4 mmol), 2,2,2-trifluoroethyl trifluoromethanesulfonate (240 mg, 0.6 mmol) and potassium carbonate (83 mg, 0.6 mmol) was stirred at room temperature for 18 hours. After the completion of the reaction, the mixture was extracted with ethyl acetate (30 mL×3). The organic layer was washed with brine (20 mL), dried (sodium sulfate), and concentrated to afford the title compound, which was used for next step directly without further purification. LC/MS=531 [M+1].

Step 2: (R)-7-methoxy-2-(1-(2,22-trifluoroethyl)piperidin-3-yl)-[1,2,4]triazolo[1,5-d]quinazolin-5-amine The title compound was made by following the procedures described in Step 3 for EXAMPLE 1, substituting (R)—N-(2,4-dimethoxybenzyl)-7-methoxy-2-(1-(2,2,2-trifluoroethyl)piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=381 [M+1]. $^1$H-NMR (CDCl$_3$, 400 MHz) δ 7.93 (d, 1H), 7.36 (dd, 1H), 7.15 (d, 1H), 6.28 (b, 2H), 4.06 (s, 3H), 3.38 (dd, 1H), 3.31-3.28 (m, 1H), 3.10 (q, 2H), 3.03 (d, 1H), 2.79 (d, 1H), 2.50-2.48 (m, 1H), 2.23-2.21 (m, 1H), 1.84-1.74 (m, 3H).

Examples 24A and 24B

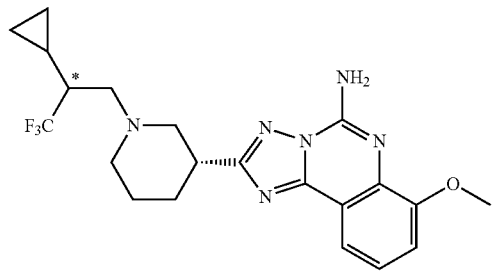 [SMILES: COc1cccc2c1nc(N)n1nc([C@@H]3CCCN(CC(C4CC4)C(F)(F)F)C3)nc21]

2-((R)-1-((R)-2-cyclopropyl-2-fluoroethyl)piperidin-3-yl)-7-methoxy-[1,2,4]triazolo[1,5-c]quinazolin-5-amine and 2-((R)-1-((S)-2-cyclopropyl-2-fluoroethyl)piperidin-3-yl)-7-methoxy-[1,2,4]triazolo[1,5-c]quinazolin-5-amine Step 1: (±)-ethyl 2-cyclopropyl-2-hydroxyacetate To a dried three-neck flask (50 mL) was charged a tetrahydrofuran solution (5 mL) of ethyl 2-oxoacetate (92 mg, 0.9 mmol). The solution was cooled to −20° C. under nitrogen. Then a tetrahydrofuran solution of cyclopropylmagnesium bromide (7 mL, 0.7 mmol) was added dropwise. Once the addition was completed, the reaction mixture was stirred at −20° C. for 2 hours. The reaction mixture was quenched with water (2 mL). The resulted mixture was further diluted with water (5 mL), and extracted with dichloromethane (10 mL×2). The organic layer was combined, dried (sodium sulfate), filtered and concentrated by rotary evaporation. The crude product was purified by column chromatography on silica (ethyl acetate/petroleum ether) to afford the title compound. LC/MS=145 [M+1].

Step 2: (±)-ethyl 2-bromo-2-cyclopropylacetate

To a dichloromethane solution (10 mL) of (±)-ethyl 2-cyclopropyl-2-hydroxyacetate (50 mg, 0.35 mmol) was added triphenylphosphine (320 mg, 1.22 mmol) at 0° C., followed by the addition of carbon tetrabromide (172 mg, 0.52 mmol). The reaction mixture was stirred at 0° C. for 2 hours and then concentrated in vacuo. The crude material was stirred with hexanes (3 mL) and filtered. The filtrate was then concentrated in vacuo to afford the title compound, which was used for next step directly without further purification. LC/MS=207 [M+1].

Step 3: ethyl (R)-2-cyclopropyl-2-((R)-3-(5-((2,4-dimethoxybenzyl)amino)-7-methoxy-[1,2,4]triazolo[1,5-c]quinazolin-2-yl)piperidin-1-yl)acetate and ethyl (S)-2-cyclopropyl-2-((R)-3-(5-((2,4-dimethoxybenzyl)amino)-7-methoxy-[1,2,4]triazolo[1,5-d]quinazolin-2-yl)piperidin-1-yl)acetate To a three-neck flask (50 mL) was charged (±)-ethyl 2-bromo-2-cyclopropylacetate (460 mg, 2.23 mmol), (R)—N-(2,4-dimethoxybenzyl)-7-methoxy-2-(piperidin -3-yl)-[1,2,4]triazolo[1,5-c]quinazolin-5-amine (500 mg, 1.12 mmol), potassium carbonate (308 mg, 2.23 mmol), sodium iodide (5 mg) and N,N-dimethylformamide (10 mL). The suspension was heated at 80° C. for 6 hours. The reaction mixture was diluted with ethyl acetate (50 mL), washed with water (30 mL), dried (sodium sulfate), concentrated and purified by reverse phase HPLC (acetonitrile/water with 0.05% ammonium hydrogencarbonate) to afford the title compound. LC/MS=574 [M+1].

Step 4: (R)-2-cyclopropyl-2-((R)-3-(5-((2,4-dimethoxybenzyl)amino)-7-methoxy-[1,2,4]triazolo[1,5-c]quinazolin-2-yl)piperidin-1-yl)ethan-1-ol and (S)-2-cyclopropyl-2-((R)-3-(5-((2,4-dimethoxybenzyl)amino)-7-methoxy-[1,2,4]triazolo[1,5-d]quinazolin-2-yl)piperidin-1-yl)ethan-1-ol To a dried three-neck flask (50 mL) was charged a tetrahydrofuran solution (5 mL) of ethyl (R)-2-cyclopropyl-2-((R)-3-(5-((2,4-dimethoxybenzyl)amino)-7-methoxy-[1,2,4]triazolo[1,5-c]quinazolin-2-yl)piperidin-1-yl)acetate and ethyl (S)-2-cyclopropyl-2-((R)-3-(5-((2,4-dimethoxybenzyl)amino)-7-methoxy-[1,2,4]triazolo[1,5-c]quinazolin-2-yl)piperidin-1-yl)acetate (25 mg, 0.04 mmol). The solution was cooled to −20° C. under nitrogen. Then a tetrahydrofuran solution of diisobutylaluminium hydride (0.5 mL, 0.5 mmol) was added dropwise. Once the addition was completed, the reaction mixture was allowed to warm to room temperature and stirred at this temperature for 2 hours. The reaction mixture was quenched with methanol (2 mL). The resultant mixture was further diluted with water (15 mL) and dichloromethane (10 mL). The aqueous layer was extracted with dichloromethane (10 mL×2). The combined organic layers were dried (sodium sulfate), concentrated and purified by reverse phase HPLC (acetonitrile/water with 0.05% ammonium carbonate) to afford the title compound. LC/MS=533 [M+1].

Step 5: (R)-2-((R)-3-(5-amino-7-methoxy-[1,2,4]triazolo[1,5-c]quinazolin-2-yl)piperidin-1-yl)-2-cyclopropylethan-1-ol and (S)-2-((R)-3-(5-amino-7-methoxy-[1,2,4]triazolo[1,5-c]quinazolin-2-yl)piperidin-1-yl)-2-cyclopropylethan-1-ol To a three-neck flask (50 mL) was charged a dichloromethane solution (5 mL) of (R)-2-cyclopropyl-2-((R)-3-(5-((2,4-dimethoxybenzyl)amino)-7-methoxy-[1,2,4]triazolo[1,5-c]quinazolin-2-yl)piperidin-1-yl)ethan-1-ol and (S)-2-cyclopropyl-2-((R)-3-(5-((2,4-dimethoxybenzyl)amino)-7-methoxy-[1,2,4]triazolo[1,5-c]quinazolin-2-yl)pi-peridin-1-yl)ethan -1-ol (20 mg, 0.04 mmol) and trifluoroacetic acid (5 mL). The mixture was stirred at room temperature for 48 hours. The reaction mixture was diluted with dichloromethane (50 mL) and neutralized with aqueous saturated potassium carbonate solution. The organic layer was dried (sodium sulfate), concentrated and purified by reverse phase HPLC (acetonitrile/water with 0.05% ammonium carbonate) to afford the title compound. LC/MS=383 [M+1].

Step 6: 2-((R)-1-((R)-2-cyclopropyl-2-fluoroethyl)piperidin-3-yl)-7-methoxy-[1,2,4]triazolo[1,5-c]quinazolin-5-amine and 2-((R)-1-((S)-2-cyclopropyl-2-fluoroethyl)piperidin-3-yl)-7-methoxy-[1,2,4]triazolo[1,5-c]quinazolin-5-amine To a three-neck flask (50 mL) was charged a dichloromethane solution (5 mL) of (R)-2-((R)-3-(5-amino-7-methoxy-[1,2,4]triazolo[1,5-c]quinazolin-2-yl)piperidin-1-yl)-2-cyclopropylethan-1-ol and (S)-2-((R)-3-(5-amino-7-methoxy-[1,2,4]triazolo[1,5-c]quinazolin-2-yl)piperidin-1-yl)-2-cyclopropylethan-1-ol (11 mg, 0.03 mmol). (Diethylamino)sulfur trifluoride (8 mg, 0.04 mmol) was added at 0° C. The mixture was stirred at room temperature for 4 hours. The reaction mixture was diluted with dichloromethane (10 mL) and neutralized with aqueous saturated potassium carbonate solution. The organic layer was dried (sodium sulfate), concentrated and purified by reverse phase HPLC (acetonitrile/water with 0.05% ammonium carbonate) to afford the title compound. LC/MS=371 [M+1]. $^1$H-NMR (CDCl$_3$, 400 MHz) δ 7.96-7.93 (d, 1H), 7.38-7.33 (m, 1H), 7.16-7.13 (d, 1H), 6.16 (s, 2H), 4.06 (s, 3H), 3.40-3.33 (m, 2H), 3.06-2.85 (m, 3H), 2.61-2.51 (m, 1H), 2.28-2.22 (m, 2H), 1.85-1.71 (m, 3H), 1.25-1.04 (m, 2H), 0.65-0.32 (m, 4H). The mixture of the two stereoisomers was purified by chiral SFC (IC-H column, isopropanol/CO$_2$) to afford isomer A (faster eluting) and isomer B (slower eluting).

Example 25

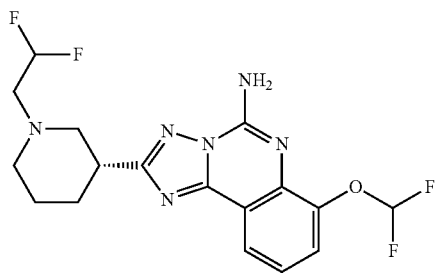 [SMILES: Nc1nc2c(OC(F)F)cccc2c2nc([C@@H]3CCCN(CC(F)F)C3)nn12]

(R)-2-(1-(2,2-difluoroethyl)piperidin-3-yl)-7-(difluoromethoxy)-[1,2,4]triazolo[1,5-c]quinazolin-5-amine Step 1: (R)-2-(1-(2,2-difluoroethyl)piperidin-3-yl)-N-(2,4-dimethoxybenzyl)-7-methoxy-[1,2,4]triazolo[1,5-c]quinazolin-5-amine To a sealed tube was added a mixture of (R)—N-(2,4-dimethoxybenzyl)-7-methoxy-2-(piperidin-3-yl)-[1,2,4]triazolo[1,5-c]quinazolin-5-amine (225 mg, 0.5 mmol), 2-bromo-1,1-difluoroethane (430 mg, 3.0 mmol), sodium iodide (40 mg, 0.25 mmol), potassium carbonate (140 mg, 1.0 mmol), and N,N-dimethylformamide (3 mL). The mixture was stirred at 50° C. for 16 hours. The resulting mixture was cooled to room temperature and poured into 30 mL of water. The aqueous layer was extracted with ethyl acetate (20 mL×3). The combined organic layer was dried (sodium sulfate), filtered and concentrated in vacuo to afford the title compound. LC/MS=513 [M+1].

Step 2: (R)-4-(((2-(1-(2,2-difluoroethyl)piperidin-3-yl)-7-hydroxy-[1,2,4]triazolo[1,5-c]quinazolin-5-yl)amino)methyl)benzene-1,3-diol To a dichloromethane solution (5 mL) of (R)-2-(1-(2,2-difluoroethyl)piperidin-3-yl)-N-(2,4-dimethoxybenzyl)-7-methoxy-[1,2,4]triazolo[1,5-c]quinazolin-5-amine (200 mg, 0.4 mmol) at room temperature was added a dichloromethane solution (0.5 M) of boron tribromide (5 mL, 2.5 mmol). After addition, the mixture was stirred at room temperature for 16 hours. The organic solvent was evaporated under reduced pressure to afford the title compound. LC/MS=471 [M+1].

Step 3: (R)-5-amino-2-(1-(2,2-difluoroethyl)piperidin-3-yl)-[1,2,4]triazolo[1,5-c]quinazolin-7-ol To a dichloromethane solution (5 mL) of (R)-4-(((2-(1-(2,2-difluoroethyl) piperidin-3-yl)-7-hydroxy-[1,2,4]triazolo[1,5-c]quinazolin-5-yl)amino)methyl)benzene-1,3-diol (500 mg, 1.06 mmol) at room temperature was added trifluoroacetic acid (5 mL). After addition, the mixture was stirred at room temperature for 48 hours. The pH of the mixture was adjusted to 7 with saturated aqueous potassium carbonate solution at 0° C. The aqueous layer was extracted with dichloromethane (15 mL×3), and the combined organic layers were dried (sodium sulfate), filtered, and concentrated in vacuo to afford the title compound. LC/MS=349 [M+1].

Step 4: (R)—N'-(2-(1-(2,2-difluoroethyl)piperidin-3-yl)-7-hydroxy-[1,2,4]triazolo[1,5-c]quinazolin-5-yl)-N,N-dimethylformimidamide To a 25 mL round bottom flask was added an ethanolic solution (2 mL) solution of (R)-5-amino-2-(1-(2,2-difluoroethyl)piperidin-3-yl)-[1,2,4]triazolo[1,5-c]quinazolin-7-ol (40 mg, 0.115 mmol) and N,N-dimethylformamide dimethylacetal (90 mg, 0.76 mmol). The mixture was stirred at room temperature for 3 hours. The organic solvent was evaporated under reduced pressure, and the residue was purified with prep-TLC, eluting with dichloromethane/methanol 100/1, to afford the title compound. LC/MS=404 [M+1].

Step 5: (R)—N'-(2-(1-(2,2-difluoroethyl)piperidin-3-yl)-7-(difluoromethoxy)-[1,2,4]triazolo[1,5-c]quinazolin-5-yl)-N,N-dimethylformimidamide To a sealed tube was added an acetonitrile solution (0.4 mL) of (R)—N'-(2-(1-(2,2-difluoroethyl)piperidin-3-yl)-7-hydroxy-[1,2,4]triazolo[1,5-c]quinazolin-5-yl)-N,N-dimethylformimidamide (20 mg, 0.050 mmol) and an aqueous solution (0.4 mL) of potassium hydroxide (58.4 mg, 1.04 mmol). The mixture was stirred at −78° C. followed by addition of 2-chloro-2,2-difluoro-1-phenylethanone (47.2 mg, 0.248 mmol). The mixture was then stirred at 80° C. for 18 hours. After the mixture was cooled to room temperature, 2 mL of water was added. The aqueous layer was extracted with dichloromethane (2 mL×3). The combined organic layers were dried (sodium sulfate), filtered and concentrated in vacuo. The residue was purified with prep-TLC, eluting with pet ether/ethyl acetate 1/1, to afford the title compound. LC/MS=453 [M+1].

Step 6: (R)-2-(1-(2,2-difluoroethyl)piperidin-3-yl)-7-(difluoromethoxy)-[1,2,4]triazolo[1,5-c]quinazolin-5-amine To a 10 mL round bottom flask was added (R)—N'-(2-(1-(2,2-difluoroethyl)piperidin-3-yl)-7-(difluoromethoxy)-[1,2,4]triazolo[1,5-c]quinazolin-5-yl)-N,N-dimethylformimidamide (180 mg, 0.12 mmol) and 1,4-dioxane solution (1.0 M, 2 mL) of hydrogen chloride. The mixture was stirred at room temperature for 18 hours. The resulting mixture was poured into aqueous saturated potassium carbonate solution (50 mL). The aqueous layer was extracted with ethyl acetate (30 mL×3). The combined organic layers were dried (sodium sulfate), filtered, and concentrated in vacuo. The residue was purified with prep-TLC, eluting with pet ether/ethyl acetate 1/1, to afford the title compound. LC/MS=399 [M+1]. $^1$H-NMR (CDCl$_3$, 400 MHz) δ 8.21 (d, 1H), 7.48 (d, 1H), 7.37 (t, 1H), 6.86 (t, 1H), 6.66 (bs, 2H), 6.10-5.80 (m, 1H), 3.36-3.28 (m, 2H), 2.98 (d, 1H), 2.89-2.81 (m, 2H), 2.66 (t, 1H), 2.40-2.33 (m, 1H), 2.25-2.23 (m, 1H), 1.87-1.68 (m, 3H).

Example 26

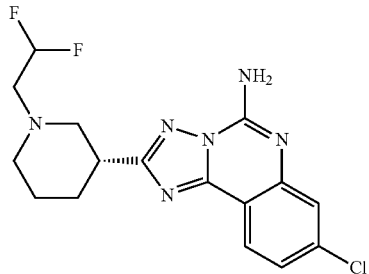 [SMILES: Nc1nc2cc(Cl)ccc2c2nc([C@@H]3CCCN(CC(F)F)C3)nn12]

(R)-8-chloro-2-(1-(2,2-difluoroethyl)piperidin-3-yl)-[1,2,4]triazolo[1,5-c]quinazolin-5-amine Step 1: tert-butyl (R)-3-(8-chloro-5-((2,4-dimethoxybenzyl)amino)-[1,2,4]triazolo[1,5-c]quinazolin-2-yl)piperidine-1-carboxylate The title compound was made by following the procedures described for INTERMEDIATE A1, substituting 2,4,7-trichloroquinazoline for 2,4-dichloro-8-methoxyquinazoline in Step 2. LC/MS=553 [M+1].

Step 2: (R)-8-chloro-2-(1-(2,2-difluoroethyl)piperidin-3-yl)-[1,2,4]triazolo[1,5-c]quinazolin-5-amine The title compound was made by following the procedures described for EXAMPLE 3, substituting tert-butyl (R)-3-(8-chloro-5-((2,4-dimethoxybenzyl)amino)-[1,2,4]tri-azolo[1,5-c]quinazolin-2-yl)piperidine-1-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate. LC/MS=333 [M+1]. ¹H-NMR (CDCl₃, 400 MHz) δ 8.34 (d, 1H), 7.65 (m, 2H), 7.41 (m, 1H), 6.34 (s, 2H), 5.95 (m, 1H), 3.32 (m, 2H), 2.99 (d, 1H), 2.84 (m, 2H), 2.64 (t, 1H), 2.34 (t, 1H), 2.24 (d, 1H), 1.81 (m, 3H).

Example 27

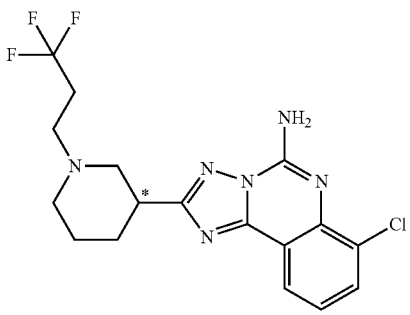 [SMILES: Nc1nc2c(Cl)cccc2c2nc(C3CCCN(CCC(F)(F)F)C3)nn12]

(±)-7-chloro-2-(1-(3,3,3-trifluoropropyl)piperidin-3-yl)-[1,2,4]triazolo[1,5-c]quinazolin-5-amine Step 1: (±)-tert-butyl 3-(7-chloro-5-((2,4-dimethoxybenzyl)amino)-[1,2,4]triazolo[1,5-c]quinazolin-2-yl)piperidine-1-carboxylate The title compound was made by following the procedures described for INTERMEDIATE A1, using a racemic mixture of 1-tert-butyl-3-ethyl piperidine-1,3-dicarboxylate instead of the R-enantiomer in Step 1 and substituting 2,4-dichloro-8-methoxyquinazoline for 2,4,8-trichloroquinazoline in Step 2. LC/MS=553 [M+].

Step 2: (±)-7-chloro-2-(1-(3,3,3-trifluoropropyl)piperidin-3-yl)-[1,2,4]triazolo[1,5-c]quinazolin-5-amine The title compound was made by following the procedures described for EXAMPLE 1, substituting (±)-tert-butyl 3-(7-chloro-5-((2,4-dimethoxybenzyl)amino)-[1,2,4]triazolo[1,5-c]quinazolin-2-yl)piperidine-1-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate. LC/MS=399 [M+1].

Example 28

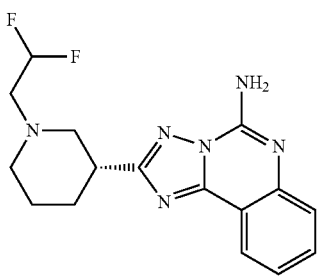 [SMILES: Nc1nc2ccccc2c2nc([C@@H]3CCCN(CC(F)F)C3)nn12]

(R)-2-(1-(2,2-difluoroethyl)piperidin-3-yl)-[1,2,4]triazolo[1,5-c]quinazolin-5-amine Step 1: (R)-2-(1-(2,2-difluoroethyl)piperidin-3-yl)-N-(2,4-dimethoxybenzyl)-[1,2,4]triazolo[1,5-c]quinazolin-5-amine An ethanolic solution (30 mL) of (R)-8-chloro-2-(1-(2,2-difluoroethyl)piperidin-3-yl)-N-(2,4-dimethoxybenzyl)-[1,2,4]triazolo[1,5-c]quinazolin-5-amine (100 mg, 0.19 mmol) with palladium on carbon (10%, 100 mg) was stirred at room temperature for 12 hours under hydrogen. The reaction mixture was filtered and concentrated in vacuo to afford the title compound. LC/MS=262 [M+1].

Step 2: (R)-2-(1-(2,2-difluoroethyl)piperidin-3-yl)-[1,2,4]triazolo[1,5-c]quinazolin-5-amine The title compound was made by following the procedures described in Step 3 for EXAMPLE 1, substituting (R)-2-(1-(2,2-difluoroethyl)piperidin-3-yl)-N-(2,4-dimethoxybenzyl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=333 [M+1]. ¹H-NMR (CDCl₃, 400 MHz) δ 8.34 (d, 1H), 7.65 (m, 2H), 7.41 (m, 1H), 6.34 (s, 2H), 5.95 (m, 1H), 3.32 (m, 2H), 2.99 (d, 1H), 2.84 (m, 2H), 2.64 (t, 1H), 2.34 (t, 1H), 2.24 (d, 1H), 1.81 (m, 3H).

Examples 29A, 29B, 29C, and 29D

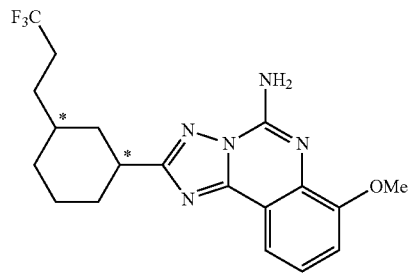 [SMILES: COc1cccc2c1nc(N)n1nc(C3CCCC(CCC(F)(F)F)C3)nc21]

7-methoxy-2-(3-(3,3,3-trifluoropropyl)cyclohexyl)-[1,2,4]triazolo[1,5-c]quinazolin-5-amine Step 1: (±)-3-(5-((2,4-dimethoxybenzyl)amino)-7-methoxy-[1,2,4]triazolo[1,5-c]quinazolin-2-yl)cyclohexan-1-one To an ethyl acetate (10 mL) solution of 3-(5-((2,4-dimethoxybenzyl)amino)-7-methoxy-[1,2,4]triazolo[1,5-c]quinazolin-2-yl)cyclohexan-1-ol (500 mg, 1.1 mmol) was added 2-iodoxybenzoic acid (915 mg, 3.2 mmol) and acetic acid (10 mL). The reaction mixture was heated at 50° C. for 12 hours, filtered, and concentrated in vacuo. The residue was purified by reverse phase HPLC (acetonitrile/water with 0.05% ammonium hydrogencarbonate) to afford the title compound. LC/MS=462 [M+1].

Step 2: (±)-N-(2,4-dimethoxybenzyl)-7-methoxy-2-(3-(3,3,3-trifluoropropylidene)cyclohexyl)-[1,2,4]triazolo[1,5-c]quinazolin-5-amine To a flame-dried three-necked flask (50 mL) was charged with (±)-3-(5-((2,4-dimethoxybenzyl)amino)-7-methoxy-[1, 2,4]triazolo[1,5-c]quinazolin-2-yl)cyclohexan-1-one (46 mg, 0.1 mmol) and dry tetrahydrofuran (15 mL). The mixture was bubbled with nitrogen for 1 minute before triphenyl(3,3,3-trifluoropropylidene)-$\lambda^5$-phosphane (438 mg, 1.0 mmol) was added. The suspension was heated at 80° C. for 10 hours and concentrated in vacuo. The residue was purified by reverse phase HPLC (acetonitrile/water with 0.05% ammonium hydrogencarbonate) to afford the title compound. LC/MS=542 [M+1].

Step 3: (±)-7-methoxy-2-(3-(3,3,3-trifluoropropylidene)cyclohexyl)-[1,2,4]triazolo[1,5-c]quinazolin-5-amine The title compound was made by following the procedures described in Step 3 for EXAMPLE 1, substituting (±)—N-(2,4-dimethoxybenzyl)-7-methoxy-2-(3-(3,3,3-trifluoropropylidene)cyclohexyl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=392 [M+1].

Step 4: 7-methoxy-2-(3-(3,3,3-trifluoropropyl)cyclohexyl)-[1,2,4]triazolo[1,5-c]quinazolin-5-amine To a three-necked flask (50 mL) was charged an ethyl acetate solution (15 mL) of (±)-7-methoxy-2-(3-(3,3,3-trifluoropropylidene)cyclohexyl)-[1,2,4]triazolo[1,5-c]quinazolin-5-amine (160 mg, 0.4 mmol) and palladium on carbon (10%, 50 mg). The reaction mixture was stirred at 40° C. for 4 hours under hydrogen, filtered, and concentrated in vacuo. The residue was purified by reverse phase HPLC (acetonitrile/water with 0.05% ammonium hydrogencarbonate) to afford the title compound as a mixture of diastereomers. LC/MS=394 [M+1]. Chiral resolution of the four diastereomers was achieved by chiral preparative HPLC/SFC. Isomer 29A: HPLC conditions: AY-H column (250*4.6 mm, 5 μm); n-hexane (0.1% diethylamine)/ethanol (0.1% diethylamine)=95/5 as eluent; 1.0 mL/min as flow rate; RT=10.03 min. Isomer 29B: HPLC conditions: AY-H column (250*4.6 mm, 5 μm); n-hexane (0.1% diethylamine)/ethanol (0.1% diethylamine)=95/5 as eluent; 1.0 mL/min as flow rate; RT=10.82 min. Isomer 29C: SFC conditions: IC column (250*4.6 mm, 5 μm); 1.2 mL/min as isopropanol flow rate; 1.8 mL/min as supercritical carbon dioxide flow rate; RT=5.47 min. Isomer 29D: SFC conditions: IC column (250*4.6 mm, 5 μm); 1.2 mL/min as isopropanol flow rate; 1.8 mL/min as supercritical carbon dioxide flow rate; RT=8.01 min.

Examples 30A, 30B, 30C, and 30D

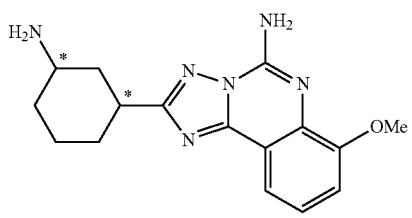 [SMILES: COc1cccc2c1nc(N)n1nc(C3CCCC(N)C3)nc21]

2-(3-aminocyclohexyl)-7-methoxy-[1,2,4]triazolo[1,5-c]quinazolin-5-amine

Step 1: (±)-3-(5-((2,4-dimethoxybenzyl)amino)-7-methoxy-[1,2,4]triazolo[1,5-c]quinazolin-2-yl)cyclohexan-1-one oxime To a 50 mL round bottom flask was added an ethanolic solution (10 mL) of (±) -3-(5-((2,4-dimethoxybenzyl)amino)-7-methoxy-[1,2,4]triazolo[1,5-c]quinazolin-2-yl)cyclohexan-1-one (300 mg, 0.65 mmol), hydroxylamine hydrochloride (90 mg, 1.3 mmol), and pyridine (103 mg, 1.3 mmol). The reaction mixture was stirred at 80° C. for 2 hours and concentrated in vacuo to afford the title compound. LC/MS=477 [M+1].

Step 2: 2-(3-aminocyclohexyl)-N-(2,4-dimethoxybenzyl)-7-methoxy-[1,2,4]triazolo[1,5-c]quinazolin-5-amine To a 50 mL round bottom flask was added a methanolic solution (20 mL) of (±) -3-(5-((2,4-dimethoxybenzyl)amino)-7-methoxy-[1,2,4]triazolo[1,5-c]quinazolin-2-yl)cyclohexan-1-one oxime (300 mg, 0.63 mmol) and Raney nickel (100 mg). The reaction mixture was stirred under hydrogen at ambient conditions for 18 hours. After filtration, the reaction mixture was concentrated in vacuo, and the residue was purified by reverse phase HPLC (acetonitrile/water with 0.05% trifluoroacetic acid) to afford the title compound as the trifluoroacetate salt. LC/MS=463 [M+1].

Step 3: 2-(3-aminocyclohexyl)-7-methoxy-[1,2,4]triazolo[1,5-c]quinazolin-5-amine The title compound was made by following the procedures described in Step 3 for EXAMPLE 1, substituting 2-(3-aminocyclohexyl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=313 [M+1]. Chiral resolution of the four diastereomers was achieved by chiral preparative HPLC (AY-H column, 250*4.6 mm, 5 μm; n-hexane (0.1% diethylamine)/ethanol (0.1% diethylamine) 85/15 as eluent; 1.0 mL/min as flow rate). Isomer 30A: RT=11.44 min. Isomer 30B: RT=15.02 min. Isomer 30C: RT=16.18 min. Isomer 30D: RT=22.24 min.

Example 31

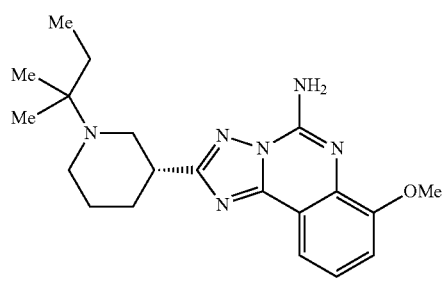 [SMILES: CCC(C)(C)N1CCC[C@@H](c2nc3c4cccc(OC)c4nc(N)n3n2)C1]

(R)-7-methoxy-2-(1-(tert-pentyl)piperidin-3-yl)-[1,2,4]triazolo[1,5-c]quinazolin-5-amine

Step 1: (R)-2-(3-(5-((2,4-dimethoxybenzyl)amino)-7-methoxy-[1,2,4]triazolo[1,5-c]quinazolin-2-yl)piperidin-1-yl)-2-methylpropanenitrile To a microwave vial was added an acetone solution (2 mL) of 2-hydroxy-2-methylpropanenitrile (260 mg, 0.40 mmol) and (R)—N-(2,4-dimethoxybenzyl)-7-methoxy-2-(piperidin-3-yl)-[1,2,4]triazolo[1,5-c]quinazolin-5-amine (90 mg, 0.2 mmol). It was capped and irradiated with microwaves at 80° C. for 3 hours. The reaction mixture was concentrated in vacuo to afford the title compound, which was used in the subsequent reaction without purification. LC/MS=516 [M+1].

Step 2: (R)—N-(2,4-dimethoxybenzyl)-7-methoxy-2-(1-(tert-pentyl)piperidin-3-yl)-[1,2,4]triazolo[1,5-c]quinazolin-5-amine To a flame-dried three-necked flask was charged (R)-2-(3-(5-((2,4-dimethoxybenzyl)amino)-7-methoxy-[1,2,4]triazolo[1,5-c]quinazolin-2-yl)piperidin-1-yl)-2-methylpropanenitrile (100 mg, 0.19 mmol) and diethyl ether (5 mL). The reaction mixture was cooled to 0° C. under nitrogen. Ethylmagnesium bromide (1.0 M in diethyl ether; 4 mL, 4 mmol) was then added dropwise. Once the addition was completed, the reaction mixture was stirred at 0° C. for 30 minutes and quenched with water (10 mL). The resulting mixture was extracted with dichloromethane (3×10 mL), and the combined organic layers were dried (sodium sulfate), filtered, and concentrated in vacuo. The crude product was purified by prep-TLC (20:1 dichloromethane/methanol) to yield the title compound. LC/MS=519 [M+1].

Step 3: (R)-7-methoxy-2-(1-(tert-pentyl)piperidin-3-yl)-[1,2,4]triazolo[1,5-c]quinazolin-5-amine The title compound was made by following the procedures described in Step 3 for EXAMPLE 1, substituting (R)—N-(2,4-dimethoxybenzyl)-7-methoxy-2-(1-(tert-pentyl)piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=369 [M+1]. $^1$H-NMR (CDCl$_3$, 400 MHz) δ 7.96 (d, 1H), 7.35 (t, 1H), 7.14 (d, 1H), 6.24 (s, 2H), 4.06 (s, 3H), 3.33 (d, 1H), 3.19-3.02 (m, 1H), 3.01-2.99 (m, 1H), 2.44 (t, 1H), 2.18 (d, 2H), 1.82 (s, 1H), 1.75-1.67 (m, 2H), 1.48 (d, 2H), 0.98 (s, 6H), 0.86 (t, 3H).

Examples 32A and 32B

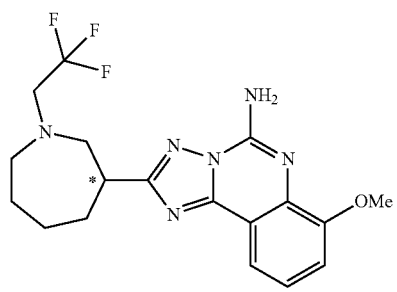 [SMILES: COc1cccc2c1nc(N)n1nc(C3CCCCN(CC(F)(F)F)C3)nc21]

7-methoxy-2-(1-(2,2,2-trifluoroethyl)azepan-3-yl)-[1,2,4]triazolo[1,5-c]quinazolin-5-amine

Step 1: 2-(azepan-3-yl)-N-(2,4-dimethoxybenzyl)-7-methoxy-[1,2,4]triazolo[1,5-c]quinazolin-5-amine The title compound was made by following the procedures described in Step 1 for EXAMPLE 1, substituting (±)-tert-butyl 3-(5-((2,4-dimethoxybenzyl)amino)-7-methoxy-[1,2,4]triazolo[1,5-c]quinazolin-2-yl)azepane-1-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate. Chiral resolution of the two enantiomers was achieved by chiral preparative SFC (Regiscell column (4.6*250 mm, 5 μm); methanol (0.2% diethylamine) 0.9 mL/min; supercritical carbon dioxide 2.1 mL/min). Isomer A: RT=3.75 min. Isomer B: RT=4.3 min.

Step 2: 7-methoxy-2-(1-(2,2,2-trifluoroethyl)azepan-3-yl)-[1,2,4]triazolo[1,5-c]quinazolin-5-amine The title compound was made by following the procedures described for EXAMPLE 23, substituting the resolved enantiomers of 2-(azepan-3-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(piperidin-3-yl)-[1,2,4]triazolo[1,5-c]quinazolin-5-amine. LC/MS=395 [M+1]. Isomer 32A: RT=3.75 min (OJ-H column (4.6*250 mm, 5 μm); methanol (0.1% diethylamine) 0.45 mL/min; supercritical carbon dioxide 2.55 mL/min). Isomer 32B: RT=2.04 min (OJ-H column (4.6*250 mm, 5 μm); methanol (0.1% diethylamine) 0.9 mL/min; supercritical carbon dioxide 2.1 mL/min).

Examples 33A and 33B

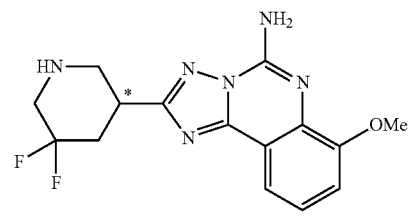 [SMILES: COc1cccc2c1nc(N)n1nc(C3CNCC(F)(F)C3)nc21]

2-(5,5-difluoropiperidin-3-1-yl)-7-methoxy-[1,2,4]triazolo[1,5-c]quinazolin-5-amine

Step 1: (±)-1-tert-butyl 3-methyl 5-oxopiperidine-1,3-dicarboxylate

To an anhydrous dichloromethane solution (15 mL) of 1-tert-butyl 3-methyl 5-hydroxypiperidine-1,3-dicarboxylate (1 g, 3.8 mmol) at 0° C. was added 1,1,1-triacetoxy-1,1-dihydro-1,2-benziodoxol-3(1H)-one (3.2 g, 7.6 mmol). The mixture was stirred at room temperature under nitrogen for 20 hours, then poured into water (50 mL) and extracted with dichloromethane (3×20 mL). The combined organic fractions were dried (sodium sulfate), filtered, and concentrated in vacuo to afford the title compound, which was used in the subsequent step without further purification.

Step 2: (±)-1-tert-butyl 3-methyl 5,5-difluoropiperidine-1,3-dicarboxylate

To a 50 mL round bottomed flask at 0° C. was charged a dichloromethane solution (15 mL) of 1-tert-butyl 3-methyl 5-oxopiperidine-1,3-dicarboxylate (900 mg, 3.5 mmol) and diethylaminosulfur trifluoride (0.92 mL, 7.0 mmol). The resulting mixture was stirred at 30° C. for 16 hours. Then pH value was adjusted to 7.0 with saturated aqueous sodium hydrogencarbonate solution. The mixture was extracted with dichloromethane (3×30 mL), and the combined organic fractions were washed with brine (40 mL), dried (magnesium sulfate), filtered, and concentrated in vacuo to afford the crude product. Purification by column chromatography over silica gel afforded the title compound. LC/MS=280 [M+1].

Step 3: (±)-tert-butyl 5-(5-((2,4-dimethoxybenzyl)amino)-7-methoxy-[1,2,4]triazolo[1,5-c]quinazolin-2-yl)-3,3-difluoropiperidine-1-carboxylate The title compound was made by following the procedures described for INTERMEDIATE A1, substituting (±)-1-tert-butyl 3-methyl 5,5-difluoropiperidine-1,3-dicarboxylate for (R)-1-tert-butyl-3-ethyl piperidine-1,3-dicarboxylate in Step 1. LC/MS=585 [M+1].

Step 4: 2-(5,5-difluoropiperidin-3-yl)-7-methoxy-[1,2,4]triazolo[1,5-c]quinazolin-5-amine The title compound was made by following the procedures described in Step 1 for EXAMPLE 1, substituting (±)-tert-butyl 5-(5-((2,4-dimethoxybenzyl)amino)-7-methoxy-[1,2,4]triazolo[1,5-c]quinazolin-2-yl)-3,3-difluoropiperidine-1-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate. LC-MS=335 [M+1]. Chiral resolution of the two enantiomers was achieved by chiral preparative SFC. Isomer 34A: RT=5.31 min (AD-H column (4.6*250 mm, 5 μm); ethanol (0.1% diethylamine) 1.05 mL/min; supercritical carbon dioxide 1.95 mL/min). Isomer 34B: RT=6.55 min (AD-H column (4.6*250 mm, 5 μm); ethanol (0.1% diethylamine) 1.05 mL/min; supercritical carbon dioxide 1.95 mL/min).

Examples 34A and 34B

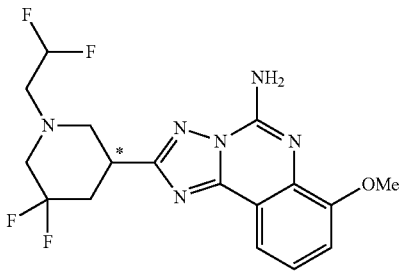 [SMILES: COc1cccc2c1nc(N)n1nc(C3CN(CC(F)F)CC(F)(F)C3)nc21]

2-(1-(2,2-difluoroethyl)-5,5-difluoropiperidin-3-yl)-7-methoxy-[1,2,4]triazolo[1,5-c]quinazolin-5-amine To a 20 mL sealed tube was charged a N,N-dimethylformamide solution (3 mL) of 2-(5,5-difluoropiperidin-3-yl)-7-methoxy-[1,2,4]triazolo[1,5-c]quinazolin-5-amine (150 mg, 0.45 mmol), 2-bromo-1,1-difluoroethane (646 mg, 4.5 mmol), potassium carbonate (124 mg, 0.9 mmol) and sodium iodide (8 mg, 0.05 mmol). The resulting mixture was heated at 50° C. for 16 hours. The solvent was evaporated under reduced pressure, and the residue was purified by reverse phase HPLC (acetonitrile/water with 0.05% ammonium hydrogencarbonate) to afford the title compound. LC-MS=399 [M+1]. Chiral resolution of the two enantiomers was achieved by chiral preparative SFC. Isomer 34A: RT=2.98 min (AD-H column (4.6*250 mm, 5 μm); methanol (0.1% diethylamine) 1.05 mL/min; supercritical carbon dioxide 1.95 mL/min). Isomer 34B: RT=3.82 min (AD-H column (4.6*250 mm, 5 μm); methanol (0.1% diethylamine) 1.05 mL/min; supercritical carbon dioxide 1.95 mL/min).

Examples 35A, 35B, 35C, and 35D

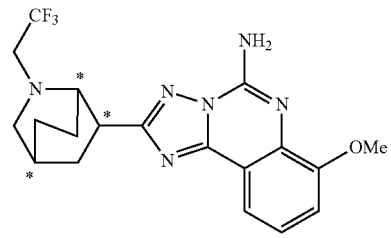 [SMILES: COc1cccc2c1nc(N)n1nc(C3CC4CCC3N(CC(F)(F)F)C4)nc21]

7-methoxy-2-(2-(2,2,2-trifluoroethyl)-2-azabicyclo[2.2.2]octan-6-yl)-[1,2,4]triazolo[1,5-c]quinazolin-5-amine

Step 1: 2-(2-azabicyclo[2.2.2]octan-6-yl)-N-(2,4-dimethoxybenzyl)-7-methoxy-[1,2,4]triazolo[1,5-c]quinazolin-5-amine The title compound was made by following the procedures described in Step 1 for EXAMPLE 1, substituting tert-butyl 6-(5-((2,4-dimethoxybenzyl)amino)-7-methoxy-[1,2,4]triazolo[1,5-c]quinazolin-2-yl)-2-azabicyclo[2.2.2]octane-2-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate.

Step 2: 7-methoxy-2-(2-(2,2,2-trifluoroethyl)-2-azabicyclo[2.2.2]octan-6-yl)-[1,2,4]triazolo[1,5-c]quinazolin-5-amine The title compound was made as a mixture of diastereomers by following the procedures described for EXAMPLE 23, substituting 2-(2-azabicyclo[2.2.2]octan-6-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(piperidin-3-yl)-[1,2,4]triazolo[1,5-c]quinazolin-5-amine in Step 1. LC/MS=407 [M+1]. Chiral resolution of the four diastereomers was achieved by chiral preparative SFC (OJ-H column; methanol (0.1% diethylamine) 0.3 mL/min; supercritical carbon dioxide 2.7 mL/min). Isomer 35A: RT=4.46 min. Isomer 35B: RT=5.64 min. Isomer 35C: RT=6.45 min. Isomer 35D: RT=6.86 min.

Example 36

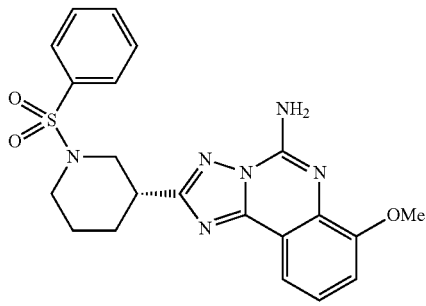 [SMILES: COc1cccc2c1nc(N)n1nc([C@@H]3CCCN(S(=O)(=O)c4ccccc4)C3)nc21]

(R)-7-methoxy-2-(1-(phenylsulfonyl)piperidin-3-yl)-[1,2,4]triazolo[1,5-c]quinazolin-5-amine Step 1: (R)—N-(2,4-dimethoxybenzyl)-7-methoxy-2-(1-(phenylsulfonyl)piperidin-3-yl)-[1,2,4]triazolo[1,5-c]quinazolin-5-amine To a dichloromethane solution (5.0 mL) of (R)—N-(2,4-dimethoxybenzyl)-7-methoxy-2-(piperidin-3-yl)-[1,2,4]triazolo[1,5-c]quinazolin-5-amine (80 mg, 0.16 mmol) at 0° C. was added benzenesulfonyl chloride (36 mg, 0.2 mmol) and triethylamine (36 mg, 0.36 mmol). The mixture was stirred at room temperature for 1 hour. Methanol (5.0 mL) was added and the solvent was removed. Then water (10 mL) was added, and the mixture was extracted with dichloromethane (3×20 mL). The combined organic fractions were washed with brine (30 mL), dried (sodium sulfate), filtered and concentrated in vacuo to afford the title compound, which was used in the subsequent reaction without further purification. LC/MS=589 [M+1].

Step 2: (R)-7-methoxy-2-(1-(phenylsulfonyl)piperidin-3-yl)-[1,2,4]triazolo[1,5-c]quinazolin-5-amine The title compound was made by following the procedures described in Step 3 for EXAMPLE 1, substituting (R)—N-(2,4-dimethoxybenzyl)-7-methoxy-2-(1-(phenylsulfonyl)piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=439 [M+1]. $^1$H-NMR (CD$_3$OD-d$_4$, 400 MHz) δ 7.74-7.70 (m, 3H), 7.57-7.47 (m, 3H), 7.25 (t, 1H), 7.15 (d, 1H), 4.04-4.00 (m, 1H), 3.91 (s, 3H), 3.68-3.65 (m, 1H), 3.19-3.15 (m, 1H), 2.71-2.66 (m, 1H), 2.44-2.38 (m, 1H), 2.14-2.11 (m, 1H), 1.88-1.84 (m, 1H), 1.84-1.61 (m, 2H).

Example 37

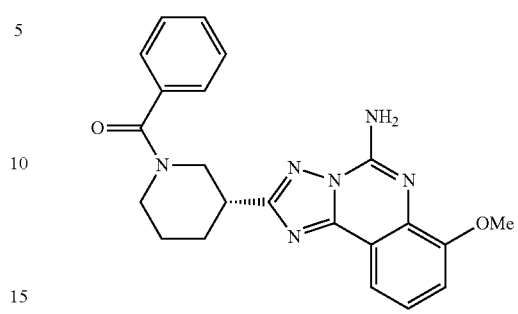

(R)-(3-(5-amino-7-methoxy-[1,2,4]triazolo[1,5-c]quinazolin-2-yl)piperidin-1-yl)(phenyl)methanone Step 1: (R)-(3-(5-((2,4-dimethoxybenzyl)amino)-7-methoxy-[1,2,4]triazolo[1,5-c]quinazolin-2-yl)piperidin-1-yl)(phenyl)methanone Benzoyl chloride (47 mg, 0.33 mmol) was added dropwise in a stirred dichloromethane solution (2 mL) of (R)—N-(2,4-dimethoxybenzyl)-7-methoxy-2-(piperidin-3-yl)-[1,2,4]triazolo[1,5-c]quinazolin-5-amine (100 mg, 0.22 mmol) and triethylamine (44 mg, 0.44 mmol) at 0° C. The reaction mixture was stirred at room temperature for 2 hours. The mixture was poured into aqueous sodium hydrogencarbonate solution (15 mL), extracted with dichloromethane (25 mL×3), dried (magnesium sulfate) and concentrated to afford the title compound, which was used in the subsequent step without further purification. LC/MS=553 [M+1].

Step 2: (R)-(3-(5-amino-7-methoxy-[1,2,4]triazolo[1,5-c]quinazolin-2-yl)piperidin-1-yl)(phenyl)methanone The title compound was made by following the procedures described in Step 3 for EXAMPLE 1, substituting (R)-(3-(5-((2,4-dimethoxybenzyl)amino)-7-methoxy-[1,2,4]triazolo[1,5-c]quinazolin-2-yl)piperidin-1-yl)(phenyl)methanone for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=403 [M+1]. $^1$H-NMR (DMSO-d$_6$, 400 MHz) δ 7.88-7.58 (m, 3H), 7.52-7.12 (m, 7H), 4.61 (d, 1H), 3.90 (s, 3H), 3.71-3.44 (m, 1H), 3.16 (s, 3H), 2.26 (s, 1H), 2.04-1.59 (m, 3H).

The following examples in Table 4 were prepared similarly as EXAMPLE 37 starting from the appropriate acid chlorides:

TABLE 4

| Ex | Structure | IUPAC Name | MS (M + 1) |
|---|---|---|---|
| 38 | (structure shown) | 2-((3R)-1-(2,2-dimethylpropanoyl)piperidin-3-yl)-7-methoxy[1,2,4]triazolo[1,5-c]quinazolin-5-amine | 383 |

TABLE 4-continued

| Ex | Structure | IUPAC Name | MS (M + 1) |
|---|---|---|---|
| 39 | 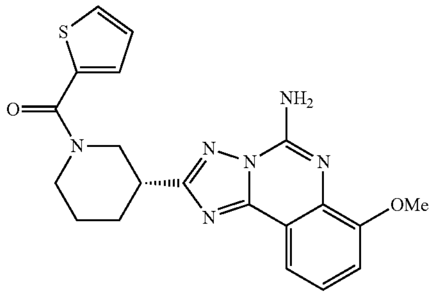 [SMILES: COc1cccc2c1nc(N)n1nc([C@@H]3CCCN(C(=O)c4cccs4)C3)nc21] | 7-methoxy-2-((3R)-1-(thiophen-2-ylcarbonyl)piperidin-3-yl)[1,2,4]triazolo[1,5-c]quinazolin-5-amine | 409 |
| 40 | 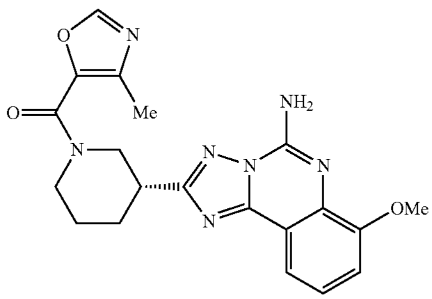 [SMILES: COc1cccc2c1nc(N)n1nc([C@@H]3CCCN(C(=O)c4ocnc4C)C3)nc21] | 7-methoxy-2-((3R)-1-((4-methyl-1,3-oxazol-5-yl)carbonyl)piperidin-3-yl)[1,2,4]triazolo[1,5-c]quinazolin-5-amine | 408 |
| 41 | 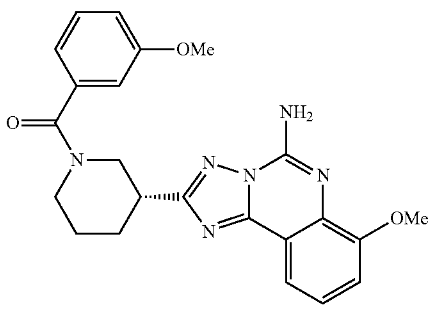 [SMILES: COc1cccc(C(=O)N2CCC[C@@H](c3nc4c5cccc(OC)c5nc(N)n4n3)C2)c1] | 7-methoxy-2-((3R)-1-((3-methoxyphenyl)carbonyl)piperidin-3-yl)[1,2,4]triazolo[1,5-c]quinazolin-5-amine | 433 |

Example 42

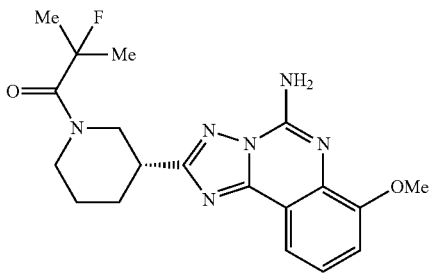 [SMILES: COc1cccc2c1nc(N)n1nc([C@@H]3CCCN(C(=O)C(C)(C)F)C3)nc21]

(R)-1-(3-(5-amino-7-methoxy-[1,2,4]triazolo[1,5-c]quinazolin-2-yl)piperidin-1-yl)-2-fluoro-2-methylpropan-1-one Step 1: (R)-1-(3-(5-((2,4-dimethoxybenzyl)amino)-7-methoxy-[1,2,4]triazolo[1,5-c]quinazolin-2-yl)piperidin-1-yl)-2-fluoro-2-methylpropan-1-one To a 100 mL round bottom flask with a N,N-dimethylformamide solution (16.0 mL) of (R)—N-(2,4-dimethoxybenzyl)-7-methoxy-2-(piperidin-3-yl)-[1,2,4]triazolo[1,5-c]quinazolin-5-amine (400 mg, 0.89 mmol) was added 2-fluoro-2-methylpropanoic acid (95 mg, 0.89 mmol), 1-[bis(dimethylamino)methylene]-1H-1,2,3-triazolo[4,5-b]pyridinium 3-oxid hexafluorophosphate (339 mg, 0.89 mmol), and N,N-diisopropylethylamine (231 mg, 1.8 mmol). The resulting mixture was stirred at 25° C. for 4 hours. Water (20 mL) was added, and the mixture was extracted with ethyl acetate (3×30 mL). The combined organic fractions were washed with brine (50 mL), dried (sodium sulfate), filtered, and concentrated in vacuo to afford the title compound, which was used in the subsequent step without further purification. LC/MS=537 [M+1].

Step 2: (R)-1-(3-(5-amino-7-methoxy-[1,2,4]triazolo[1,5-c]quinazolin-2-yl)piperidin-1-yl)-2-fluoro-2-methylpropan-1-one The title compound was made by following the procedures described in Step 3 for EXAMPLE 1, substituting (R)-1-(3-(5-((2,4-dimethoxybenzyl)amino)-7-methoxy-[1,2,4]triazolo[1,5-c]quinazolin-2-yl)piperidin-1-yl)-2-fluoro-2-methylpropan-1-one_for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=387 [M+1]. $^1$H-NMR (CD$_3$OD-d$_4$, 400 MHz) δ 7.85 (d, 1H), 7.38-7.34 (m, 1H), 7.27-7.25 (m, 1H), 4.80-4.79 (m, 1H), 4.45-4.46

(m, 1H), 4.02 (s, 3H), 3.41-3.33 (m, 1H), 3.19-3.17 (m, 2H), 2.39-2.36 (m, 1H), 2.06-1.97 (m, 2H), 1.75-1.61 (m, 7H).

Example 43

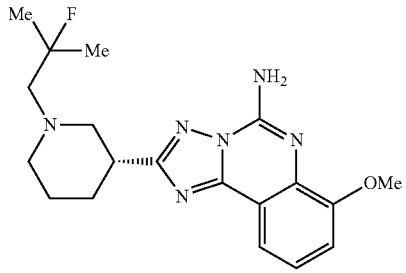 [SMILES: COc1cccc2c1nc(N)n1nc([C@@H]3CCCN(CC(C)(C)F)C3)nc21]

(R)-2-(1-(2-fluoro-2-methylpropyl)piperidin-3-yl)-7-methoxy-[1,2,4]triazolo[1,5-c]triazolo[1,5-c]quinazolin-5-amine To a 50 mL round bottom flask with a tetrahydrofuran solution (20 mL) of (R)-1-(3-(5-amino-7-methoxy-[1,2,4]triazolo[1,5-c]quinazolin-2-yl)piperidin-1-yl)-2-fluoro-2-methylpropan-1-one (110 mg, 0.29 mmol) at 0° C. was added dropwise borane-tetrahydrofuran complex (245 mg, 2.85 mmol). The reaction solution was stirred at room temperature for 16 hours. Then the reaction was quenched with methanol (2.0 mL) and the solvent was removed. The residue was purified by reverse phase HPLC (acetonitrile/water with 0.05% ammonium hydrogencarbonate) to afford the title compound. LC/MS=373 [M+1]. $^1$H-NMR (CD$_3$OD-d$_4$, 400 MHz) δ 7.87 (dd, 1H), 7.37 (t, 1H), 7.27-7.26 (m, 1H), 4.02 (s, 3H), 3.37 (m, 1H), 3.30-3.28 (m, 1H), 3.04-3.01 (m, 1H), 2.58-2.51 (m, 3H), 2.26-2.21 (m, 2H), 1.85-1.77 (m, 3H), 1.41 (s, 3H), 1.35 (s, 3H).

Example 44

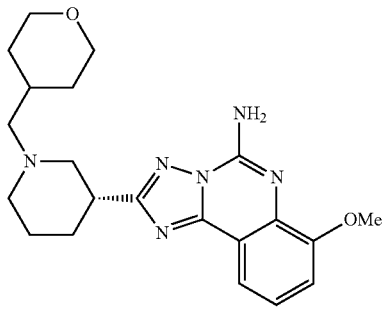 [SMILES: COc1cccc2c1nc(N)n1nc([C@@H]3CCCN(CC4CCOCC4)C3)nc21]

(R)-7-methoxy-2-(1-((tetrahydro-2H-pyran-4-yl)methyl)piperidin-3-yl)-[1,2,4]triazolo[1,5-c]quinazolin-5-amine Step 1: (R)—N-(2,4-dimethoxybenzyl)-7-methoxy-2-(1-((tetrahydro-2H-pyran-4-yl)methyl)piperidin-3-yl)-[1,2,4]triazolo[1,5-d]quinazolin-5-amine To a 50 mL round bottom flask with a N,N-dimethylformamide solution (3 mL) of (R)—N-(2,4-dimethoxybenzyl)-7-methoxy-2-(piperidin-3-yl)-[1,2,4]triazolo[1,5-c]quinazolin-5-amine (120 mg, 0.27 mmol) was charged tetrahydro-2H-pyran-4-carbaldehyde (61 mg, 0.54 mmol), polymer supported cyanoborohydride (232 mg, 0.54 mmol), and 2 drops of acetic acid. The reaction mixture was heated at 50° C. for 48 hours and filtered. The filtrate was diluted with ethyl acetate (30 mL), washed with brine (3×20 mL), dried (sodium sulfate), filtered and concentrated in vacuo. The residue was purified by reverse phase HPLC (acetonitrile/water with 0.05% ammonium hydrogencarbonate) to afford the title compound. LC/MS=547 [M+1].

Step 2: (R)-7-methoxy-2-(1-((tetrahydro-2H-pyran-4-yl)methyl)piperidin-3-yl)-[1,2,4]triazolo[1,5-c]quinazolin-5-amine The title compound was made by following the procedures described in Step 3 for EXAMPLE 1, substituting (R)—N-(2,4-dimethoxybenzyl)-7-methoxy-2-(1-((tetrahydro-2H-pyran -4-yl)methyl)piperidin-3-yl)-[1,2,4]triazolo[1,5-c]quinazolin-5-amine for (R)—N-(2,4-dimethoxybenzyl)-7-methoxy-2-(1-(3,3,3-trifluoropropyl) piperidin-3-yl)-[1,2,4]triazolo[1,5-c]quinazolin-5-amine. LC/MS=397 [M+1]. $^1$H-NMR (CDCl$_3$, 400 MHz) δ 7.95 (d, 1H), 7.37 (t, 1H), 7.15 (d, 1H), 5.91 (s, 2H), 4.06 (s, 3H), 3.96 (t, 2H), 3.39 (t, 2H), 3.24-3.22 (m, 2H), 2.88-2.86 (m, 1H), 2.35-2.32 (m, 1H), 2.26-2.21 (m, 3H), 2.07-2.02 (m, 1H), 1.81-1.78 (m, 2H), 1.77-1.67 (m, 4H), 1.28-1.21 (m, 2H).

The following examples in Table 5 were prepared similarly as EXAMPLE 44 starting from the appropriate aldehydes or ketones:

TABLE 5

| Ex | Structure | IUPAC Name | MS (M + 1) |
|---|---|---|---|
| 45 | 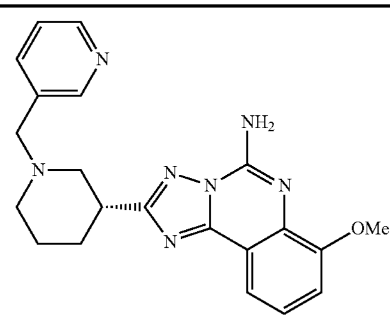 | 7-methoxy-2-((3R)-1-(pyridin-3-ylmethyl)piperidin-3-yl)[1,2,4]triazolo[1,5-c]quinazolin-5-amine | 390 |

TABLE 5-continued

| Ex | Structure | IUPAC Name | MS (M + 1) |
|---|---|---|---|
| 46 | 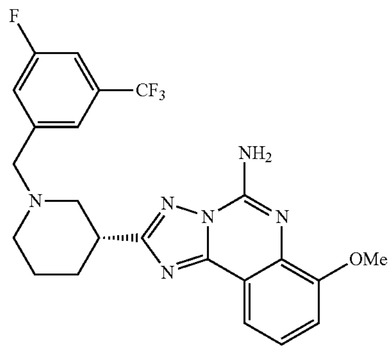 [SMILES: COc1cccc2c1nc(N)n1nc([C@@H]3CCCN(Cc4cc(F)cc(C(F)(F)F)c4)C3)nc21] | 2-((3R)-1-[3-fluoro-5-(trifluoromethyl)benzyl)piperidin-3-yl)-7-methoxy[1,2,4]triazolo[1,5-c]quinazolin-5-amine | 475 |
| 47 | 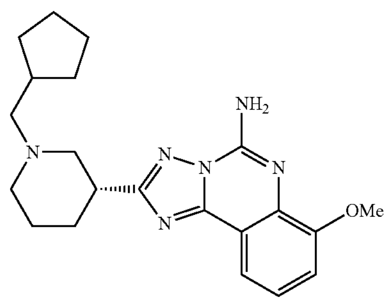 [SMILES: COc1cccc2c1nc(N)n1nc([C@@H]3CCCN(CC4CCCC4)C3)nc21] | 2-((3R)-1-(cyclopentylmethyl)piperidin-3-yl)-7-methoxy[1,2,4]triazolo[1,5-c]quinazolin-5-amine | 381 |
| 48 | 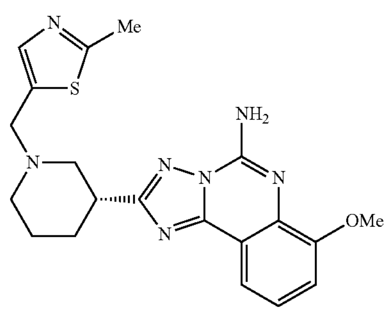 [SMILES: COc1cccc2c1nc(N)n1nc([C@@H]3CCCN(Cc4cnc(C)s4)C3)nc21] | 7-methoxy-2-((3R)-1-((2-methyl-1,3-thiazol-5-yl)methyl)piperidin-3-yl)[1,2,4]triazolo[1,5-c]quinazolin-5-amine | 410 |
| 49 | 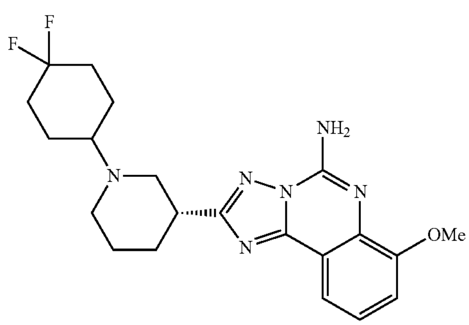 [SMILES: COc1cccc2c1nc(N)n1nc([C@@H]3CCCN(C4CCC(F)(F)CC4)C3)nc21] | 2-((3R)-1-(4,4-difluorocyclohexyl)piperidin-3-yl)-7-methoxy[1,2,4]triazolo[1,5-c]quinazolin-5-amine | 417 |

Examples 50A and 50B

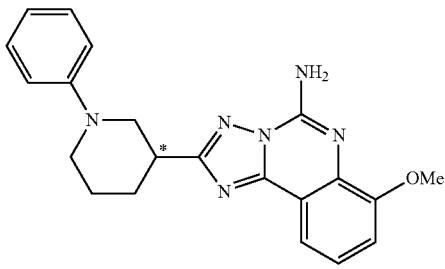 [SMILES: COc1cccc2c1nc(N)n1nc(C3CCCN(c4ccccc4)C3)nc21]

7-methoxy-2-(1-phenylpiperidin-3-yl)-[1,2,4]triazolo[1,5-c]quinazolin-5-amine

Step 1: (±)—N-(2,4-dimethoxybenzyl)-7-methoxy-2-(1-phenylpiperidin-3-yl)-[1,2,4]triazolo[1,5-c]quinazolin-5-amine To a 10 mL sealed tube was charged a tetrahydrofuran solution (3.0 mL) of (±)—N-(2,4-dimethoxybenzyl)-7-methoxy-2-(piperidin-3-yl)-[1,2,4]triazolo[1,5-c]quinazolin-5-amine (120 mg, 0.26 mmol), 3-bromopyridine (126 mg, 0.8 mmol), potassium tert-butoxide (36 mg, 0.32 mmol), bis(dibenzylideneacetone)palladium(0) (58 mg, 0.08 mmol), and 2-dicyclohexylphosphino-2',6'-diisopropoxybiphenyl (50 mg, 0.10 mmol). The resulting mixture was irradiated by microwaves at 115° C. for 3 hours, then cooled to room temperature. Water (10 mL) was added, and the mixture was extracted with ethyl acetate (3×20 mL). The combined organic layers were washed with brine (30 mL), dried (sodium sulfate), filtered, and concentrated in vacuo. The residue was purified by prep-TLC, eluting with pet ether/ethyl acetate 1/1, to afford the title compound. LC/MS=526 [M+1].

Step 2: 7-methoxy-2-(1-phenylpiperidin-3-yl)-[1,2,4]triazolo[1,5-c]quinazolin-5-amine The title compound was made by following the procedures described in Step 3 for EXAMPLE 1, substituting (±)—N-(2,4-dimethoxybenzyl)-7-methoxy-2-(1-phenylpiperidin-3-yl)-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=376 [M+1]. $^1$H-NMR (CD$_3$OD-d$_4$, 400 MHz) δ 8.23 (d, 1H), 7.87 (d, 1H), 7.79 (dd, 1H), 7.42-7.40 (m, 1H), 7.29 (t, 1H), 7.22-7.17 (m, 2H), 4.08-4.01 (m, 1H), 3.92 (s, 3H), 3.72-3.68 (m, 1H), 3.32-3.25 (m, 1H), 2.91-2.86 (m, 1H), 2.29-2.26 (m, 1H), 1.98-1.75 (m, 4H). Chiral resolution of the two enantiomers was achieved by chiral preparative HPLC. Isomer 50A: RT=13.1 min (OJ-H column (4.6*250 mm, 5 μm); hexane (0.1% diethylamine)/ethanol (0.1% diethylamine) 40/60, 1.0 mL/min). Isomer 50B: RT=19.4 min (OJ-H column (4.6*250 mm, 5 μm); hexane (0.1% diethylamine)/ethanol (0.1% diethylamine) 40/60, 1.0 mL/min).

Example 51

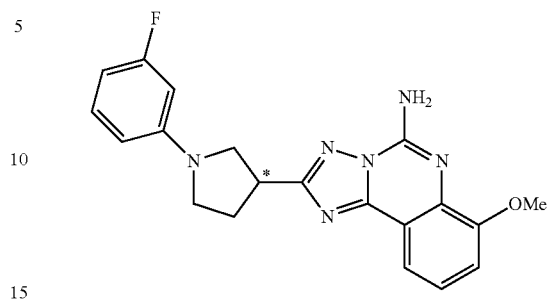

(±)-2-(1-(3-fluorophenyl)pyrrolidin-3-yl)-7-methoxy[1,2,4]triazolo[1,5-c]quinazolin-5-amine The title compound was made by following the procedures described for EXAMPLE 50, substituting (±)—N-(2,4-dimethoxybenzyl)-7-methoxy-2-(pyrrolidin-3-yl)-[1,2,4]triazolo[1,5-c]quinazolin-5-amine for (±)—N-(2,4-dimethoxybenzyl)-7-methoxy-2-(piperidin-3-yl)-[1,2,4]triazolo[1,5-c]quinazolin-5-amine and 1-bromo-3-fluorobenzene for 3-bromopyridine in Step 1. LC/MS=379 [M+1].

Example 52

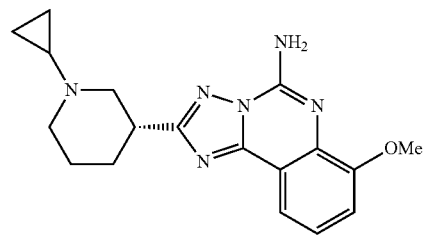 [SMILES: COc1cccc2c1nc(N)n1nc([C@@H]3CCCN(C4CC4)C3)nc21]

(R)-2-(1-cyclopropylpiperidin-3-yl)-7-methoxy-[1,2,4]triazolo[1,5-c]quinazolin-5-amine

Step 1: (R)-2-(1-cyclopropylpiperidin-3-yl)-N-(2,4-dimethoxybenzyl)-7-methoxy-[1,2,4]triazolo[1,5-d]quinazolin-5-amine To a 50 mL round bottom flask was charged a tetrahydrofuran solution (30 mL) of N-(2,4-dimethoxybenzyl)-7-methoxy-2-(piperidin-3-yl)-[1,2,4]triazolo[1,5-c]quinazolin-5-amine (300 mg, 0.66 mmol), cyclopropylboronic acid (114 mg, 1.32 mmol), copper(II) acetate (120 mg, 0.66 mmol), 2'2-bipyridine (104 mg, 0.66 mmol), and sodium carbonate (142 mg, 1.32 mmol). The reaction mixture was stirred at 70° C. for 16 hours under air. Solvent was then removed, and the residue was purified by prep-TLC, eluting with dichloromethane/methanol 50/1, to afford the title compound. LC/MS=489 [M+1].

Step 2: (R)-2-(1-cyclopropylpiperidin-3-yl)-7-methoxy-[1,2,4]triazolo[1,5-c]quinazolin-5-amine The title compound was made by following the procedures described in Step 3 for EXAMPLE 1, substituting (R)-2-(1-cyclopropylpiperidin-3-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=339 [M+1]. $^1$H-NMR (CD$_3$OD-d$_4$, 400 MHz) δ 7.90 (d, 1H), 7.39 (t, 1H), 7.29 (d, 1H), 4.03 (s, 3H), 3.49-3.46 (m, 1H), 3.25-3.20 (m, 1H), 3.15-3.12 (m, 1H), 2.63 (t, 1H), 2.36-2.33 (m, 1H), 2.27-2.24 (m, 1H), 1.91-1.73 (m, 4H), 0.56-0.51 (m, 4H).

Example 53

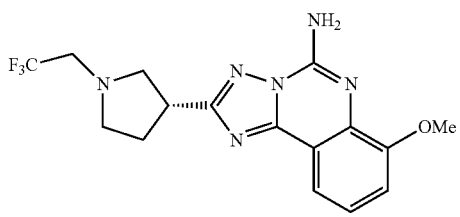 [SMILES: COc1cccc2c1nc(N)n1nc([C@@H]3CCN(CC(F)(F)F)C3)nc21]

(R)-7-methoxy-2-(1-(2,2,2-trifluoroethyl)pyrrolidin-3-yl)-[1,2,4]triazolo[1,5-c]quinazolin-5-amine Step 1: tert-butyl (R)-3-(5-amino-7-methoxy-[1,2,4]triazolo[1,5-c]quinazolin-2-yl)pyrrolidine-1-carboxylate To an acetonitrile (40 mL)/water (40 ml) solution of tert-butyl (R)-3-(5-((2,4-dimethoxybenzyl)amino)-7-methoxy-[1,2,4]triazolo[1,5-c]quinazolin-2-yl)pyrrolidine-1-carboxylate (5.32 g, 9.95 mmol) at room temperature was added ceric ammonium nitrate (21 g, 38.3 mmol). The reaction mixture was stirred for 4 hours, then diluted with water (50 mL) and extracted with ethyl acetate (2×100 mL). The combined organic layers were washed with brine, dried (magnesium sulfate), filtered, and concentrated in vacuo. Chromatography over silica gel, eluting with ethyl acetate/hexanes followed by methanol/ethyl acetate, afforded the title compound. LC/MS=385 [M+1].

Step 2: (R)-7-methoxy-2-(pyrrolidin-3-yl)-[1,2,4]triazolo[1,5-c]quinazolin-5-amine To a methanolic solution (15 mL) of tert-butyl (R)-3-(5-amino-7-methoxy-[1,2,4]triazolo[1,5-c]quinazolin-2-yl)pyrrolidine-1-carboxylate (722 mg, 1.88 mmol) was added a 4.0 M dioxane solution of hydrogen chloride (7 mL, 28.0 mmol). The reaction mixture was stirred at room temperature for 3 hours. It was concentrated in vacuo and diluted with ethyl acetate. 5M Sodium hydroxide solution was added (7 mL, 35.0 mmol), and the aqueous layer was concentrated in vacuo to afford the title compound, which was used in the subsequent step without further purification. LC/MS=285 [M+1].

Step 3: (R)-7-methoxy-2-(1-(2,2,2-trifluoroethyl)pyrrolidin-3-yl)-[1,2,4]triazolo[1,5-c]quinazolin-5-amine To a mixture of (R)-7-methoxy-2-(pyrrolidin-3-yl)-[1,2,4]triazolo[1,5-c]quinazolin-5-amine (144 mg, 0.506 mmol) and potassium carbonate (210 mg, 1.52 mmol) in N,N-dimethylformamide (5 mL) was added 2,2,2-trifluoroethyl trifluoromethanesulfonate (0.146 ml, 1.01 mmol). The reaction mixture was stirred at room temperature for 3 hours. It was diluted with ethyl acetate and washed with water. The aqueous layer was extracted with ethyl acetate, and the combined organic layers were washed with brine and concentrated in vacuo. Chromatography over silica gel, eluting with 30-100% ethyl acetate/hexanes, afforded the title compound. LC/MS=367 [M+1]. $^1$H-NMR (CDCl$_3$, 400 MHz) δ 7.94 (dd, J=8.1, 1.2 Hz, 1H), 7.37 (t, J=8.0 Hz, 1H), 7.16 (dd, J=8.0, 1.2 Hz, 1H), 5.92 (s, 2H), 4.06 (s, 3H), 3.79-3.81 (m, 1H), 3.42 (t, J=8.7 Hz, 1H), 3.17-3.18 (m, 4H), 2.90-2.92 (m, 1H), 2.41-2.43 (m, 2H).

Example 54

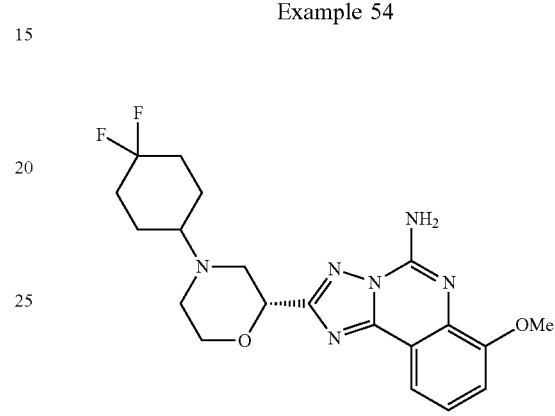

(R)-2-(4-(4,4-difluorocyclohexyl)morpholin-2-yl)-7-methoxy-[1,2,4]triazolo[15-c]quinazolin-5-amine Step 1: tert-butyl (R)-2-(5-((2,4-dimethoxybenzyl)amino)-7-methoxy-[1,2,4]triazolo[1,5-c]quinazolin-2-yl)morpholine-4-carboxylate The title compound was made by following the procedures described for INTERMEDIATE B1, substituting (R)-4-(tert-butoxycarbonyl)morpholine-2-carboxylic acid for (S)-1-(tert-butoxycarbonyl)-4,4-difluoropyrrolidine-2-carboxylic acid and 2,4,6-tripropyl -1,3,5,2,4,6-trioxatriphosphorinane-2,4,6-trioxide for (1-cyano-2-ethoxy-2-oxoethylidenaminooxy)dimethylamino-morpholino-carbenium hexafluorophosphate in Step 3. LC/MS=551 [M+1].

Step 2: (R)—N-(2,4-dimethoxybenzyl)-7-methoxy-2-(morpholin-2-yl)-[1,2,4]triazolo[1,5-c]quinazolin-5-amine The title compound was made by following the procedures described in Step 1 for EXAMPLE 1, substituting tert-butyl (R)-2-(5-((2,4-dimethoxybenzyl)amino)-7-methoxy-[1,2,4]triazolo[1,5-c]quinazolin-2-yl)morpholine-4-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate. LC/MS=451 [M+1].

Step 3: (R)-2-(4-(4,4-difluorocyclohexyl)morpholin-2-yl)-7-methoxy-[1,2,4]triazolo[1,5-c]quinazolin-5-amine The title compound was made by following the procedures described for EXAMPLE 49, substituting (R)—N-(2,4-dimethoxybenzyl)-7-methoxy-2-(morpholin-2-yl)-[1,2,4]triazolo[1,5-c]quinazolin-5-amine for (R)—N-(2,4- dimethoxybenzyl)-7-methoxy-2-(piperidin-3-yl)-[1,2,4]triazolo[1,5-c]quinazolin-5-amine. LC/MS=419 [M+1].

Examples 55A and 55B

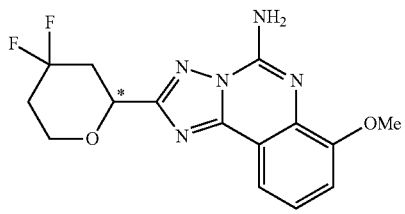 [SMILES: COc1cccc2c1nc(N)n1nc(C3CC(F)(F)CCO3)nc21]

2-(4,4-difluorotetrahydro-2H-pyran-2-yl)-7-methoxy-[1,2,4]triazolo[1,5-c]quinazolin-5-amine Step 1: (±)-ethyl 4,4-difluorotetrahydro-2H-pyran-2-carboxylate To a dichloromethane solution (30 mL) of (±)-ethyl 4-oxotetrahydro-2H-pyran-2-carboxylate (600 mg, 3.48 mmol) was added diethylaminosulfur trifluoride (2.25 g, 13.9 mmol). The reaction mixture was stirred at room temperature for 18 hours. Saturated aqueous potassium carbonate solution (100 mL) was added, and the mixture was extracted with dichloromethane (30 mL×3). The combined organic layers were dried (sodium sulfate), filtered, and concentrated in vacuo. The residue was diluted into ethanol (20 mL), and an aqueous solution (20 mL) of potassium permanganate (1 g) was added. The reaction mixture was stirred at room temperature for 16 hours and concentrated in vacuo. Water (20 mL) was added, and the aqueous layer was extracted with dichloromethane (30 mL×3). The combined organic layers were dried (sodium sulfate), filtered, and concentrated in vacuo to afford the title compound. LC/MS=195 [M+1].

Step 2: (±)-2-(4,4-difluorotetrahydro-2H-pyran-2-yl)-N-(2,4-dimethoxybenzyl)-7-methoxy-[1,2,4]triazolo[1,5-c]quinazolin-5-amine The title compound was made by following the procedures described for INTERMEDIATE A1, substituting (±)-ethyl 4,4-difluorotetrahydro-2H-pyran-2-carboxylate for (R)-1-tert-butyl-3-ethyl piperidine-1,3-dicarboxylate in Step 1. LC/MS=486 [M+1].

Step 3: 2-(4,4-difluorotetrahydro-2H-pyran-2-yl)-7-methoxy-[1,2,4]triazolo[1,5-c]quinazolin-5-amine The title compound was made by following the procedures described in Step 3 for EXAMPLE 1, substituting (±)-2-(4,4-difluorotetrahydro-2H-pyran-2-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=336 [M+1]. Chiral resolution of the two enantiomers was achieved by chiral preparative SFC. Isomer 55A: RT=3.06 min (IA column (4.6*250 mm, 5 μm); methanol (0.1% diethylamine) 0.9 mL/min; supercritical carbon dioxide 2.1 mL/min). Isomer 55B: RT=4.00 min (IA column (4.6*250 mm, 5 μm); methanol (0.1% diethylamine) 0.75 mL/min; supercritical carbon dioxide 2.25 mL/min).

Examples 56A and 56B

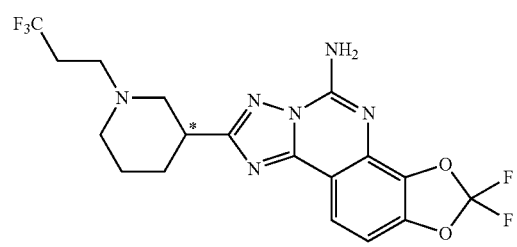 [SMILES: Nc1nc2c3c(ccc2c2nc(C4CCCN(CCC(F)(F)F)C4)nn12)OC(F)(F)O3]

(R)-2,2-difluoro-8-(1-(3,3,3-trifluoropropyl)piperidin-3-yl)-[1,3]dioxolo[4,5-h][1,2,4]triazolo[1,5-c]quinazolin-5-amine The title compound was made by following the procedures described for EXAMPLE 1, substituting (±)-tert-butyl 3-(5-((2,4-dimethoxybenzyl)amino)-2,2-difluoro-[1,3]dioxolo[4,5-h][1,2,4]triazolo[1,5-c]quinazolin-8-yl)piperidine-1-carboxylate for tert-butyl (R)-3-(5-((2,4-dimethoxybenzyl)amino)-7-methoxy-[1,2,4]triazolo[1,5-c]quinazolin-2-yl)piperidine-1-carboxylate in Step 1. LC/MS=445 [M+1]. $^1$H-NMR (CDCl$_3$, 400 MHz) δ 8.13 (d, 1H), 7.19 (d, 1H), 6.18 (br, 1H), 3.32-3.22 (m, 2H), 2.99-2.89 (m, 1H), 2.74-2.73 (m, 2H), 2.54-2.36 (m, 3H), 2.25-2.23 (m, 2H), 1.88-1.87 (m, 1H), 1.77-1.68 (m, 2H). Chiral resolution of the two enantiomers was achieved by chiral preparative SFC (OJ-H column; methanol (0.1% diethylamine) 0.3 mL/min; supercritical carbon dioxide 2.7 mL/min). Isomer 56A: RT=3.3 min. Isomer 56B: RT=4.0 min.

Example 57

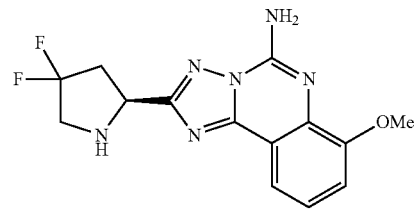 [SMILES: COc1cccc2c1nc(N)n1nc([C@@H]3CC(F)(F)CN3)nc21]

(S)-2-(4,4-difluoropyrrolidin-2-yl)-7-methoxy-[1,2,4]triazolo[1,5-c]quinazolin-5-amine Step 1: (S)-2-(4,4-difluoropyrrolidin-2-yl)-N-(2,4-dimethoxybenzyl)-7-methoxy-[1,2,4]triazolo[1,5-c]quinazolin-5-amine To a methanol solution (25 mL) of tert-butyl (S)-2-(5-((2,4-dimethoxybenzyl)amino)-7-methoxy-[1,2,4]triazolo[1,5-c]quinazolin-2-yl)-4,4-difluoropyrrolidine-1-carboxylate (4.50 g, 7.89 mmol) was added 4.0 M dioxane solution of hydrogen chloride (10 mL, 40.0 mmol). The reaction mixture was stirred for 18 hours and concentrated in vacuo. The residue was dissolved with dichloromethane (500 mL) and washed with 1 M sodium hydroxide solution. A solid was collected through filtration. The organic layer was washed with brine, dried (sodium sulfate), filtered and concentrated in vacuo. The solid thus collected was combined with the solid obtained before through filtration to afford the title compound. LC/MS=471 [M+1].

Step 2: (S)-2-(4,4-difluoropyrrolidin-2-yl)-7-methoxy-[1,2,4]triazolo[1,5-c]quinazolin-5-amine The title compound was made by following the procedures described in Step 3 for EXAMPLE 1, substituting (S)-2-(4,4-difluoropyrrolidin-2-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=321 [M+1].

Examples 58A and 58B

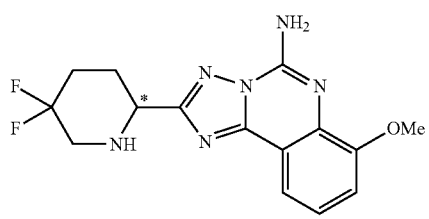 [SMILES: COc1cccc2c1nc(N)n1nc(C3CCC(F)(F)CN3)nc21]

2-(5,5-difluoropiperidin-2-yl)-7-methoxy-[1,2,4]triazolo[1,5-c]quinazolin-5-amine A dichloromethane solution of tert-butyl 2-(5-((2,4-dimethoxybenzyl)amino)-7-methoxy-[1,2,4]triazolo[1,5-c]quinazolin-2-yl)-5,5-difluoropiperidine-1-carboxylate (0.3 g, 0.51 mmol) was treated with trifluoroacetic acid (5 mL), and the mixture was stirred at 60° C. for 12 hours. The reaction mixture was concentrated in vacuo, and the residue was purified by reverse phase HPLC (acetonitrile/water with 0.05% trifluoroacetic acid) to afford the title compound as the trifluoroacetate salt. Chiral resolution of the two enantiomers was achieved by chiral preparative SFC (IC column, 30/70 isopropanol/supercritical carbon dioxide). Isomer 58A: RT=2.85 min (IC column, 40/60 isopropanol/supercritical carbon dioxide). Isomer 58B: RT=3.72 min (IC column, 40/60 isopropanol/supercritical carbon dioxide).

Examples 59A and 59B

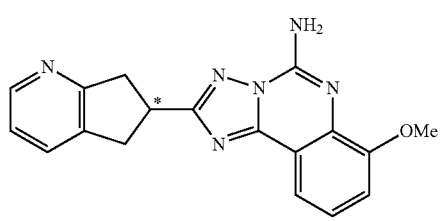 [SMILES: COc1cccc2c1nc(N)n1nc(C3Cc4cccnc4C3)nc21]

2-(6,7-dihydro-5H-cyclopenta[b]pyridin-6-yl)-7-methoxy-[1,2,4]triazolo[1,5-c]quinazolin-5-amine

Step 1: 2-(6,7-dihydro-5H-cyclopenta[b]pyridin-6-yl)-N-(2,4-dimethoxybenzyl)-7-methoxy-[1,2,4]triazolo[1,5-c]quinazolin-5-amine The title compound was made by following the procedures described for INTERMEDIATE B1, substituting 6,7-dihydro-5H-cyclopenta[b]pyridine-6-carboxylic acid for (S)-1-(tert-butoxycarbonyl)-4,4-difluoropyrrolidine-2-carboxylic acid and 1-[bis(dimethylamino)methylene]-1H-1,2,3-triazolo[4,5-b]pyridinium 3-oxid hexafluorophosphate for (1-cyano-2-ethoxy-2-oxoethylidenaminooxy)dimethylamino-morpholino-carbenium hexafluorophosphate in Step 3. LC/MS=483 [M+1].

Step 2: 2-(6,7-dihydro-5H-cyclopenta[b]pyridin-6-yl)-7-methoxy-[1,2,4]triazolo[1,5-c]quinazolin-5-amine The title compound was made by following the procedures described in Step 3 for EXAMPLE 1, substituting 2-(6,7-dihydro-5H-cyclopenta[b]pyridin-6-yl)-N-(2,4-dimethoxybenzyl)-7-methoxy-[1,2,4]triazolo[1,5-c]quinazolin-5-amine for (R)—N-(2,4-dimethoxybenzyl)-7-methoxy-2-(1-(3,3,3-trifluoropropyl)piperidin-3-yl)-[1,2,4]triazolo[1,5-c]quinazolin-5-amine. LC/MS=333 [M+1]. Chiral resolution of the two enantiomers was achieved by chiral preparative SFC (OD-H column; 20% methanol in supercritical carbon dioxide). Isomer 58A: RT=7.24 min. Isomer 58B: RT=8.42 min.

$A_{2A}$ Activity Binding of Compounds of the Invention

Binding affinities of compounds of the invention for the human $A_{2A}$ receptor were determined in a competition binding assay using Scintillation Proximity technology. Thus, 1^μg (^ denotes 1 μg of membrane/well), or preferably 0.25 μg of membranes from HEK293 cells expressing the human A2a receptor were incubated with a compound of the invention at concentrations ranging from 3000 nM to 0.15 nM in a reaction mixture containing also 0.5 nM of a tritiated form of 5-amino-7-[2-phenethyl]-2-(furan-2-yl)-7H-pyrazolo[4,3-e][1,2,4]triazolo[1,5-c]pyrimidine (the tritiated compound) and 25 μg of wheat germ agglutinin-coated yttrium silicate SPA beads for one hour at room temperature with agitation. The beads were then allowed to settle to the bottom of the wells for 1 hr, after which the membrane-associated radioactivity was determined by scintillation counting in a TopCount microplate reader. $K_i$ values were determined using the Cheng-Prusoff equation.

*—in the chemical structures denotes stereogenic centers that were not characterized.

Summary of Materials and Methods Used in $A_{2A}$ Activity Determination:

Materials

HEK293 cells expressing the human, rat, dog or monkey adenosine 2a receptor (Purchased from Perkin-Elmer # RBHA2AM400UA).

The Tritiated compound was prepared in-house by MRL Radiochemistry according to published methods.

Wheat germ agglutinin-coated yttrium silicate SPA beads (GE Healthcare #RPNQ0023). Dilute to 25 mg/mL in assay buffer.

Assay Buffer was prepared in house: Dulbecco's calcium and magnesium free phosphate buffered saline+10 mM $MgCl_2$ Adenosine deaminase from calf intestine, 10 mg/2 mL (Roche #10 102 105 001).
DMSO
A$_{2A}$ antagonist standard (9-chloro-1-(2-furanyl)-[1,2,4]triazolo[1,5-c]quinazolin-5-amine from Tocris Bioscience)

Compound Dilution

Make eight 1:3 serial dilutions in 100% DMSO from a 3 mM compound stock

Transfer 50 nL of compound into a 384-well OptiPlate (Perkin Elmer).

Typically, final concentrations of compound used in the assay ranged from 3000 nM to 0.152 nM.

Radioisotope

Dilute a solution of the Tritiated compound to 1.25 nM in assay buffer. This a 2.5× solution. The final concentration in the assay is 0.5 nM. Calculate the concentration by counting two 5 μL aliquots.

Membrane Preparation

Use *1 ug or preferrably 0.25 ug of membrane/well. Dilute membranes to 9.7 μg/ml in assay buffer. Treat with 20 ug/ml adenosine deaminase (ADA) for 15 minutes at room temperature to degrade endogenous adenosine.

Membrane-Bead Mixture

Use 25 μg/well wheat germ agglutinin-coated yttrium silicate SPA beads.

Mix ADA-treated membranes and SPA beads together for 30 min prior to assay.

Assay Assembly

To the Perkin-Elmer Optiplate-384 containing the compound titration add 20 μL of 2.5× solution of the Tritiated compound and 30 μL of the membrane-bead mixture. Incubate for one hour at room temperature with agitation.

Include total binding (assay buffer+1% DMSO) and non-specific binding (CGS15943, 1 μM) wells.

Counting

Allow the beads to settle for one hour.
Count in TopCount.

Calculations

A curve fitting program (i.e., Prism, Activity Base, Chemcart) is used to determine the EC$_{50}$. The K$_i$ value is calculated using the Cheng-Prusoff equation.

$K_i = EC_{50}/(1+(\text{radioligand concentration}/K_d))$

Counting and Calculations

Counting and calculations were performed as described within the "A$_{2A}$ Activity Binding of Compounds of the Invention" section. Using the foregoing methods, the following results were obtained using compounds of the invention described herein. Each example compound tested is reported in the following format: Example number: A$_{2A}$ K$_i$ (nM) selectivity.

| EXAMPLE | A$_{2A}$ K$_i$ (nM) |
|---|---|
| 1 | 0.6 |
| 2 | 0.3 |
| 3 | 0.4 |
| 4 | 5.4 |
| 5 | 34^ |
| 6 | 3.1 |
| 7 | 29^ |
| 8 | 45^ |
| 9 | 20^ |
| 10 | 20 |
| 11 | 0.4 |
| 12 | 14 |
| 13 | 93 |
| 14 | 6.9 |
| 15 | 1.5 |
| 16 | 7.6^ |
| 17 | 0.7 |
| 18 | 3.0 |
| 19 | 2.0^ |
| 20 | 1.9^ |
| 21 | 3.2^ |
| 22 | 0.8^ |
| 23 | 0.8 |
| 24A | 0.5 |
| 24B | 0.4 |
| 25 | 1.2 |
| 26 | 1.3 |
| 27 | 9.7^ |
| 28 | 11 |
| 29A | 16 |
| 29B | 1.7 |
| 29C | 0.4 |
| 29D | 17 |
| 30A | 91 |
| 30B | 44 |
| 30C | 115 |
| 30D | 660 |
| 31 | 33 |
| 32A | 0.7 |
| 32B | 5.9 |
| 33A | 5.3 |
| 33B | 2.4 |
| 34A | 1.1 |
| 34B | 4.7 |
| 35A | 21 |
| 35B | 54 |
| 35C | 0.3 |
| 35D | 9.9 |
| 36 | 1.2^ |
| 37 | 1.3^ |
| 38 | 4.4^ |
| 39 | 2.7^ |
| 40 | 1.5^ |
| 41 | 1.9^ |
| 42 | 1.1 |
| 43 | 0.6 |
| 44 | 5.0 |
| 45 | 3.8^ |
| 46 | 2.0 |
| 47 | 9.7 |
| 48 | 2.1^ |
| 49 | 5.9 |
| 50A | 0.9^ |
| 50B | 34^ |
| 51 | 1.4^ |
| 52 | 1.2 |
| 53 | 2.0 |
| 54 | 3.0 |
| 55A | 1.9 |
| 55B | 2.0 |
| 56A | 0.8^ |
| 56B | 55^ |
| 57 | 0.5 |
| 58A | 2.4 |
| 58B | 0.3 |

The invention claimed is:

1. A compound of structural formula I:

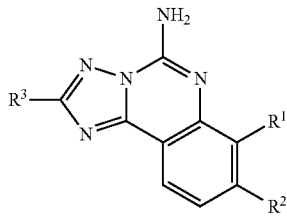

or a pharmaceutically acceptable salt thereof, wherein:
R represents hydrogen or —$C_{1-6}$alkyl,
$R^1$ is selected from the group consisting of hydrogen, —$C_{1-6}$alkyl, —$OC_{1-6}$alkyl, or halogen, said alkyl optionally substituted with 1 to 4 groups of $R^b$;
$R^2$ is selected from the group consisting of hydrogen, —$C_{1-6}$alkyl, or halogen, said alkyl optionally substituted with 1 to 3 groups of $R^b$;
$R^3$ represents $C_{3-10}$ cycloalkyl, or $C_{3-10}$ heterocyclyl, said cycloalkyl and heterocyclyl optionally substituted with 1 to 3 groups of $R^a$;
wherein said $C_{3-10}$ heterocyclyl of $R^3$ is selected from piperidinyl, morpholinyl, tetradropyranyl, azabicyclooctyl, azabicycloheptyl, azepanyl, azetidinyl, pyrrolidinyl, and piperidinone, and wherein:
$R^a$ is selected from the group consisting of —CN, halogen, —$C_{1-4}$haloalkyl, —$OC_{1-4}$haloalkyl, —$C_{1-6}$alkyl, —$C_{1-6}$alkenyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR)_nC_{3-10}$cycloalkyl, —$C(O)C_{1-6}$alkyl, —$C(O)C_{3-10}$cycloalkyl), $SO_2C_{1-6}$alkyl, $C(O)C_{3-10}$ heterocyclyl, $C(O)C_{6-10}$aryl, $SO_2C_{6-10}$aryl, said alkyl, cycloalkyl, alkenyl, aryl and heterocyclyl optionally substituted with 1 to 4 groups of $R^b$;
$R^b$ is selected from the group consisting of —$C_{1-6}$alkyl, $C_{2-4}$alkynyl, —$C_{1-6}$alkylOR, $(CH_2)_nOR$, —$(CH_2)_nC_{1-4}$haloalkyl, —$OC_{1-4}$haloalkyl, halogen, $N(R)_2$, CN, C(O)R, $C(O)CF_3$, —$(CH_2)_nC_{6-10}$ aryl, —$O(CH_2)_nC_{6-10}$ aryl, —$(CH_2)_nC_{3-10}$ heterocyclyl, —$(CH_2)_nC_{3-10}$ cycloalkyl;
and n represents 0-4.

2. The compound according to claim 1 or a pharmaceutically acceptable salt thereof, wherein $R^1$ is —$OC_{1-6}$alkyl and $R^2$ is hydrogen.

3. The compound according to claim 1 or a pharmaceutically acceptable salt thereof, wherein $R^3$ is $C_{3-10}$ heterocyclyl, said heterocycle group optionally substituted with 1 to 3 groups of $R^a$.

4. The compound according to claim 1 or a pharmaceutically acceptable salt thereof, wherein $R^3$ is optionally substituted $C_{3-10}$ cycloalkyl.

5. The compound according to claim 4 or a pharmaceutically acceptable salt thereof, wherein $R^3$ is selected from the group of optionally substituted cyclohexyl, cyclobutyl, cyclopropyl, and cyclopentyl.

6. The compound according to claim 1 wherein $R^a$ is selected from the group consisting of halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR)_nC_{3-10}$cycloalkyl, —$C(O)C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

7. The compound according to claim 6 or a pharmaceutically acceptable salt thereof, wherein $R^a$ is selected from the group consisting of $CH_3$, $CH_2CH_3$, —$(CH_2)_3CH_3$, $CH_2CH(CH_3)_2$, $C(CH_3)_2CH_2CH_3$, $(CH_2)_nOCH_3$, $CH_2CF_2CF_3$, $(CH_2)_nCF_3$, halogen, $(CH_2)$ $CH(CF_3)_2$, $CH_2CHF_2$, $C(CH_3)_2C\equiv C$, —$(CH_2)_nN(R)_2$, OH, C(O)cyclopropyl, $(CHR)_n$cyclopropyl, $(CHR)_n$pyridyl, $(CHR)_n$tetrahydropyranyl, $(CHR)_n$cyclobutyl, $(CHR)_n$thiadiazolyl, $(CHR)_n$oxetanyl, $(CHR)_n$cyclopentyl, $(CHR)_n$cyclohexyl, $(CHR)_n$phenyl, $(CHR)_n$thiazolyl, C(O)phenyl, C(O)pyridyl, $C(O)C(CH_3)_2F$, C(O)oxazolyl, $C(O)C(CH_3)_3$, C(O)thiophenyl, $SO_2$phenyl, $(CHR)_n$cyclopentyl, $(CHR1)_n$morpholinyl, and $(CHR)_n$tetrahydrofuranyl, said cyclopropyl, pyridyl, tetrahydropyranyl, cyclohexyl, cyclobutyl, thiadiazolyl, oxetanyl, cyclopentyl, phenyl, thiazolyl, oxazolyl, thiophenyl, morpholinyl, tetrahydrofuranyl, optionally substituted with 1 to 3 groups of $R^b$.

8. The compound according to claim 1 or a pharmaceutically acceptable salt thereof wherein $R^3$ is substituted with 1 to 3 groups of $R^a$ selected from the group consisting of $CH_2CF_3$, halogen, $CF_3$, $(CH_2)_2CF_3$, $CH_2CHF_2$, $N(R)_2$, OH, $CH_3$, and $CH_2CH_3$.

9. The compound according to claim 1 or a pharmaceutically acceptable salt thereof wherein $R^b$ is selected from halogen, $CH_3$, $CHF_2$, $CF_3$, $C(O)CF_3$, $CH(CH_3)_2$, $N(CH_3)_2$, $C(CH_3)_3$, $CH_2CH_3$, $C(CH_3)F_2$, $OCH_3$, OH, and $CH_2OH$.

10. The compound according to claim 1 represented by structural formula II:

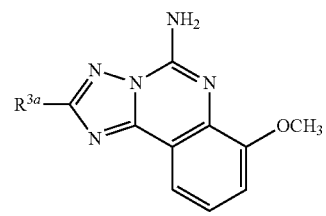

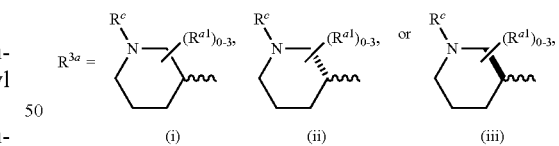

or a pharmaceutically acceptable salt thereof, wherein $R^c$ is hydrogen or $R^a$, and $R^{a1}$ is $R^a$.

11. The compound according to claim 10 or a pharmaceutically acceptable salt thereof wherein $R^c$ is selected from the group consisting of hydrogen, halogen, —$C_{1-4}$haloalkyl, —$OC_{1-4}$haloalkyl, —$C_{1-6}$alkyl, $(CH_2)_nN(R)_2$, —$(CH_2)_n$ $OC_{1-6}$alkyl, OH, $(CHR)_nC_{6-10}$aryl, $(CHR)_nC_{3-10}$ heterocyclyl, $(CHR)_nC_{3-10}$cycloalkyl, —$C(O)C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

12. A compound according to claim 1 represented by structural formula III:

83

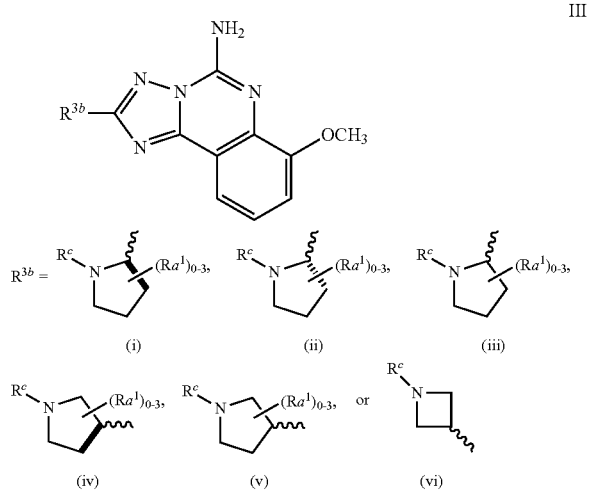

or a pharmaceutically acceptable salt thereof, wherein $R^c$ is hydrogen or $R^a$, $R^{a1}$ is $R^a$.

13. The compound according to claim 12 or pharmaceutically acceptable salt thereof wherein $R^c$ is selected from the group consisting of hydrogen, halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR))_nC_{3-10}$cycloalkyl, —$C(O)C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

14. The compound according to claim 1 represented by structural formula IV:

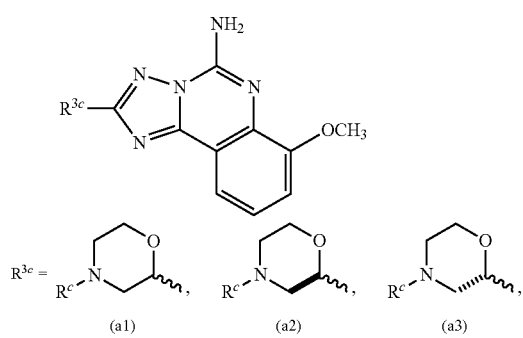

or a pharmaceutically acceptable salt thereof, wherein $R^c$ is hydrogen or $R^a$.

15. The compound according to claim 14 or pharmaceutically acceptable salt thereof wherein $R^c$ is selected from the group consisting of hydrogen, halogen, —$C_{1-4}$haloalkyl, —$OC_{1-4}$haloalkyl, —$C_{1-6}$alkyl, $(CH_2)_nN(R)_2$, —$(CH_2)_nOC_{1-6}$alkyl, OH, $(CHR)_nC_{6-10}$aryl, $(CHR)_nC_{3-10}$ heterocyclyl, $(CHR))_nC_{3-10}$cycloalkyl, —$C(O)C_{1-6}$alkyl, —$C(O)C_{3-10}$cycloalkyl), —$C(O)C_{3-10}$heterocyclyl, said alkyl, cycloalkyl, aryl and heterocyclyl optionally substituted with 1 to 4 groups of $R^b$.

16. A compound which is:
(R)-7-methoxy-2-(1-(3,3,3-trifluoropropyl)piperidin-3-yl)-[1,2,4]triazolo[1,5-c]quinazolin-5-amine,
(R)-7-methoxy-2-(1-(3,3,3-trifluoro-2-(trifluoromethyl)propyl)piperidin-3-yl)-[1,2,4]triazolo[1,5-c]quinazolin-5-amine,

84

(R)-2-(1-(2,2-difluoroethyl)piperidin-3-yl)-7-methoxy-[1,2,4]triazolo[1,5-c]quinazolin-5-amine,
(R)-2-(1-(2-(dimethylamino)ethyl)piperidin-3-yl)-7-methoxy-[1,2,4]triazolo[1,5-c]quinazolin-5-amine,
(R)-2-(1-ethylpiperidin-3-yl)-7-methoxy-[1,2,4]triazolo[1,5-c]quinazolin-5-amine,
(R)-7-methoxy-2-(1-(2-methoxyethyl)piperidin-3-yl)-[1,2,4]triazolo[1,5-c]quinazolin-5-amine,
(R)-2-(1-butylpiperidin-3-yl)-7-methoxy-[1,2,4]triazolo[1,5-c]quinazolin-5-amine,
(R)-2-(1-isobutylpiperidin-3-yl)-7-methoxy-[1,2,4]triazolo[1,5-c]quinazolin-5-amine,
(R)-7-methoxy-2-(1-(2-methylbut-3-yn-2-yl)piperidin-3-yl)-[1,2,4]triazolo[1,5-c]quinazolin-5-amine,
(R)-7-methoxy-2-(1-((1-methylcyclopropyl)methyl)piperidin-3-yl)-[1,2,4]triazolo[1,5-c]quinazolin-5-amine,
(R)-7-methoxy-2-(1-(3,3,4,4,4-pentafluorobutyl)piperidin-3-yl)-[1,2,4]triazolo[1,5-c]quinazolin-5-amine,
(S)-7-methoxy-2-(1-(3,3,3-trifluoropropyl)piperidin-3-yl)-[1,2,4]triazolo[1,5-c]quinazolin-5-amine,
(R)-7-methoxy-2-(piperidin-3-yl)-[1,2,4]triazolo[1,5-c]quinazolin-5-amine,
(R)-2-(1-(2-cyclopropylethyl)piperidin-3-yl)-7-methoxy-[1,2,4]triazolo[1,5-c]quinazolin -5-amine,
(R)-7-methoxy-2-(1-(2-morpholinoethyl)piperidin-3-yl)-[1,2,4]triazolo[1,5-c]quinazolin -5-amine,
(R)-7-methoxy-2-(1-(4,4,4-trifluorobutyl)piperidin-3-yl)-[1,2,4]triazolo[1,5-c]quinazolin -5-amine,
(R)-2-(1-((3,3-difluorocyclobutyl)methyl)piperidin-3-yl)-7-methoxy-[1,2,4]triazolo[1,5-c]quinazolin-5-amine,
(R)-7-methoxy-2-(1-((3-methyloxetan-3-yl)methyl)piperidin-3-yl)-[1,2,4]triazolo[5-c]quinazolin-5-amine,
(R)-7-methoxy-2-(1-(5-methyl-1,3,4-thiadiazol-2-yl)piperidin-3-yl)-[1,2,4]triazolo[1,5-c]quinazolin-5-amine,
(R)-2-(1-(1,3,4-thiadiazol-2-yl)piperidin-3-yl)-7-methoxy-[1,2,4]triazolo[1,5-c]quinazolin-5-amine,
(R)-2-(1-(1,2,4-thiadiazol-5-yl)piperidin-3-yl)-7-methoxy-[1,2,4]triazolo[1,5-c]quinazolin-5-amine,
(R)-7-methoxy-2-(1-(5-methylthiazol-2-yl)piperidin-3-yl)-[1,2,4]triazolo[1,5-c]quinazolin-5-amine,
(R)-7-methoxy-2-(1-(2,2,2-trifluoroethyl)piperidin-3-yl)-[1,2,4]triazolo[1,5-c]quinazolin -5-amine,
2-((R)-1-((R)-2-cyclopropyl-2-fluoroethyl)piperidin-3-yl)-7-methoxy-[1,2,4]triazolo[1,5-c]quinazolin-5-amine,
2-((R)-1-((S)-2-cyclopropyl-2-fluoroethyl)piperidin-3-yl)-7-methoxy-[1,2,4]triazolo[1,5-c]quinazolin-5-amine,
R)-2-(1-(2,2-difluoroethyl)piperidin-3-yl)-7-(difluoromethoxy)-[1,2,4]triazolo[1,5-c]quinazolin-5-amine,
(R)-8-chloro-2-(1-(2,2-difluoroethyl)piperidin-3-yl)-[1,2,4]triazolo[1,5-c]quinazolin-5-amine,
(±)-7-chloro-2-(1-(3,3,3-trifluoropropyl)piperidin-3-yl)-[1,2,4]triazolo[1,5-c]quinazolin -5-amine,
(R)-2-(1-(2,2-difluoroethyl)piperidin-3-yl)-[1,2,4]triazolo[1,5-c]quinazolin-5-amine,
7-methoxy-2-(3-(3,3,3-trifluoropropyl)cyclohexyl)-[1,2,4]triazolo[1,5-c]quinazolin-5-amine,
(±)-7-methoxy-2-(3-(3,3,3-trifluoropropylidene)cyclohexyl)-[1,2,4]triazolo[1,5-c]quinazolin-5-amine
2-(3-aminocyclohexyl)-7-methoxy-[1,2,4]triazolo[1,5-c]quinazolin-5-amine,
(R)-7-methoxy-2-(1-(tert-pentyl)piperidin-3-yl)-[1,2,4]triazolo[1,5-c]quinazolin-5-amine, 7-methoxy-2-(1-(2,2,2-trifluoroethyl)azepan-3-yl)-[1,2,4]triazolo[1,5-c]quinazolin-5-amine, 2-(5,5-difluoropiperidin-3-yl)-7-methoxy-[1,2,4]triazolo[1,5-c]quinazolin-5-amine,
2-(1-(2,2-difluoroethyl)-5,5-difluoropiperidin-3-yl)-7-methoxy-[1,2,4]triazolo[1,5-c]quinazolin-5-amine,
7-methoxy-2-(2-(2,2,2-trifluoroethyl)-2-azabicyclo[2.2.2]octan-6-yl)-[1,2,4]triazolo[1,5-c]quinazolin-5-amine,
(R)-7-methoxy-2-(1-(phenylsulfonyl)piperidin-3-yl)-[1,2,4]triazolo[1,5-c]quinazolin-5-amine,
(R)-(3-(5-amino-7-methoxy-[1,2,4]triazolo[1,5-c]quinazolin-2-yl)piperidin-1-yl)(phenyl)methanone,
2-((3R)-1-(2,2-dimethylpropanoyl)piperidin-3-yl)-7-methoxy[1,2,4]triazolo[1,5-c]quinazolin-5-amine,
7-methoxy-2-((3R)-1-((4-methyl-1,3-oxazol-5-yl)carbonyl)piperidin-3-yl)[1,2,4]triazolo[1,5-c]quinazolin-5-amine,
7-methoxy-2-((3R)-1-((3-methoxyphenyl) carbonyl)piperidin-3-yl)[1,2,4]triazolo[1,5-c]quinazolin-5-amine,
(R)-1-(3-(5-amino-7-methoxy-[1,2,4]triazolo[1,5-c]quinazolin-2-yl)piperidin-1-yl)-2-fluoro-2-methylpropan-1-one,
(R)-2-(1-(2-fluoro-2-methylpropyl)piperidin-3-yl)-7-methoxy-[1,2,4]triazolo[1,5-c]quinazolin-5-amine,
(R)-7-methoxy-2-(1-((tetrahydro-2H-pyran-4-yl)methyl)piperidin-3-yl)-[1,2,4]triazolo[1,5-c]quinazolin-5-amine,
7-methoxy-2-((3R)-1-(pyridin-3-ylmethyl)piperidin-3-yl)[1,2,4]triazolo[1,5-c]quinazolin -5-amine,
2-((3R)-1-[3-fluoro-5-(trifluoromethyl)benzyl)piperidin-3-yl)-7-methoxy[1,2,4]triazolo[1,5-c]quinazolin-5-amine,
2-((3R)-1-(cyclopentylmethyl)piperidin-3-yl)-7-methoxy[1,2,4]triazolo[1,5-c]quinazolin -5-amine,
7-methoxy-2-((3R)-1-((2-methyl-1,3-thiazol-5-yl)methyl)piperidin-3-yl)[1,2,4]triazolo[1,5-c]quinazolin-5-amine,
2-((3R)-1-(4,4-difluorocyclohexyl)piperidin-3-yl)-7-methoxy[1,2,4]triazolo[1,5-c]quinazolin-5-amine,
7-methoxy-2-(1-phenylpiperidin-3-yl)-[1,2,4]triazolo[1,5-c]quinazolin-5-amine,
(R)-2-(1-(3-fluoropyridin-2-yl)piperidin-3-yl)-7-methoxy-[1,2,4]triazolo[1,5-c]quinazolin-5-amine,
(R)-2-(1-cyclopropylpiperidin-3-yl)-7-methoxy-[1,2,4]triazolo[1,5-c]quinazolin-5-amine,
(R)-2-(1-cyclopropylpiperidin-3-yl)-7-methoxy-[1,2,4]triazolo[1,5-c]quinazolin-5-amine,
7-methoxy-2-(4-(2,2,2-trifluoroethyl)morpholin-2-yl)-[1,2,4]triazolo[1,5-c]quinazolin-5-amine,
(±)-2-(1-(3-fluorophenyl)pyrrolidin-3-yl)-7-methoxy-[1,2,4]triazolo[1,5-c]quinazolin-5-amine,
7-methoxy-2-(tetrahydro-2H-pyran-2-yl)-[1,2,4]triazolo[1,5-c]quinazolin-5-amine,
(R)-2,2-difluoro-8-(1-(3,3,3-trifluoropropyl)piperidin-3-yl)-[1,3]dioxolo[4,5-h][1,2,4]triazolo[1,5-c]quinazolin-5-amine,
(R)-7-methoxy-2-(1-(2,2,2-trifluoroethyl)pyrrolidin-3-yl)-[1,2,4]triazolo[1,5-c]quinazolin-5-amine,
(R)-2-(4-(4,4-difluorocyclohexyl)morpholin-2-yl)-7-methoxy-[1,2,4]triazolo[1,5-c]quinazolin-5-amine,
2-(4,4-difluorotetrahydro-2H-pyran-2-yl)-7-methoxy-[1,2,4]triazolo[1,5-c]quinazolin-5-amine,
(S)-2-(4,4-difluoropyrrolidin-2-yl)-7-methoxy-[1,2,4]triazolo[1,5-c]quinazolin-5-amine,
2-(5,5-difluoropiperidin-2-yl)-7-methoxy-[1,2,4]triazolo[1,5-c]quinazolin-5-amine,
2-(6,7-dihydro-5H-cyclopenta[b]pyridin-6-yl)-7-methoxy-[1,2,4]triazolo[1,5-c]quinazolin-5-amine,
or a pharmaceutical salt thereof.

17. A pharmaceutical composition comprising a compound of formula I of claim 1 or a pharmaceutically acceptable salt thereof, and at least one excipient.

* * * * *